United States Patent
Tsai et al.

(10) Patent No.: US 10,781,266 B2
(45) Date of Patent: Sep. 22, 2020

(54) ANTIBODIES SPECIFIC TO ALPHA-ENOLASE AND USES THEREOF

(71) Applicants: DEVELOPMENT CENTER FOR BIOTECHNOLOGY, New Taipei (TW); NATIONAL HEALTH RESEARCH INSTITUTES, Zhunan, Miaoli County (TW)

(72) Inventors: Shih-Chong Tsai, New Taipei (TW); Ta-Tung Yuan, New Taipei (TW); Shih-Chi Tseng, New Taipei (TW); Jiann-Shiun Lai, New Taipei (TW); Chia-Cheng Wu, New Taipei (TW); Po-Yin Lin, New Taipei (TW); Ya-Wei Tsai, New Taipei (TW); Chao-Yang Huang, New Taipei (TW); Ying-Yung Lok, New Taipei (TW); Chung-Hsiun Wu, New Taipei (TW); Hsien-Yu Tsai, New Taipei (TW); Neng-Yao Shih, Zhunan (TW); Ko-Jiunn Liu, Zhunan (TW); Li-Tzong Chen, Zhunan (TW)

(73) Assignees: DEVELOPMENT CENTER FOR BIOTECHNOLOGY, New Taipei (TW); NATIONAL HEALTH RESEARCH INSTITUTES, Zhunan, Miaoli County (TW)

( * ) Notice: Subject to any disclaimer, the term of this patent is extended or adjusted under 35 U.S.C. 154(b) by 180 days.

(21) Appl. No.: 15/924,878

(22) Filed: Mar. 19, 2018

(65) Prior Publication Data

US 2019/0322762 A1    Oct. 24, 2019

(30) Foreign Application Priority Data

Mar. 16, 2018    (JP) ................. 2018-050021

(51) Int. Cl.
*A61K 39/00*    (2006.01)
*C07K 16/40*    (2006.01)
*A61P 35/00*    (2006.01)
*G01N 33/574*    (2006.01)

(52) U.S. Cl.
CPC .............. *C07K 16/40* (2013.01); *A61P 35/00* (2018.01); *G01N 33/57484* (2013.01); *C07K 2317/24* (2013.01); *C07K 2317/732* (2013.01); *C07K 2317/76* (2013.01); *C07K 2317/92* (2013.01); *G01N 2333/988* (2013.01)

(58) Field of Classification Search
CPC ....................................................... C07K 16/40
See application file for complete search history.

(56) References Cited

U.S. PATENT DOCUMENTS

| | | | |
|---|---|---|---|
| 9,382,331 B2 | 7/2016 | Tsai et al. | |
| 9,527,922 B2 | 12/2016 | Tsai et al. | |
| 9,750,804 B2 | 9/2017 | Tsai et al. | |
| 2011/0182907 A1 | 7/2011 | Leu et al. | |
| 2012/0195900 A1 | 8/2012 | Ghayur et al. | |
| 2015/0094990 A1 | 4/2015 | Beisiegel et al. | |
| 2016/0185876 A1 | 6/2016 | Tsai et al. | |

FOREIGN PATENT DOCUMENTS

| | | |
|---|---|---|
| GB | 2429013 A | 2/2007 |
| WO | 2007024746 A1 | 3/2007 |
| WO | 2009114748 A1 | 9/2009 |
| WO | 2011041894 A1 | 4/2011 |
| WO | 2011143307 A1 | 11/2011 |
| WO | 2012175691 A1 | 12/2012 |
| WO | 2015094330 A1 | 6/2015 |

OTHER PUBLICATIONS

Brown et al (J. Immunol. May 1996; 156(9):3285-3291 (Year: 1996).*

Vajdos et al (J. Mol. Biol. Jul. 5, 2002;320(2); 415-428) (Year: 2002).*

Douglas D. Banks, et al., "Removal of Cysteinylation from an Unpaired Sulfhydryl in the Variable Region of a Recombinant Monoclonal IgG1 Antibody Improves Homogeneity, Stability, and Biological Activity", Journal of Pharmaceutical Sciences, Feb. 2008, vol. 97, No. 2, p. 764-799.

English translation of an Office Action dated Feb. 5, 2019 in counterpart Japanese Patent Application No. P2018-050021.

* cited by examiner

*Primary Examiner* — Sheela J. Huff

(74) *Attorney, Agent, or Firm* — Ladas & Parry LLP

(57) ABSTRACT

An antibody, or an antigen-binding fragment there, binding human ENO1 (GenBank: AAH506421.1) is provided. Methods for treating an ENO1 protein-related disease or disorder, inhibiting cancer invasion and diagnosis of cancer are also provided.

10 Claims, 44 Drawing Sheets

Specification includes a Sequence Listing.

FIG. 5A

```
Kabat  1       5        10       15       20       25          36        40
       EVQLQQSGPELVKPGASVKMSCKASGYTFTSCVMNWVKQKPGQG              SEQ ID NO:1
                     FR1                  HCDR1        FR2
                                         SEQ ID NO:3

Kabat  45                                        66  70  75   80 82ABC
       LEWIGYINPYNDGTKYNEKFKGKATLTSDKSSSTAYMELSSLTS              SEQ ID:NO1
                   HCDR2                       FR3
                  SEQ ID NO:4

Kabat  85    90  9394                           105    110
       EDSAVYYCAREGFYYGNFDNWGQGTTLTVSS                           SEQ ID:NO1
                     HCDR3              FR4
                    SEQ ID NO:5
```

FIG.5B

Kabat    1    5    10    15    20                      35      40
         DIQMTQSPASLSASVGETVTITCRASENIYSYLTWYQQKQGKS SEQ ID NO:2
                     FR1              LCDR1         FR2
                                    SEQ ID NO:6

Kabat   45              60      65   70   75    80    85
        PQLLVYNAKTLPEGVPSRFSGSGSGTQFSLKINSLQPEDFGSY SEQ ID NO:2
              LCDR2                        FR3
              SEQ ID NO:7

Kabat              100  104
        YCQHHYGTPYTFGGGTKLEITR    SEQ ID: NO2
           LCDR3      FR4
           SEQ ID NO:8

FIG.6A

Primary alignment of V_L segments

```
Kabat      1       5        10        15        20                    35      40
                                                        LCDR1
           DIQMTQSPASLSASVGETVTITC[RASENIYSYLT]WYQQKQGKS
           DIQMTQSPSSLSASVGDRVTITC[RASENIYSYLT]WYQQKPGKA
                        FR1                                         FR2
                                                  SEQ ID NO:6

Kabat      45                      60        65        70       75       80      85
                  LCDR2
           PQLLVY[NAKTLPE]GVPSRFSGSGSGTQFSLKINSLQPEDFGSY
           PKLLIY[NAKTLPE]GVPSRFSGSGSGTDFTLTISSLQPEDFATY
                                                       FR3
                  SEQ ID NO:7

Kabat            LCDR3    100   104
           YC[QHHYGTPYT]FGGGTKLEITR             SEQ ID NO: 2
           YC[QHHYGTPYT]FGQGTKLEIKR             SEQ ID NO: 9
                  SEQ ID NO:8
```

Clone10 : Musmus IGKV12-44*01 F
Human template: V kappa I

FIG. 6A (Cont.) Primary alignment of V$_H$ segments

```
Kabat   1     5      10       15      20    25       HCDR1          36           40
                                                  ──────────                ──────────
        EVQLQQSGPELVKPGASVKMSCKAS[GYTFTSCVMN]WVKQKPGQG
        EVQLVESGGGLVQPGGSLRLSCAAS[GYTFTSCVMN]WVRQAPGKG
              FR1                                              FR2
                                             SEQ ID NO:3

Kabat   45          HCDR2               66    70     75     80 82A B C
                ──────────────────                        ──────────
        LEWIG[YINPYNDGTKYNEKFKG]KATLTSDKSSSTAYMELSSLTS
        LEWVA[YINPYNDGTKYNEKFKG]RFTISRDDSKNTLYLQMNSLRA
                 SEQ ID NO:4                                     FR3

Kabat   85   90 9394   HCDR3      105    110
                    ──────────         ──────────
        EDSAVYYCAR[EGFYYGNFDN]WGQGTTLTVSS        SEQ ID NO:1
        EDTAVYYCAR[EGFYYGNFDN]WGQGTLVTVSS        SEQ ID NO:10
                      SEQ ID NO:5
```

Clone10 : \Musmus IGHV1-14*01 F
Human template: VH III

FIG. 6B

Primary alignment of V$_L$ segments

```
Kabat         1       5        10       15       20                    LCDR1           35       40
                                            FR1                                                            FR2
      DIQMTQSPASLSASVGETVTITC[RASENIYSYLT]WYQQKQGKS
      DIQMTQSPSSLSASVGDRVTITC[RASENIYSYLT]WYQQKPGKA
                                                          SEQ ID NO:6

Kabat         45               LCDR2                 60       65       70       75       80       85
                                                                                        FR3
      PQLLVY[NAKTLPE]GVPSRFSGSGSGTQFSLKINSLQPEDFGSY
      PKLLIY[NAKTLPE]GVPSRFSGSGSGTDFTLTISSLQPEDFATY
                SEQ ID NO:7

Kabat         LCDR3            100      104
      YC[QHHYGTPYT]FGGGTKLEITR                  SEQ ID NO:2
      YC[QHHYGTPYT]FGQGTKLEIKR                  SEQ ID NO:9
            SEQ ID NO:8
```

Clone10 : Musmus IGKV12-44*01 F
Human template: V kappa I

FIG. 6B (Cont.) Primary alignment of V_H segments

```
Kabat      1         5        10        15        20        25           HCDR1    36       40
MC10       EVQLQQSGPELVKPGASVKMSCKAS [GYTFTSCVMN] WVKQKPGQG
HuC10      QVQLVQSGAEVKKPGASVKVSCKAS [GYTFTSCVMN] WVRQAPGQG
                      FR1                         SEQ ID NO:3      FR2

Kabat      45                            66         70        75      80 82A B C
              HCDR2
MC10       LEWIG [YINPYNDGTKYNEKFKG] KATLTSDKSSSTAYMELSSLTS
HuC10      LEWMG [YINPYNDGTKYNEKFKG] RVTMTDTSTSTAYMELRSLRS
                   SEQ ID NO:4                             FR3

Kabat      85        90  9394        HCDR3           105       110
MC10       EDSAVYYCAR [EGFYYGNFDN] WGQGTTLTVSS                    SEQ ID NO:1
HuC10      DDTAVYYCAR [EGFYYGNFDN] WGQGTLVTVSS                    SEQ ID NO:11
                            SEQ ID NO:5
```

Clone10 : Musmus IGHV1-14*01
Human template (database): IGHV1-18*01 F/IGHJ4*03

FIG.13A

```
         10         20         30         40         50         60
GACATCCAGATGACCCAGTCCCCCTCCAGCCTGTCTGCCCTCTGTGGGGACAGAGTGACC
:: ::::::::: :::::::::::::: ::::::: .  :: :::: ::::: :::: ::
GATATCCAGATGACCCAGTCCCCCAGTCCCCGTCCCGCCTCTGTGGGGATAGGGTCACC 70         80         90        100        110        120
ATCACCTGTCGGGCCTCCGAGAACACTCTACTCCTACCTGACCTGGTATCAGCAGAAGCC
:: :::::::: :: :::::::: ::::: :: ::::::::::::::::::::::: :::
ATCACCTGCGAGCAAGTGAGAATTATTTACAGTTATTTAACATGGTATCAACAGAAACCA 130        140        150        160        170        180
GGCAAGGCCCCCAAGCTGCTGATCTACAAGGCCAAGACCCTGCCCGGAGGGGTGCCCTCT
:: :: :: ::::::::: :: :::::: ::: :: :::::: :: ::: :::::::::
GGAAAAGCTCCGAAACTACTGATTTACAATGCAAAAACCTTACCAGAAGGAGTCCCTTCT 190        200        210        220        230        240
AGATTCTCCGGCTCTGGCTCTGGGACCGACTTTACCCTGACCATCAGCTCCCTGCAGCCC
::  :: ::::: ::::::: ::: :::::::: :::: ::::::: :: :::::::: :
CGCTTCTCTGGTTCCGGCTCTGGGGACGGATTTCACTCTGACCATCAGCAGTCTGCAGCCG 250        260        270        280        290        300
GAGGACTTCGCCACCTACTACTGCCAGCAACTACGGCACCCCCTACACCTTTGGCCAG
:: :::::: ::::::::::::: ::::: :: :::::: ::::: :: :::::::::
GAAGACTTCGCAACTTATTACTGTCAACATCATTATGGTACTCCGTACACGTTCGGACAG 310        320
GGCACCAAGGTGGAAATCAAGCG       SEQ ID NO:14
::  ::::::::::: :::::: 
GGTACCAAGGTGGAGATCAAACG       SEQ ID NO:15
```

| 14D Rank | Clone ID | Day 14 Titer (mg/L) | Day 5 Titer (mg/L) |
|---|---|---|---|
| 1 | FF6D5 | | 155 |
| 2 | FF5H7 | | 147 |
| 3 | FF6C6 | | 125.2 |
| 4 | FF7D10 | | 118.9 |
| 5 | FF8G7 | | 131.9 |
| 6 | FF4B7 | | 155.6 |
| 7 | FF5F12 | 302 | 135 |
| 8 | FF3D2 | 284.4 | 119.2 |
| 9 | FF5F11 | 282.8 | 154.6 |
| 10 | FF6F5 | 277.6 | 154 |
| 11 | FF4C7 | 267.1 | 94.2 |
| 12 | FF1D9 | 258.8 | 90.4 |
| 13 | FF6F9 | 255.7 | 125.3 |
| 14 | FF2D5 | 253.1 | 124.6 |
| 15 | FF5F10 | 247.8 | 91.3 |

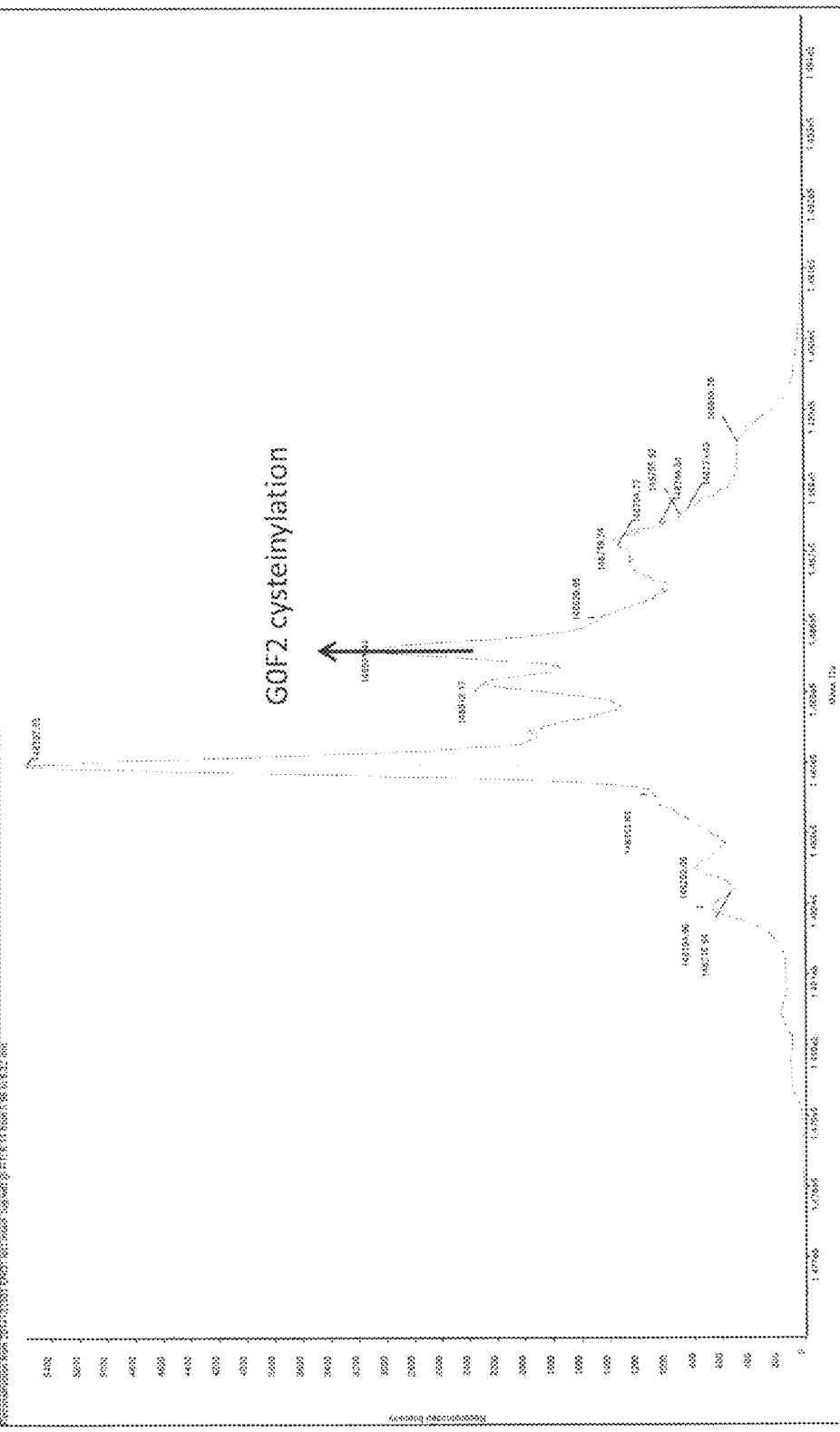
Fig. 14A  LOT 1

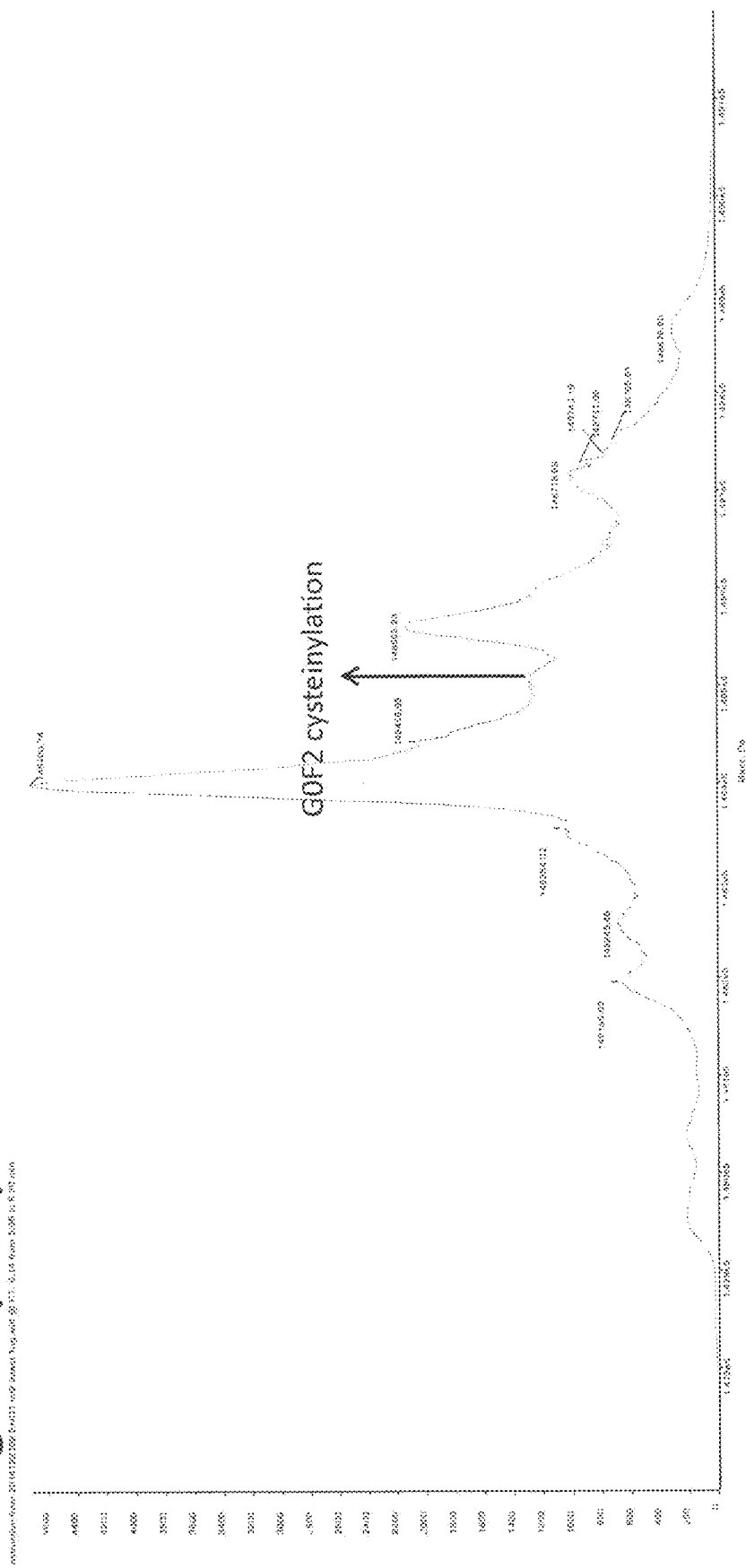
Fig. 14A (Cont.) LOT 2

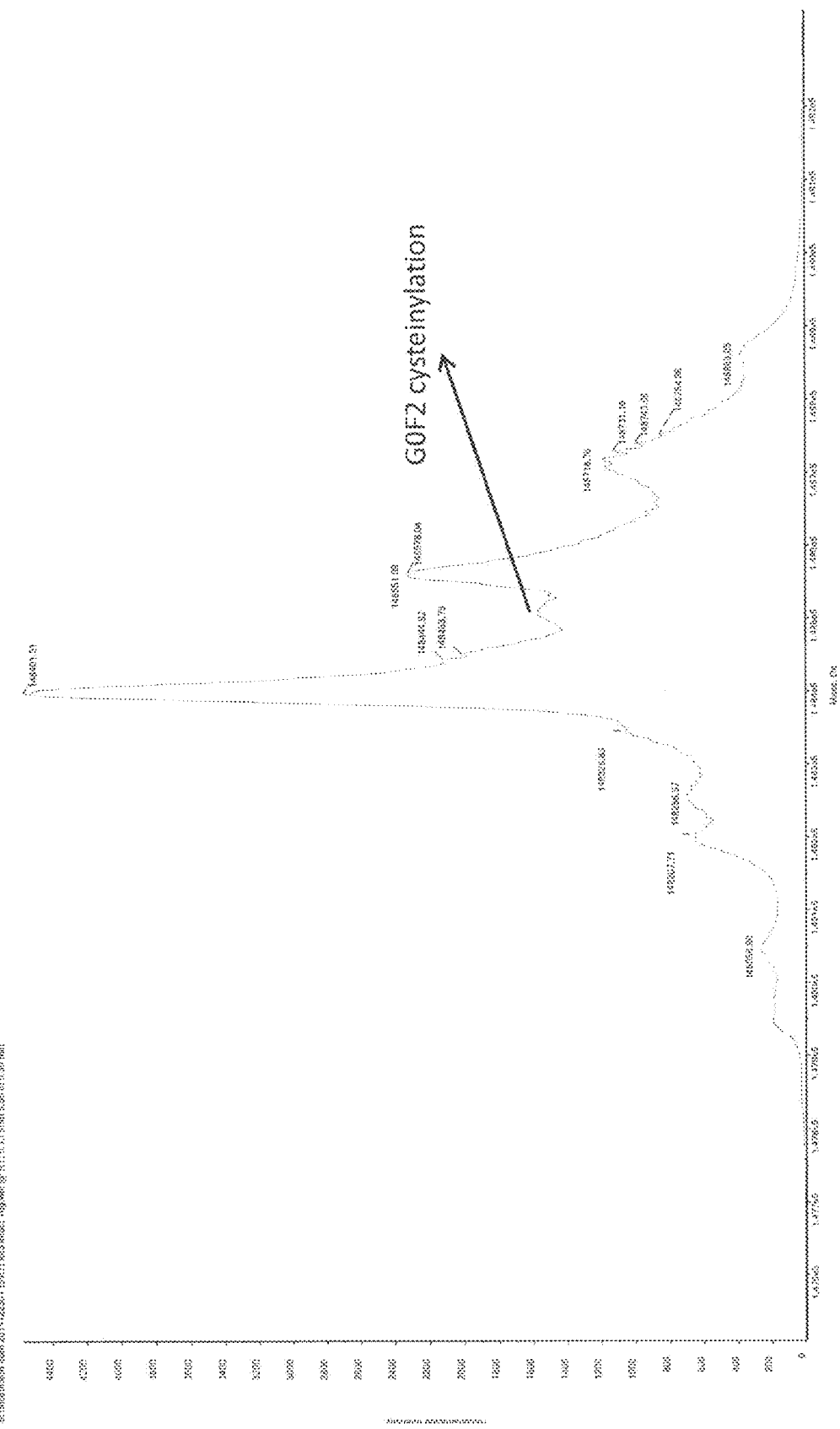
Fig. 14A (Cont.) LOT 3

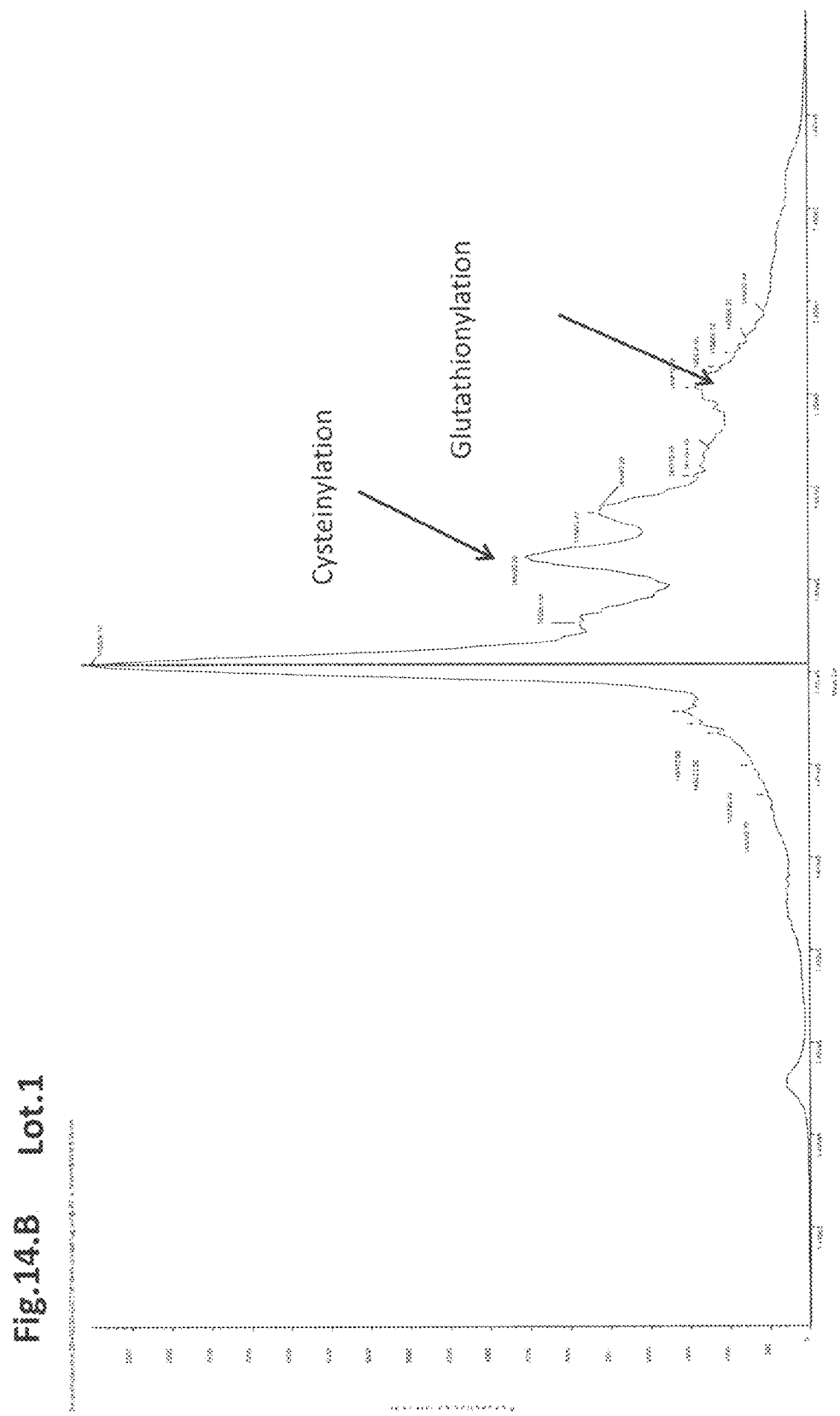

Fig. 14B (Cont.) Lot.2

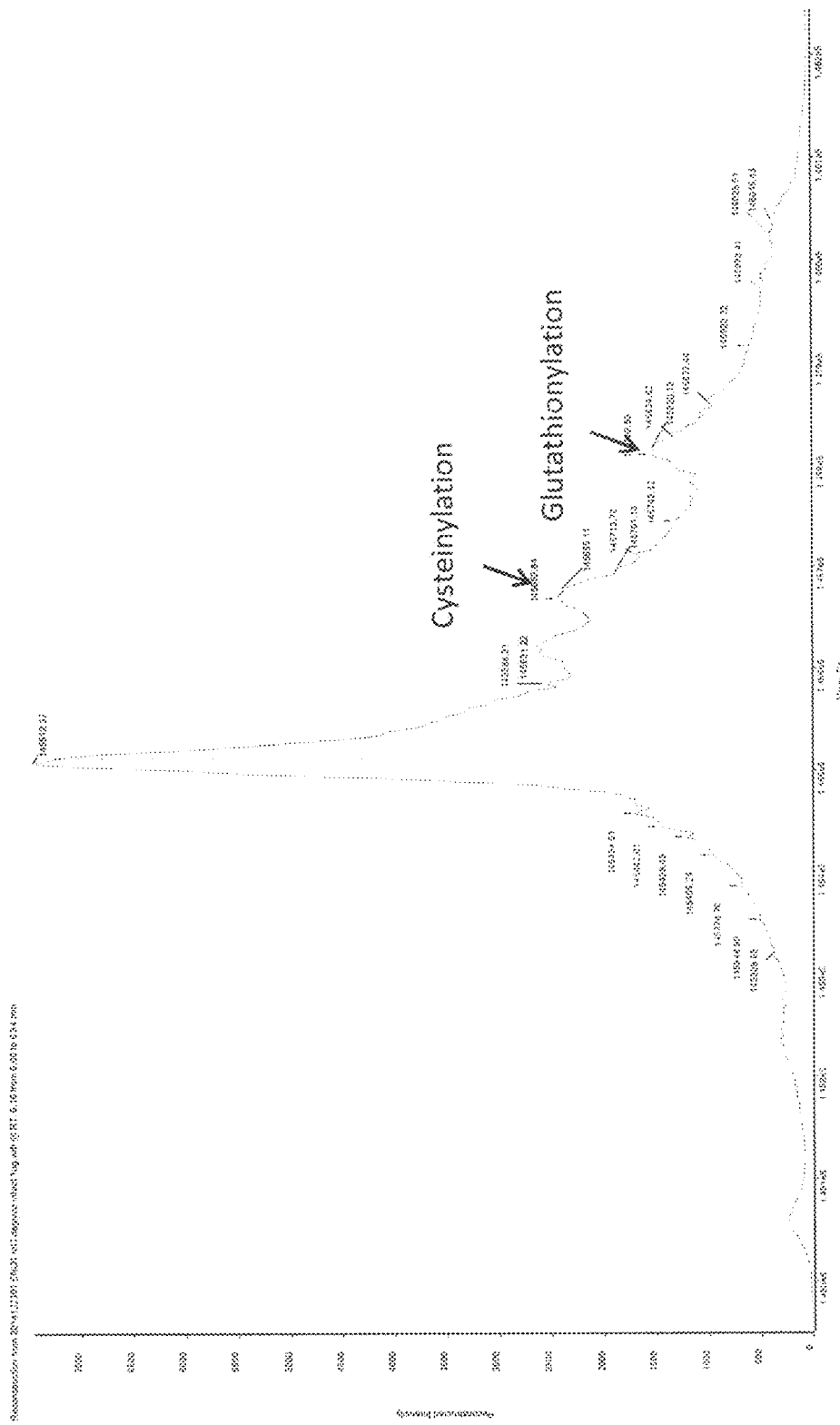
Fig. 14B (Cont.) Lot.3

Fig. 16

| 14D Rank | Clone ID | Day 14 Titer (mg/L) | Day 5 Titer (mg/L) |
|---|---|---|---|
| 1 | 41F9 | | 277.7 |
| 2 | 21B8 | | 188.5 |
| 3 | 31E2 | | 235.7 |
| 4 | 31E1 | | 265.7 |
| 5 | 11F11 | | 215.2 |
| 6 | 32G2 | | 190.7 |
| 7 | 22C3 | | 224.5 |
| 8 | 12C7 | | 177.4 |
| 9 | 42F12 | | 189.4 |
| 10 | 31C3 | | 194.0 |
| 11 | 21F10 | | 175.4 |
| 12 | 22B5 | | 186.2 |
| 13 | 42F2 | | 192.3 |
| 14 | 42C2 | | 169.7 |
| 15 | 11E3 | | 223.6 |
| 16 | 41E10 | | 214.0 |
| 17 | 42B11 | | 160.0 |
| 18 | 21A4 | | 161.4 |
| 19 | 11H7 | | 172.1 |
| 20 | 11A6 | | 172.3 |

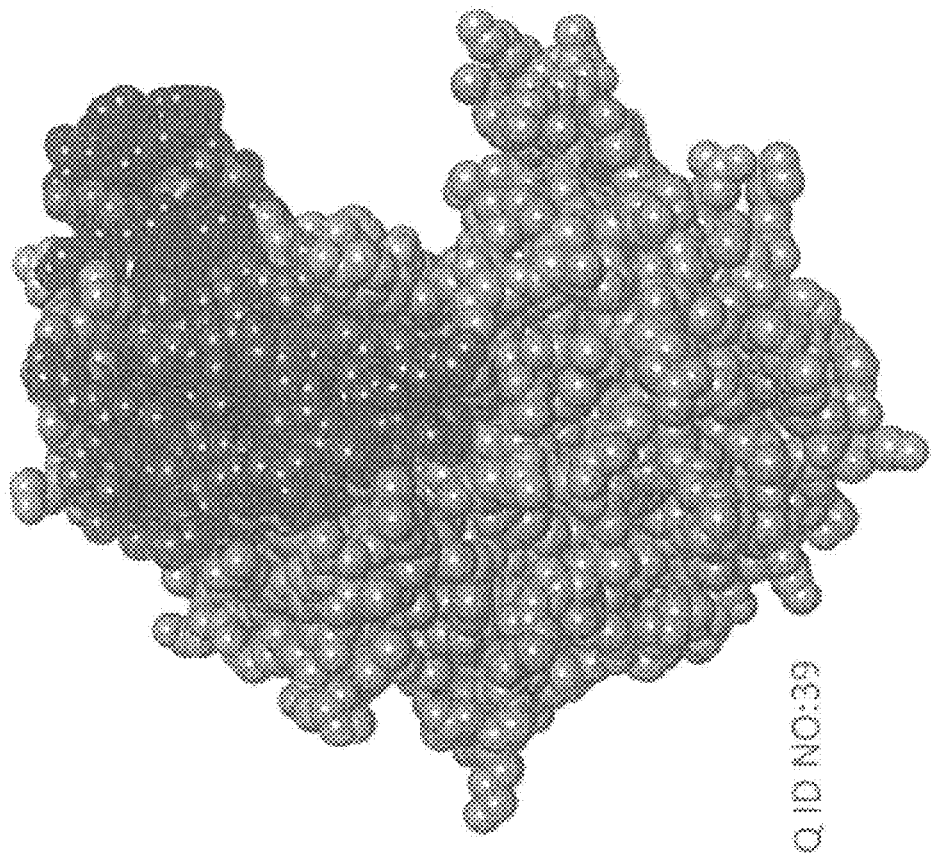
FIG. 19A prediction mutation points of human ENO1 and the EN10 Mab mAb
395QD

ANTIBODIES SPECIFIC TO ALPHA-ENOLASE AND USES THEREOF

FIELD OF THE INVENTION

The present invention relates to antibodies that bind specifically to the human alpha-enolase protein (ENO1). The present invention also relates to methods for treating an inflammatory disease or an immune disorder, or suppressing tumor growth and metastasis by administrating an anti-ENO1 antibody to a subject.

BACKGROUND OF INVENTION

Multiple sclerosis (MS) is a chronic inflammatory disease of the nervous system. In multiple sclerosis, myelin sheaths of nerve fibers are destroyed, i.e. the nerve fibers are demyelinated by auto antibodies. The symptoms of multiple sclerosis are relatively unspecific and, for example, relapse and remission of fatigue, numbness, gait and coordination problems, bowel/bladder dysfunction, cognitive dysfunction and pains. So far, causes and pathophysiology are poorly understood and may be caused by genetic background, vitamin D deficiency and geography. Early in the understanding of MS pathology, it is thought that myelin-specific CD4+T lymphocytes migrate from the blood to brain and spine, bind to antigenic peptides presented by antigen presenting cells (including microglial in the brain), clonally expand, attack and damage oligodendrocytes, and destroying myelin. Recent hypothesis suggests that myelin CD+4 T-cells are only involved in the early phase of MS. Circulation monocytes, induced by MCP-1 in CNS, are responsible for the mid and late phase of disease progression. Mice deficient in the chemokine receptor CCR2, of which ligand is MCP-1, are resistant to experimental autoimmune encephalomyelitis (EAE). When CCRC2 knock-out mice are transfused with different amounts of monocytes from EAE-induced CCRC2$^+$ mice, clinical scores of recipient mice are proportional to the amounts of transfused monocytes from the donor EAE mice. This result suggests that monocytes are very important for the EAE disease progression.

Rheumatoid arthritis (RA) is a chronicle inflammatory disease that affects patients' joints. Symptoms of RA include pains, swellings, stiffness, and deformations in joints. Patients always feel fever and fatigue. The etiology of RA is not fully understood. The disease starts from auto antibodies against patients' connective tissues, followed by infiltration of leukocytes including monocytes, macrophages and neutrophils. Then, lymphocytes erode and invade bones and soft tissues of joints.

In both diseases (MS and RA), data in the literatures support that inflammatory blood monocytes and macrophages are involved in the progression of both immune diseases.

Tumors result from aberrant, unrestrained proliferation of a single cell, and generating a clone of transformed cells. Cancer is characterized by tumor cells' autonomous growth and ability to metastasize to distant sites.

Tumor cells may express unique antigens that can be recognized by the immune system. Tumor-associated antigens include, but are not limited to, mutated oncogenes, mutated normal cellular proteins, aberrantly expressed cellular proteins, abnormal cell-surface proteins, and oncogenic viral proteins. The immune system views these tumor-associated antigens as non-self and can produce antibodies to eradicate these foreign antigen-bearing tumor cells, while sparing the healthy cells. Therefore, identification of immunogenic tumor-associated antigens may be used as targets for clinical prognostic or therapeutic applications in cancer treatment.

Certain malignancies may be identified by pleural effusion, which is excess fluid in the space between the lung and chest wall. Lung carcinoma, breast carcinoma, and lymphoma cause about 75% of all malignant pleural effusions. Malignant pleural effusion may be enriched with lymphocytic infiltrates and tumor cells. Tumor-associated immune complexes or autoantibodies, such as anti-p53, antinuclear, and anti-=c-Myc antibodies, have been found in effusion fluids and are associated with poor prognosis. Several lung tumor-associated antigens have also been identified in malignant effusion, including, cytokeratin 19 fragments, neuron-specific enolase (ENO2), squamous cell carcinoma antigen, and soluble HLA-I, etc.

Alpha-enolase (enolase-1, ENO1) is a multiple functional protein, which was first found as a key enzyme of the glycolysis pathways. Under normal conditions. ENO-1 is expressed in the cytosol. However, ENO1 is also found to express on the cell surfaces of many cancer cells as a plasminogen receptor and on activated hematopoietic cells, such as neutrophils, lymphocytes and monocytes. It is known that the up-regulation of plasminogen receptor proteins can induce a cascade response of the urokinase plasminogen activation system (uPAS) and results in extracellular matrix degradation. As a consequence, it results in increased metastasis of cancer cells and infiltration of immune cells. Inflammatory stimuli, for example LPS, up-regulate ENO1 cell-surface expression on human blood monocytes and U937 monocytic cells by post translational modification and translocation to cell surface.

It is believed the translocation of ENO1 is regulated by the MAP kinase signal transduction pathway. This implies that increases in the expression of ENO1 on cell surface may play an important role in the inflammatory diseases. Auto antibodies against ENO1 have been found in variable autoimmune and inflammatory diseases, including Lupus erythematousus, systemic sclerosis, Behcet disease, ulcerative, and Crohn's disease. It has been known that ENO1, by way of its plasminogen receptor activity, plays a key role in the disease progression of RA patients by increasing invasion activities of monocytes and macrophages.

In sum, monocytes with their up-regulated ENO1 expression on cell surfaces as plasminogen receptors to increase invasion activities are very important for the disease progression of MS, RA, and related immune disorders. Therefore, targeting ENO1 on the cell surface of monocytes has a good potential to treat inflammatory diseases, such as MS, RA, Crohn's disease, ulcerative colitis, and systemic Lupus crythematosus, or related immune disorders, such as chronic obstructive pulmonary disease (COPD), asthma, allergy, psoriasis, type 1 diabetes mellitus, artherosclerosis and osteoporosis.

The urokinase plasminogen activator system (uPAS) consists of the urokinase plasminogen activator (uPA), its cognate receptor (uPAR) and two specific inhibitors, the plasminogen activator inhibitor 1 (PAI-1) and plasminogen activator inhibitor 2 (PAI-2). Urokinase plasminogen activator converts plasminogen proenzyme into an active serine protease, plasmin. Plasmin is involved in a number of tissue remodeling processes, such as basement membrane (BM) and extracellular matrix (ECM) remodeling, which is required in tumor progression and metastasis. In addition, it has been shown that the uPAS may be involved in the neoplastic evolution, affecting tumor angiogenesis, malignant cell proliferation, adhesion and migration, intra-vascularization, and growth at the metastatic site.

Specifically, activation of plasminogen can result in extracellular matrix degradations, which in turn can lead to increased metastasis of cancer cells and infiltration of immune cells. In other words, ENO1 expression on cancer cell surfaces as a plasminogen receptor can increase invasion activities of the cancer cells. Therefore, ENO1 is also a potential target for cancer therapy.

SUMMARY OF INVENTION

Embodiments of the invention relate to antibodies or antigen-binding fragments thereof that specifically bind human ENO1, thereby inhibiting ligand (e.g., plasminogen) binding to ENO1. By inhibiting binding of plasminogen to ENO1, the antibodies of the invention can inhibit plasminogen activation.

In accordance with embodiments of the invention, an antibody or an antigen-binding fragment thereof can bind to an epitope on human ENO1 and inhibit ENO1 plasminogen receptor activity, wherein the epitope may be located in a region consisting of the sequence of $^{296}$FDQDDWGAWQK-FTASAGIQVVG DDLTVTNPKRIAKAVNEKS$^{336}$ (SEQ ID NO: 39) of human ENO1. In accordance with any of the above embodiments of the invention, the antibody or binding fragments thereof can bind to an epitope on human ENO1 and inhibit ENO1 plasminogen receptor activity, wherein the epitope may be located in a region consisting of the sequence of $^{296}$FDQDDWGAWQKFTA$^{309}$ (SEQ ID NO: 40) or $^{326}$KRIAKAVNEKS$^{336}$ (SEQ ID NO: 41) of human ENO1. In accordance with certain embodiments of the invention, the antibody may be a humanized antibody or a fully human antibody.

In accordance with some embodiments of the invention, an antibody or an antigen-binding fragment thereof that can bind human ENOprotein comprises (i) a light chain variable region (VL) comprising LCDR1 (RASENIYSYLT; SEQ ID NO: 6), LCDR2 (NAKTLPE; SEQ ID NO: 7) and LCDR3 (QHHYGTPYT; SEQ ID NO: 8), and (ii) a heavy chain variable region (VH) comprising HCDR1 (GYTFTS-CVMN; SEQ ID NO: 3), HCDR2 (YINPYNDGTKYNEK-FKG; SEQ ID NO: 4) and HCDR3 (EGFYYGNFDN; SEQ ID NO: 5).

In accordance with some embodiments of the invention, an antibody that can bind human ENO1 protein comprises a VL comprising amino acid residues 1-108 of SEQ ID NO: 2 or 9 and/or a VH comprising amino acid residues 1-120 of SEQ ID NO: 1, 10 or 11.

In accordance with some embodiments of the invention, a antibody or an antigen-binding fragment thereof that can bind human ENO1 protein comprises (i) a light chain variable region (VL) comprising LCDR1 (RASENIYSYLT; SEQ ID NO: 6), LCDR2 (NAKTLPE; SEQ ID NO: 7) and LCDR3 (QHHYGTPYT; SEQ ID NO: 8), and (ii) a heavy chain variable region (VH) comprising HCDR1 (GYTFTS-Xaa-VMN; SEQ ID NO: 50), HCDR2 (YINPYNDGT-KYNEKFKG; SEQ ID NO: 4) and HCDR3 (EGFYYG-NFDN; SEQ ID NO: 5).

In accordance with some embodiments of the invention, a antibody that can bind human ENO1 protein comprises a light chain variable region comprising the amino acid sequence set forth in SEQ ID NO:1 SEQ ID NO: 2 or 9 and/or a heavy chain variable region comprising the amino acid sequence set forth in SEQ ID NO: 1, 10 or 51.

Other embodiments of the invention relate to isolated nucleic acid molecules encoding any of the antibodies, or the antigen-binding fragments thereof, described herein, vectors having isolated nucleic acid molecules encoding the antibodies, or the antigen-binding fragments thereof or a host cell transformed with any of such nucleic acid molecules.

Other embodiments of the invention relate to pharmaceutical compositions comprising a therapeutically effective amount of an antibody or an antigen-binding fragment thereof that can bind human ENO1 protein, and a pharmaceutically acceptable carrier.

Still further embodiments of the invention relate to a method for effectively treating a subject (e.g., human or non-human animal) suffering from a ENO1 protein-related disease or disorder. The method may include selecting a subject in need thereof and administering to the subject a therapeutically effective amount of an antibody (which may be a humanized or a fully human antibody) or a fragement thereof that specifically binds to ENO1 protein.

In accordance with certain embodiments of the invention, the the human ENO1 protein-related disease or disorder may be any condition arising from aberrant activation or expression of human ENO1 protein. Examples of such diseases include where human ENO1 protein aberrantly interacts with its ligands, thereby altering cell-adhesion or cell signaling properties. This alteration in cell adhesion or cell signaling properties can result in neoplastic diseases and/or inflammatory or immune diseases.

For example, a human ENO1 protein-related disease may be an inflammatory disease or an immune disorder, such as multiple sclerosis, rheumatoid arthritis, Crohn's disease, ulcerative colitis, systemic Lupus erythematosus, or relative immune disorders, such as chronic obstructive pulmonary disease (COPD), asthma, allergy, psoriasis, type 1 diabetes mellitus, atherosclerosis and osteoporosis; or a neoplastic disease, such as lung, breast, pancreas, liver, colorectal, and prostate cancers.

Some embodiments of the invention relate to methods for assaying the level of human ENO1 protein in a patient or a patient sample. A method of the invention comprises contacting a humanized anti-ENO1 antibody with a biological sample from a patient, and detecting the level of binding between said antibody and human ENO1 protein in said sample. In more specific embodiments, the biological sample is blood or plasma or tissue samples.

BRIEF DESCRIPTION OF THE DRAWINGS

FIG. 5A depicts the variable heavy chain region amino acid sequence of EN10 mAb (SEQ ID NO: 1). The framework regions (FR1, FR2, FR3, and FR4) and CDRs (HCDR1, HCDR2, and HCDR3) are indicated. Cloning the EN10 was performed as described in Example 5.

FIG. 5B depicts the variable light chain region amino acid sequence of EN10 mAb (SEQ ID NO: 2). The framework regions (FR1, FR2, FR3, and FR4) and CDRs (LCDR1, LCDR2, and LCDR3) are indicated. Cloning the EN10 mAb was performed as described in Example 5.

FIG. 6A shows the sequence analysis made for humanization of the VL (SEQ ID NO:9) and VH (SEQ ID NO:10) sequences of hum ENO10mAb 4D5. In the first line showing with under the residue numbering according the Kabat scheme, the mask is shown with underling, and the Kabat CDRs are shown in under lines. To determine the frame works of VL and VH of humEN10 mAb 4D5 were performed as described in Example 6.

FIG. 6B shows the sequence analysis made for humanization of the VL (SEQ ID NO:9) and VH (SEQ ID NO: 11) sequences of hum ENO10mAb IMGT. In the first line showing with under the residue numbering according the Kabat scheme, the mask is shown with underling, and the Kabat CDRs are shown in under lines. To determine the frame works of VL and VH of humEN10 mAb IMGT were performed as described in Example 6.

FIGS. 13A and B show the sequence analysis made for the codon optimization of the VL (SEQ ID NOs:14 and 15) and VH (SEQ ID NOs:16 and 17) sequences of humEN10 mAb IMGT expressed in the CHOS cell line. Detailed procedures were performed as described in Example 13.

FIG. 13D depicts the productivity of top 15 CHOS stable clones which expressed humEN10 IMGT mAb antibody in days 5 and day 14. Detail procedures were performed as described in Example 13. The production rates ranges from 155 minigram/titer to 91.3 minigram/liter on the day 5 and from 358.7 minigram/titer to 247.5 minigram/liter on the day 15.

FIG. 14A shows the size exclusion HPLC and Mass spectrum analysis of 3 batches of humEN10 mAb IMGT antibody. Detailed procedures were performed as described in Example 14. Our data show that clone 6C6 expresses hum EN10 mAb IMGT with different percentages of cysteinylated antibody in three lots.

FIG. 14B shows the size exclusion HPLC and Mass spectrum analysis of 3 batches of deglycosylated humEN10 mAb IMGT antibody. Detailed procedures were performed as described in Example 14. Our data show that clone 6C6 expresses hum EN10 mAb IMGT with different percentages of cysteinylated antibody. The detail composition of gluta-thionylation and cysteinylation of 3 batches of deglycosy-lated humEN10 mAb IMGT antibodies was shown in Table III.

Detailed procedures of antibody expression, purification and KD analysis were performed as described in Example 15. The results show that KD value of hum EN10 mAb IMGT is not significantly different from those of EN10.4 and EN10.5 mAbs.

FIG. 16, shows the productivities of top 20 CHOS stable clones, which expressed mAb EN10.5, antibody. Detailed procedures were performed as described in Example 16. Our data show that after the serine mutation in the amino acid number 32 of HCDR1 (SEQ ID NO.3) and single colony selection, the production rates of these 20 top clones are over 344 g/L/14 days.

Figure 17A:
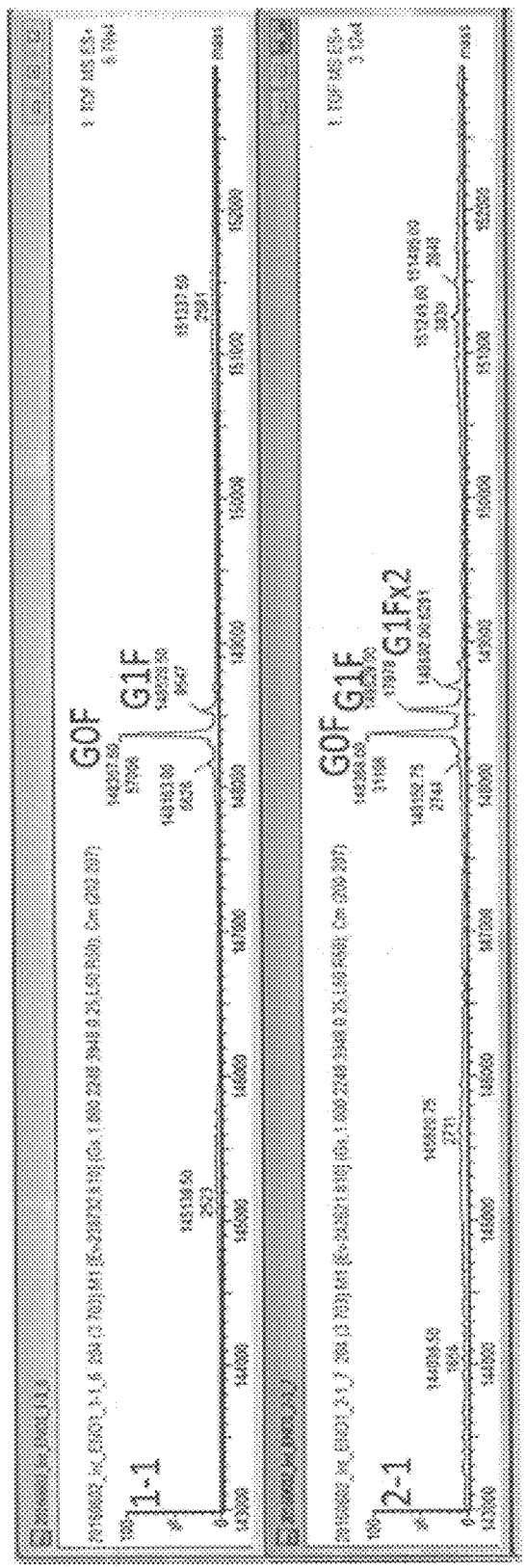

FIG. 17A shows the results of size exclusion HPLC and Mass spectrum analysis of 2 batches of EN10.5 antibody. Detailed procedures were performed as described in Example 17. Our data show that clone EN10.5 expresses hum EN10 mAb IMGT without cysteinylated antibody.

Figure 17B:
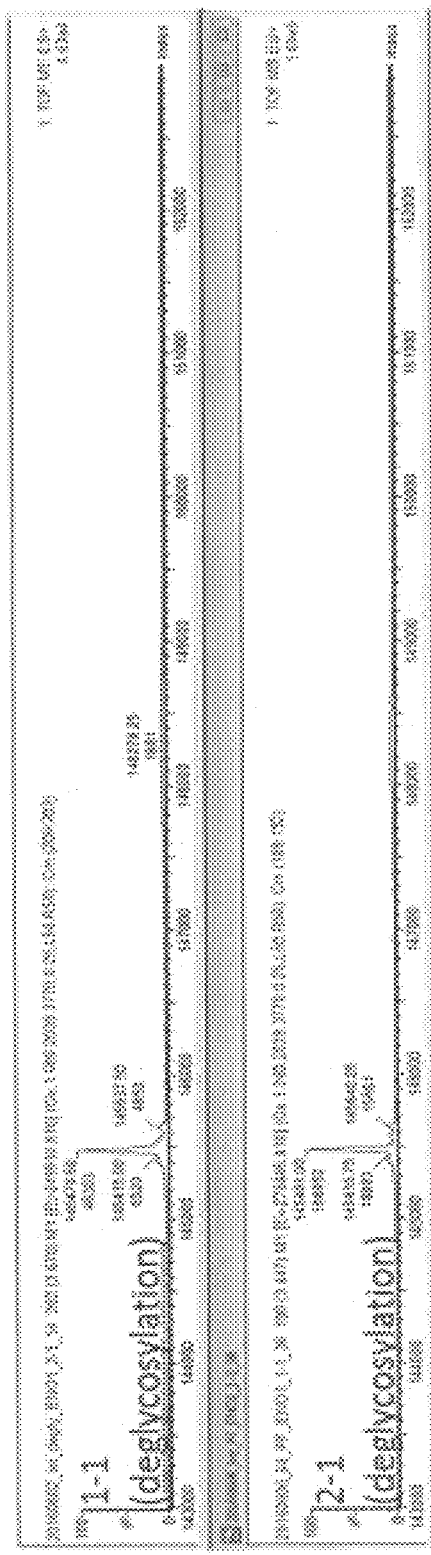

FIG. 17B, shows the results of size exclusion HPLC and Mass spectrum analysis of 2 batches of deglycosylated EN10.5 antibody. Detailed procedures were performed as described in Example 17. Our data show that clone EN10.5 expresses hum EN10 mAb IMGT without cysteinylated antibody.

Figure 18A:
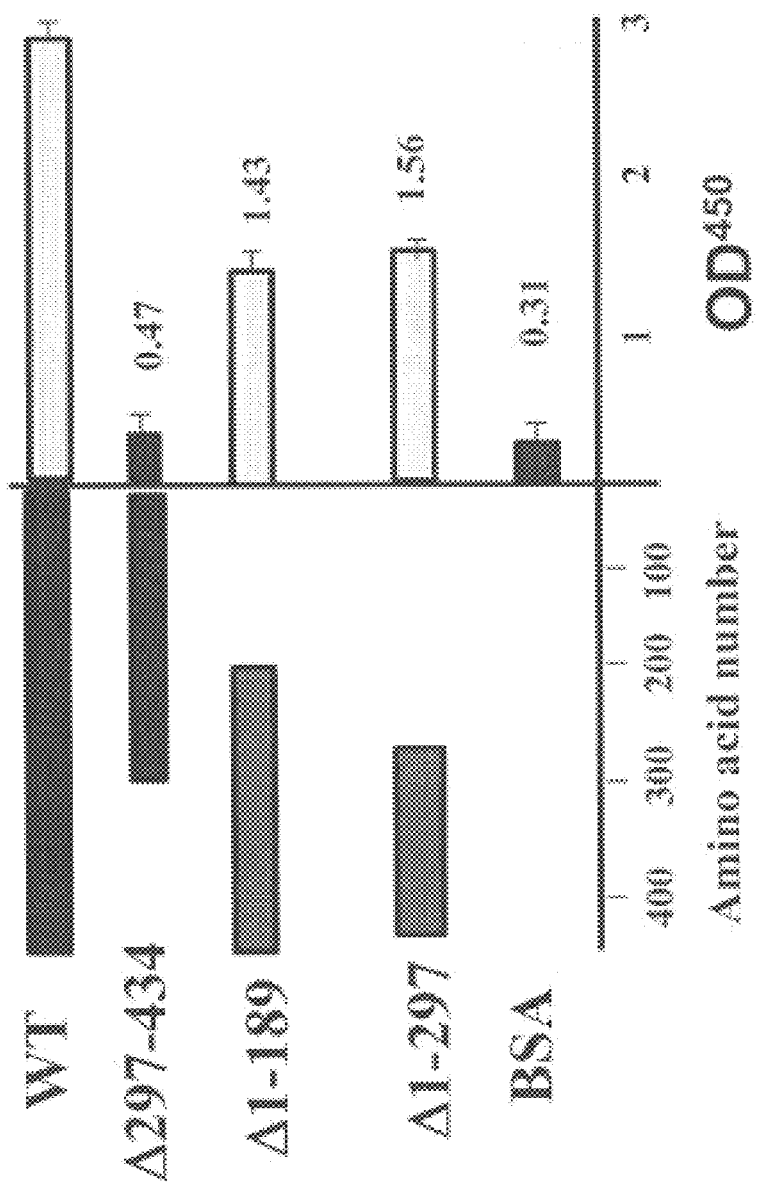

FIG. 18A shows the EN10 mAb binding activities of deletion mutants of ENO1. The binding epitope of EN10 mAb is located between the amino residue number 293 and 434 of human ENO1 protein. The large portion deletion of ENO1 to determine the binding region of EN10 mAb was performed as described in Example 18.

Figure 18B:
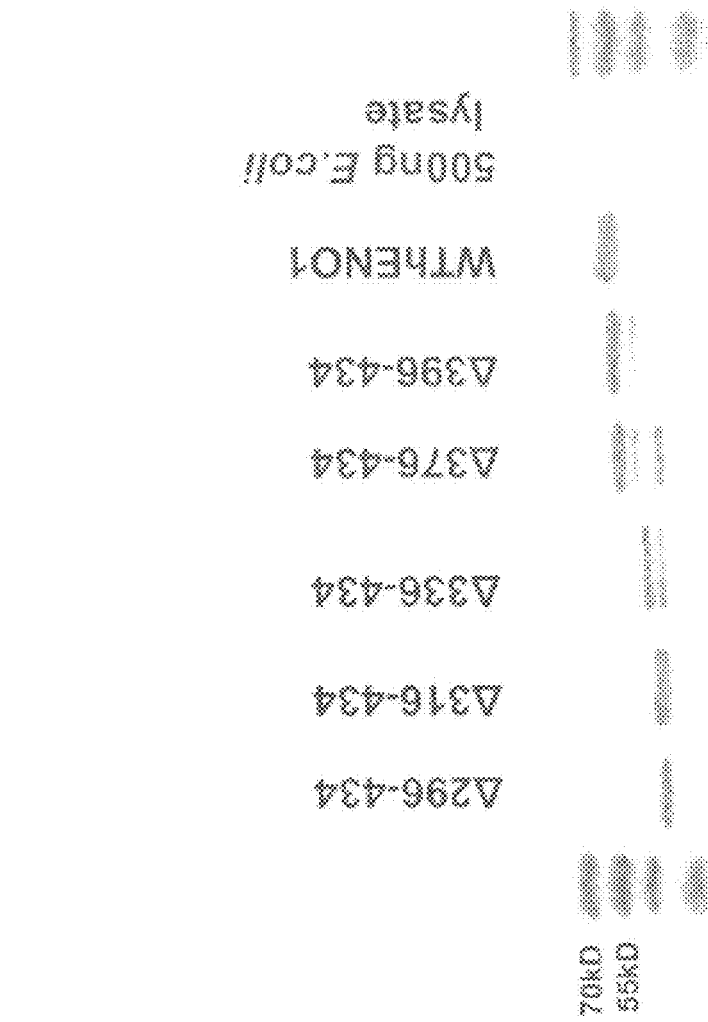

FIG. 18B shows the 12% SDS PAGE of 6 C-terminal deletion mutant proteins of ENO1 purified from *E. coli*. The detailed procedures for the purification of ENO1 deletion mutants are described in Example 18.

Figure 18C:
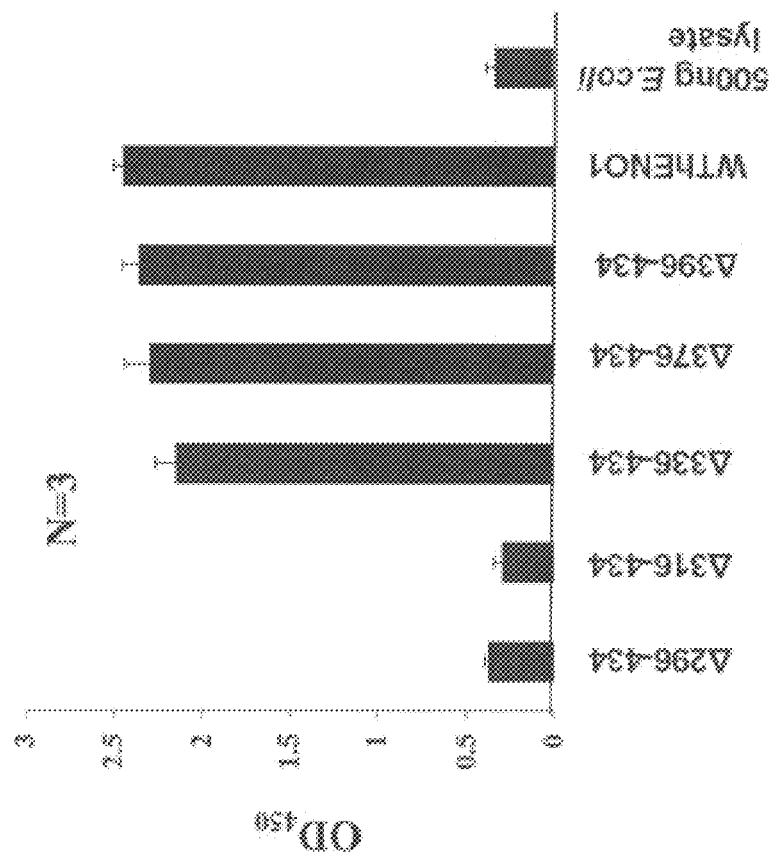

FIG. 18C shows the EN10 mAb binding activities of 6 C-terminal deletion mutants of ENO1. The binding epitope of EN10 mAb is located between amino residue number 296 and 336 of human ENO1 protein. The large portion deletion of ENO1 to determine the binding region of EN10 mAb was performed as described in Example 18.

FIG. 19A depicts the crystal structure and surface-expose amino acid residues between amino number 296 and 336 of human ENO1. The structure prediction was described in Example 19.

Figure 19B:
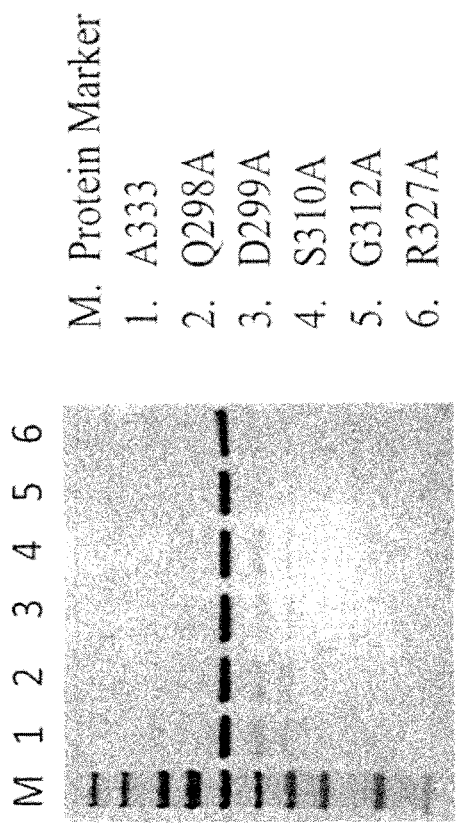

FIG. 19B shows the 12% SDS PAGE of 6 alanine scanning mutant proteins of ENO1 purified in *E. coli*. The detailed procedures for the purification of ENO1 mutation proteins are described in Example 19.

Figure 19C:
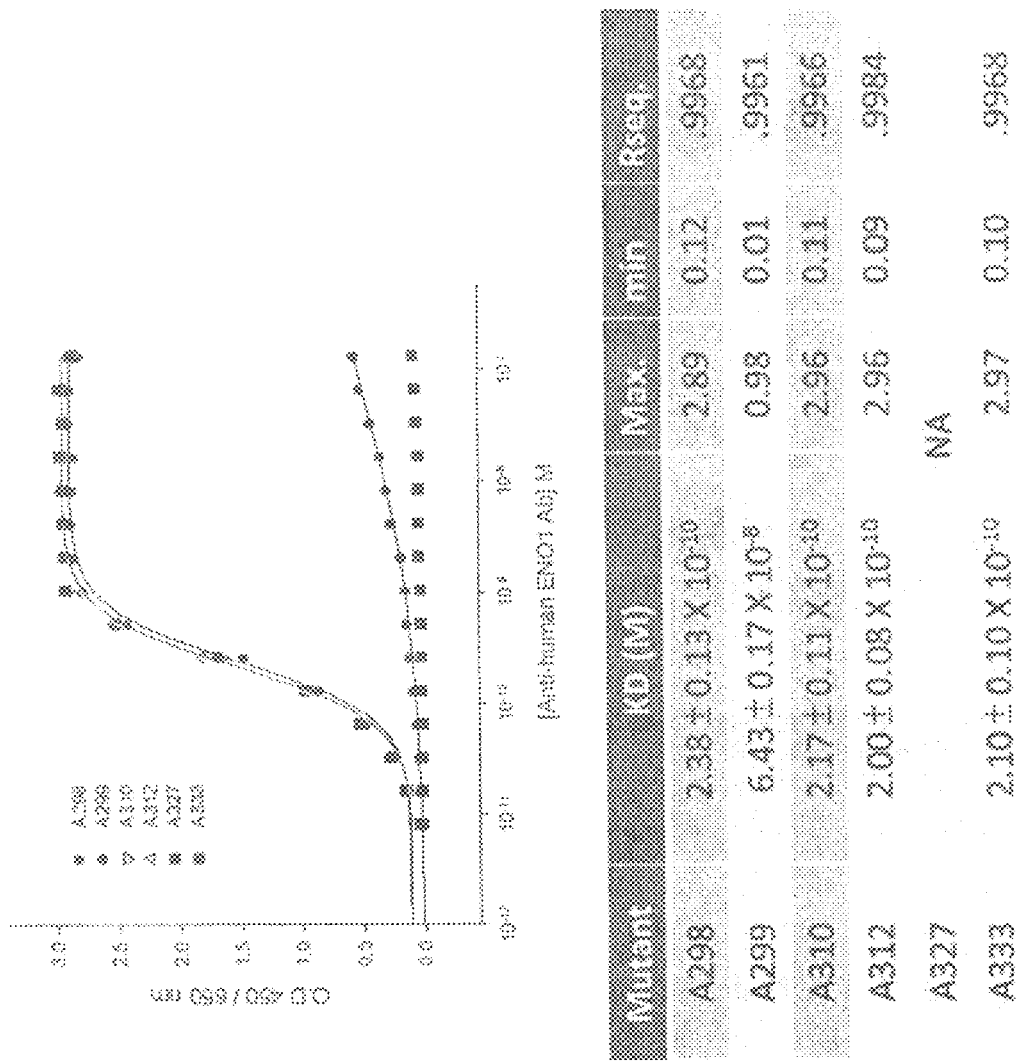

FIG. 19C shows the ENO1 binding ELISA and KD values of 6 alanine scanning mutants against EN10.5 mAb. The result suggests that amino acid sequences of $Asp^{299}$ and $Arg^{327}$ located between amino residue number 296 and 336 of human ENO1 are involved in EN10 mAb binding. The alanine scanning was performed as described in Example 19.

DETAILED DESCRIPTION OF THE INVENTION

Unless otherwise defined, scientific and technical terms used herein shall have the meanings that are commonly understood by those of ordinary skill in the art. Furthermore, unless otherwise required by context, singular terms shall include pluralities and plural terms shall include the singular. Generally, nomenclatures used in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular Cloning: A Laboratory Manual (3rd ed., Cold Spring Harbor Laboratory Press, Cold Spring Harbor. N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings: The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

An antagonist may be a polypeptide, nucleic acid, carbohydrate, lipid, small molecular weight compound, an oligonucleotide, an oligopeptide, interference RNA (RNAi), antisense, a recombinant protein, an antibody, or conjugates or fusion proteins thereof. For a review of RNAi, see Milhavet O, Gary D S. Mattson M P. (Pharmacol Rev. 2003 December, 55(4):629-48. Review.) and for antisense approach, see Opalinska J B, Gewirtz A M. (Sci STKE. 2003 Oct. 28; 2003 (206): pe47).

The human ENO1 plasminogen receptor is known to a person skilled in the art (see. GenBank: AAH50642.1 on the Website of the National Institute of Health). This receptor is a plasminogen receptor and exists in two different splicing variants in humans, ENO1 and Myc binding protein. ENO1 is also known as human ENO1, alpha-Enolase. or ENO-1 gene.

The corresponding orthologs of ENO1 from several other species are also known and can easily be determined by a person skilled in the art, for example, by means of sequence searches starting from the human ENO1. In accordance with embodiments of the invention, the term "ENO1" refers to both human and animal (e.g., pets and livestock) ENO1 proteins.

As used herein, the term "antibody" refers generally and broadly to immunoglobulins, autoantibodies, monoclonal antibodies, and polyclonal antibodies, as well as active fragments thereof. The fragment may be active in that it binds to the cognate antigen, or it may be active in that it is biologically functional. The antibodies of the invention may be chimeric, humanized, or human, using techniques known in the art. The fragments of an antibody may include, but are not limited to, an antibody Fab fragment. F(ab')2, Fv fragment or Fc fragment from a cleaved antibody, a scFv-Fc fragment, a minibody, a or an scFv.

As used herein, the term "antibody" refers generally and broadly to immunoglobulins, autoantibodies, monoclonal antibodies, and polyclonal antibodies, as well as active fragments thereof. The fragment may be active in that it binds to the cognate antigen, or it may be active in that it is biologically functional. The antibodies of the invention may be chimeric, humanized, or human, using techniques known in the art.

As used herein, the term "monoclonal antibody" refers to antibodies that are chemically and immunologically homogeneous, generally produced by hybridomas. See A Laboratory Manual. Harlow and Lane, eds., Cold Spring Harbor. N.Y. (1988).

As used herein, the term "polyclonal antibody" refers to antibodies that are produced by more than one clone of antibody-synthesizing plasma cells (B-lymphocytes) in response to the same antigen. They are generally produced by the animal after it is immunized with the antigen.

As used herein, the term "chimeric antibody" refers to antibodies that contain sequences from more than one source. For example, such antibodies may contain sequences from non-human sources that are then modified by introducing human sequences.

As used herein, the term "humanized antibody" refers to an antibody in which minimal portions of a non-human antibody are introduced into an otherwise human antibody.

As used herein, the term "human antibody" refers to an antibody in which substantially every part of the protein is substantially non-immunogenic in humans, with only minor sequence changes or variations.

As used herein, the term "alpha-enolase specific antibody" refers to an antibody that has a high specificity for mammalian ENO1, but not to ENO2 or ENO3.

The term "neutralizing" when referring to a targeted binding agent, such as an antibody, relates to the ability of said targeted binding agent to eliminate, or significantly reduce, the activity of a target antigen. Accordingly, a "neutralizing" ENO1 antibody is capable of eliminating or significantly reducing the activity of ENO1. A neutralizing ENO1 antibody may, for example, act by blocking the binding of ENO1 to the plasminogen. By blocking this binding, the plasminogen mediated cell dissociation is significantly, or completely, eliminated. Ideally, a neutralizing antibody against ENO1 enhances cell adhesion.

The term "isolated polynucleotide" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide that it is not linked to in nature. In addition, isolated polynucleotides preferably do not occur in nature as part of a larger sequence.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA heteroduplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded. e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoranilidate, phosphoroamidate, and the like. See e.g., LaPlanche, et al., Nucl. Acids Res. 14:9081 (1986); Stec, et al., J. Am. Chem. Soc. 106:6077 (1984); Stein, et al., Nucl. Acids Res. 16:3209 (1988); Zon, et al., Anti-Cancer Drug Design 6:539 (1991); Zon, et al., Oligonucleotides and Analogues: A Practical Approach, pp. 87-108 (F. Eckstein. Ed., Oxford University Press, Oxford England (1991)); Stec, et al., U.S. Pat. No. 5,151,510; Uhlmann and Peyman Chemical Reviews 90:543 (1990), the disclosures of which are hereby incorporated by reference. An oligonucleotide can include a label for detection, if desired.

The term "CDR region" or "CDR" is intended to indicate the hypervariable regions of the heavy or light chains of the immunoglobulin as defined by Kabat, et al., 1991 (Kabat, E. A. et al., (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids, although the longest size known is 26. CDR length may also vary according to the length that can be accommodated by the particular underlying framework. Functionally, HCDR3 plays a role in part in the determination of the specificity of the antibody (Segal, et al., PNAS, 71:4298-4302, 1974, Amit, et al., Science, 233:747-753, 1986, Chothia, et al., J. Mol. Biol., 196:901-917, 1987, Chothia, et al., Nature, 342:877-883, 1989, Caton, et al., J. Immunol., 144:1965-1968, 1990, Sharon, et al., PNAS, 87:4814-4817, 1990, Sharon, et al., J. Immunol. 144:4863-4869, 1990, Kabat, et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3 (LCDR refers to a variable heavy chain CDR), and a set of LCDRs refers to LCDR1, LCDR2 and LCDR3 (LCDR refers to a variable light chain CDR). Unless otherwise stated, a "set of CDRs" includes HCDRs and LCDRs.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity.

The terms "substantial identity" or "substantially identical" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2.sup.nd Edition. E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine. N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least about 75%, more preferably at least 80%, 90%, 95%, and most preferably about 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site.

Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxyl-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., (1991) Science 253:164. Thus, the foregoing examples demonstrate that those of skill in the art can recognize sequence motifs and structural conformations that may be used to define structural and functional domains in accordance with the antibodies described herein.

A further aspect of the invention is a targeting binding agent or an antibody molecule comprising a VH domain that has at least about 60, 70, 80, 85, 90, 95, 98 or about 99% amino acid sequence identity with a VH domain of any of antibodies shown in sequences 1, the appended sequence listing, an antibody described herein, or with an HCDR (e.g., HCDR1, HCDR2, or HCDR3) shown in sequences 1. The targeting binding agent or antibody molecule may optionally also comprise a VL domain that has at least about 60, 70, 80, 85, 90, 95, 98 or about 99% amino acid sequence identity with a VL domain any of antibodies shown in sequences 2, the appended sequence listing, an antibody described herein, or with an LCDR (e.g., LCDR1, LCDR2, or LCDR3) shown in sequences 2. Algorithms that can be used to calculate % identity of two amino acid sequences comprise e.g. BLAST (Altschul et al., (1990) J. Mol. Biol. 215: 405-410), FASTA (Pearson and Lipman (1988) PNAS USA 85: 2444-2448), or the Smith-Waterman algorithm (Smith and Waterman (1981) J. Mol. Biol. 147: 195-197), e.g. employing default parameters. In some embodiments, the targeting binding agent or antibody that shares amino acid sequence identity as describes above, exhibits substantially the same activity as the antibodies referenced. For instance, substantially the same activity comprises at least one activity that differed from the activity of the references antibodies by no more that about 50%, 40%, 30%, 20%, 10%, 5%, 2%, 1% or less.

An antigen binding site is generally formed by the variable heavy (VH) and variable light (VL) immunoglobulin domains, with the antigen-binding interface formed by six surface polypeptide loops, termed complementarity determining regions (CDRs). There are three CDRs in each VH (HCDR1, HCDR2, HCDR3) and in each VL (LCDR1, LCDR2, LCDR3), together with framework regions (FRs).

Typically, a VH domain is paired with a VL domain to provide an antibody antigen-binding site, although a VH or VL domain alone may be used to bind antigen. The VH domain (e.g. from sequences 1) may be paired with the VL domain (e.g. from sequences 2), so that an antibody antigen-binding site is formed comprising both the VH and VL domains. Analogous embodiments are provided for the other VH and VL domains disclosed herein. In other embodiments, VH chains in sequences 1 are paired with a heterologous VL domain. Light-chain promiscuity is well established in the art. Again, analogous embodiments are provided by the invention for the other VH and VL domains disclosed herein. Thus, the VH of the parent or of any of antibodies chain on sequences 2 may be paired with the VL of the parent or of any of antibodies on sequences 1, and 2 or other antibody.

An antigen binding site may comprise a set of H and/or L CDRs of the parent antibody or any of antibodies in sequences 1 and 2 with as many as twenty, sixteen, ten, nine or fewer, e.g. one, two, three, four or five, amino acid additions, substitutions, deletions, and/or insertions within the disclosed set of H and/or L CDRs. Such modifications may potentially be made at any residue within the set of CDRs.

Preferred amino acid substitutions are those which: (1) reduce susceptibility to proteolysis, (2) reduce susceptibility to oxidation, (3) alter binding affinity for forming protein complexes. (4) alter binding affinities, and (4) confer or modify other physicochemical or functional properties of such analogs. Analogs can include various mutant proteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing. New York, N.Y. (1991)); and Thornton et at. Nature 354:105 (1991), which are each incorporated herein by reference.

A further aspect of the invention is an antibody molecule comprising a VH domain that has at least about 60, 70, 80, 85, 90, 95, 98 or about 99% amino acid sequence identity with a VH domain of any of antibodies listed in sequences 1, the appended sequence listing or described herein, or with an HCDR (e.g., HCDR1, HCDR2, or HCDR3) shown in sequences 1. The antibody molecule may optionally also comprise a VL domain that has at least 60, 70, 80, 85, 90, 95, 98 or 99% amino acid sequence identity with a VL domain of any of the antibodies shown in sequences 2, the appended sequence listing or described herein, or with an LCDR (e.g., LCDR1, LCDR2, or LCDR3) shown in sequences 2. Algorithms that can be used to calculate % identity of two amino acid sequences comprise e.g. BLAST (Altschul et al., (1990) J. Mol. Biol. 215: 405-410). FASTA (Pearson and Lipman (1988) PNAS USA 85: 2444-2448), or the Smith-Waterman algorithm (Smith and Waterman (1981) J. Mol. Biol. 147: 195-197). e.g. employing default parameters.

A further aspect of the invention is an antibody molecule comprising a VH domain that has at least about 60, 70, 80, 85, 90, 95, 98 or about 99% amino acid sequence identity with a VH domain of any of antibodies listed in sequences 1, or with an HCDR (e.g., HCDR1, HCDR2, or HCDR3) shown in sequences 1. The antibody molecule may optionally also comprise a VL domain that has at least 60, 70, 80, 85, 90, 95, 98 or 99% amino acid sequence identity with a VL domain of any of the antibodies shown in sequences 2, the appended sequence listing or described herein, or with an LCDR (e.g., LCDR1, LCDR2, or LCDR3) shown in sequences 2.

Variants of the VH and VL domains and CDRs of the present invention, including those for which amino acid sequences are set out herein, and which can be employed in targeting agents and antibodies for human ENO1 protein can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralization of an antigen activity relative to known antibodies which are specific for the antigen if the activity is known; specified competitive ability with a known antibody or ligand to the antigen at a specific molar ratio; ability to immunoprecipitate complex; ability to bind to a specified epitope; linear epitope, e.g. peptide sequence identified using peptide-binding scan as described herein, e.g. using peptides screened in linear and/or constrained conformation; conformational epitope, formed by non-continuous residues; ability to modulate a new biological activity of human ENO1 protein or downstream molecule. Such methods are also provided herein.

A further aspect of the present invention relates to a targeted binding agent (i.e. an antibody) including those for which amino acid sequences that binds to the epitope peptide comprising amino acid sequence that has at least about 60, 70, 80, 85, 90, or about 92% amino acid sequence identity listed in sequences 9 or 10 on human ENO1 protein and can be used to treat an human ENO1 protein disease or disorder. A human ENO1 protein-related disease or disorder can be any condition arising due to the aberrant activation or expression of human ENO1 protein. In one example, the human ENO1 protein-related disease is a neoplastic disease such as non-small cell lung cancer, hepatocellular (liver) carcinoma, gastric (stomach) cancer, breast cancer, pancreatic duct adenocarcinoma.

Variants of antibody molecules disclosed herein may be produced and used in the present invention. Following the lead of computational chemistry in applying multivariate data analysis techniques to the structure/property-activity relationships (Wold, et al., Multivariate data analysis in chemistry. Chemometrics—Mathematics and Statistics in Chemistry (Ed.: B. Kowalski). D. Reidel Publishing Company, Dordrecht, Holland, 1984) quantitative activity-property relationships of antibodies can be derived using well-known mathematical techniques, such as statistical regression, pattern recognition and classification (Norman et al., Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek, Principles of Multivariate Analysis: A User's Perspective (Oxford Statistical Science Series. No 22 (Paper)). Oxford University Press; (December 2000); Witten, Ian H. & Frank, Eibe, Data Mining: Practical Machine Learning Tools and Techniques with Java Implementations. Morgan Kaufmann; (Oct. 11, 1999); Denison David G. T. (Editor). Christopher C. Holmes. Bani K. Mallick, Adrian F. M. Smith. Bayesian Methods for Nonlinear Classification and Regression (Wiley Series in Probability and Statistics). John Wiley & Sons; (July 2002); Ghose, Amp K. & Viswanadhan, Vellarkad N. Combinatorial Library Design and Evaluation Principles, Software. Tools. and Applications in Drug Discovery). The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule using any freely available or commercial package, such as WAM. A protein visualization and analysis software package, such as Insight II (Accelrys, Inc.) or Deep View may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and/or binding agents generally are available in the art. Variant sequences may be made, with substitutions that may or may not be predicted to have a minimal or beneficial effect on activity, and tested for ability to bind and/or neutralize and/or for any other desired property.

Variable domain amino acid sequence variants of any of the VH and VL domains whose sequences are specifically disclosed herein may be employed in accordance with the present invention, as discussed.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least about 5, 6, 8 or 10 amino acids long, preferably at least about 14 amino acids long, more preferably at least about 20 amino acids long, usually at least about 50 amino acids long, and even more preferably at least about 70 amino acids long. The term "analog" as used herein refers to polypeptides which are comprised of a segment of at least about 25 amino acids that has substantial identity to a portion of a deduced amino acid sequence and which has at least one of the following properties: (1) specific binding to human ENO1 protein under suitable binding conditions, (2) ability to block appropriate ligand ENO1 protein binding, or (3) ability to inhibit ENO1 protein activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

As used herein, the term "antibody" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site.

As used herein, a "targeted binding agent" is an agent, e.g. antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. As described below, a targeted binding agent may comprise at least one antigen binding domain of an antibody, wherein said domain is fused or contained within a heterologous protein.

"Binding fragments" of an antibody are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and disulfide stabilized variable region (dsFv).

It has been shown that fragments of a whole antibody can perform the function of binding antigens. Examples of binding fragments are (Ward. E. S. et al., (1989) Nature 341, 544-546) the Fab fragment consisting of VL, VH, CL and CH1 domains; (McCafferty et al., (1990) Nature, 348, 552-554) the Fd fragment consisting of the VH and CH1 domains; (Holt et al., (2003) Trends in Biotechnology 21, 484-490) the Fv fragment consisting of the VL and VH domains of a single antibody; (iv) the dAb fragment (Ward. E. S. et al., Nature 341, 544-546 (1989). McCafferty et al., (1990) Nature, 348, 552-554. Holt et al., (2003) Trends in Biotechnology 21, 484-490], which consists of a VH or a VL domain; (v) isolated CDR regions; (vi) F(ab').sub.2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., (1988) Science, 242, 423-426, Huston et al., (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al., Proc. Natl. Acad. Sci. USA 90 6444-6448). Fv, scFv or diabody molecules may be stabilized by the incorporation of disulphide bridges linking the VH and VL domains (Reiter, Y. et al., Nature Biotech, 14, 1239-1245, 1996). Minibodies comprising a scFv joined to a CH3 domain may also be made (Hu, S. et al., (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is $\leq 1$ micro M, preferably $\leq 100$ nM, and most preferably $\leq 10$ nM.

The term "agent" is used herein to denote a chemical compound, a mixture of chemical compounds, a biological macromolecule, or an extract made from biological materials.

"Active" or "activity" in regard to an ENO1 polypeptide refers to a portion of an ENO1 polypeptide that has a biological or an immunological activity of a native ENO1 polypeptide. "Biological" when used herein refers to a biological function that results from the activity of the native ENO1 polypeptide. A preferred ENO1 biological activity includes, for example, ENO1 induced the plasminogen activity.

"Subject" when used herein refers to any animal. Preferably, the subject is human or non-human mammal. Preferably, the subject is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a $F(ab')_2$ fragment in which the two arms of the antibody molecule remain linked and comprise two-antigen binding sites. The $F(ab')_2$ fragment has the ability to crosslink antigen.

"Fv" when used herein refers to the minimum fragment of an antibody that retains both antigen-recognition and antigen-binding sites. "Fab" when used herein refers to a fragment of an antibody that comprises the constant domain of the light chain and the CH1 domain of the heavy chain. The term "mAb" refers to monoclonal antibody.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

As used herein, the term "monitoring" refers to the process of detecting and/or observing the development of cancer by determining the abundance of ENO1 protein in cancer cells.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. As is understood by one skilled in the art, prevention or preventing need not achieve absolute (complete) block or avoidance of the conditions. Rather, prevention may achieve substantial (e.g., over about 50%) reduction or avoidance of the diseases or conditions to be prevented. Unless otherwise indicated herein, either explicitly or by implication, if the term "treatment" (or "treating") is used without reference to possible prevention, it is intended that prevention be encompassed as well.

The term "pharmaceutically acceptable" is meant a material that is not biologically or otherwise undesirable, e.g., the material may be incorporated into a formulation of the invention without causing any undesirable biological effects or interacting in a deleterious manner with any of the other components of the dosage form formulation. However, when the term "pharmaceutically acceptable" is used to refer to a pharmaceutical excipient, it is implied that the excipient has met the required standards of toxicological and manufacturing testing and/or that it is included in the Inactive Ingredient Guide prepared by the U.S. Food and Drug Administration. As explained in further detail infra. "pharmacologically active" (or simply "active") as in a "pharmacologically active" derivative or analog refers to derivative or analog having the same type of pharmacological activity as the parent agent.

By an "effective" amount or a "therapeutically effective" amount of an active agent is meant a nontoxic but sufficient amount of the agent to provide a beneficial effect. The amount of active agent that is "effective" will vary from subject to subject, depending on the age and general condition of the individual, the particular active agent or agents, and the like. Unless otherwise indicated, the term "therapeutically effective" amount as used herein is intended to encompass an amount effective for the prevention of an adverse condition and/or the amelioration of an adverse condition, i.e., in addition to an amount effective for the treatment of an adverse condition.

The present invention discloses an antibody, or an antigen-binding fragment thereof, specifically binds human ENO1, thereby inhibiting ligand (e.g., plasminogen) binding to ENO1. By inhibiting binding of plasminogen to ENO1, the antibodies of the invention can inhibit plasminogen activation. In some embodiments of the invention, the antibody is a polyclonal antibody, a monoclonal antibody, a humanized antibody or a fully human antibody.

In some embodiments of the invention, the antibody, or the antigen-binding fragment thereof, binds to an epitope on human ENO1 and inhibit ENO1 plasminogen receptor activity, wherein the epitope is located in a region consisting of the sequence of $^{296}$FDQDDWGAWQKFTASAGIQVVGD-DLTVTNPKRIAKAVNEKS$^{336}$ (SEQ ID NO: 39) of human ENO1.

In some embodiments of the invention, the antibody, or the antigen-binding fragment thereof, binds to an epitope located in a region consisting of the sequence of $^{296}$FDQD-DWGAWQKFTA$^{309}$ (SEQ ID NO: 40) or $^{326}$KRI-AKAVNEKS$^{336}$ (SEQ ID NO: 41) of human ENO1.

In some embodiments of the invention, the antibody, or the antigen-binding fragment thereof, binds to human ENO1 with very high affinity (i.e., low dissociation constant (KD)). For example, a humanized antibody that is capable of binding ENO1 with a KD less than about $10^{-5}$, $10^{-6}$, $10^{-7}$, $10^{-8}$, $10^{-9}$, $10^{-10}$ or about $10^{-11}$ M, or any range or value therebetween. Affinity and/or avidity measurements can be performed using ELISA and/or BIACORE, as described herein or according to techniques known in the art. In a preferred embidiment, the KD value of the antibody, or the antigen-binding fragment thereof, to ENO1 is 10 nM or less, more preferably 1.0 nM or lower.

In some embodiments, the invention relates to an antibody, or an antigen-binding fragment thereof, that binds human ENO1, comprising (i) a light chain variable region (VL) comprising LCDR1 (RASENIYSYLT; SEQ ID NO: 6), LCDR2 (NAKTLPE; SEQ ID NO: 7) and LCDR3 (QHHYGTPYT; SEQ ID NO: 8), and (ii) a heavy chain variable region (VH) comprising HCDR1 (GYTFTS-CVMN; SEQ ID NO: 3), HCDR2 (YINPYNDGTKYNEK-FKG; SEQ ID NO: 4) and HCDR3 (EGFYYGNFDN; SEQ ID NO: 5).

In some embodiments of the invention, the antibody, or the antigen-binding fragment thereof, comprises a VL comprising amino acid residues 1-108 of SEQ ID NO: 2 or 9; and/or a VH comprising amino acid residues 1-119 of SEQ ID NO: 1, 10 or 11.

In some embodiments, the invention relates to an antibody, or an antigen-binding fragment thereof, that binds human ENO1, comprising (i) a light chain variable region (VL) comprising LCDR1 (RASENIYSYLT; SEQ ID NO: 6), LCDR2 (NAKTLPE; SEQ ID NO: 7) and LCDR3 (QHHYGTPYT; SEQ ID NO: 8), and (ii) a heavy chain variable region (VH) comprising HCDR1 (GYTFTS-Xaa-VMN, wherein Xaa is any amino acid but cysteine; SEQ ID NO: 50), HCDR2 (YINPYNDGTKYNEKFKG; SEQ ID NO: 4) and HCDR3 (EGFYYGNFDN; SEQ ID NO: 5). In a preferred embodiment, Xaa is serine or alanine.

In some embodiments of the invention, the antibody, or the antigen-binding fragment thereof, compries a VL comprising amino acid residues 1-108 of SEQ ID NO: 2 or 9; or a VH comprising amino acid residues 1-119 of SEQ ID NO: 1, 10 or 51.

Further embodiments of the invention may relate to methods for producing high affinity antibodies to human ENO1 by immunizing a mammal with human ENO1 protein, a fragment thereof, and one or more orthologous sequences or fragments thereof. For example, the immunization can be carried out by injection of the ENO1 protein. Identification of suitable antibodies is also possible by screening of hybridoma supernatant with the corresponding molecules (antigens). After identification, the antibodies can be produced by methods that are known to a person skilled in the art.

Some embodiments of the invention relate to an isolated nucleic acid molecules encoding the antibodies described herein. Vectors having the isolated nucleic acid molecules encoding anti-ENO1 antibody or host cells transformed with any of the vectors are also disclosed.

In addition, some embodiments of the invention relate to a method for producing an anti-ENO1 antibody by culturing host cells under conditions wherein a nucleic acid molecule is expressed to produce the antibody, followed by recovering the antibody. It should be realized that embodiments of the invention may also include any nucleic acid molecule which encodes an antibody or fragment of an antibody of the invention including nucleic acid sequences optimized for increasing yields of antibodies or fragments thereof when transfected into host cells for antibody production. Methods for the production of suitable polyclonal, monoclonal and recombinant antibodies, including the production of binders and aptamers, are known to a person skilled in the art (see, for example, Jorg Knablein (editor), Modern Biopharmaceuticals, vol. 2, p. 635); see also the Examples described below.

In another aspect, the invention features compositions. e.g., pharmaceutical compositions, particularly, vaccines. The compositions can include a therapeutically effect amount of the antibody, or the antigen-binding fragment thereof, as described herein, and a pharmaceutically acceptable carrier.

Pharmaceutically acceptable carriers are generally non-toxic to recipients at the dosages and concentrations employed, and include, but are not limited to, buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The compositions may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Some typical compositions are in the form of injectable or infusible solutions, intended for parenteral administration (e.g., intravenous, subcutaneous, intraperitoneal, intramuscular). In some embodiments, the composition is administered by intravenous infusion or injection. In other embodiments, the composition is administered by intramuscular or subcutaneous injection.

A therapeutically effective amount of the antibody, or the antigen-binding fragment thereof, may vary according to factors such as the disease state, age, sex, and weight of the individual, and the ability of the antibody, or the antigen-binding fragment thereof, to elicit a desired response in the individual. A therapeutically effective amount is also one in which any toxic or detrimental effects of the immunoconjugate is outweighed by the therapeutically beneficial effects. A "therapeutically effective dosage" can be evaluated by assays known to the skilled practitioner.

Some embodiments of the invention relate to methods for treating a subject suffering from an ENO1 protein-related disease or disorder, the method comprises administering a therapeutically effective amount of the antibody, or the antigen-binding fragment thereof, as described herein to the subject.

Bae's study (J. Immunology, 189:365-372 (2013)) indicates that when RA patients' PBMCs are treated with an antibody against ENO1, the ENO1 plasminogen receptor activity is stimulated, and monocytes and macrophages from the PBMCs would produce higher amount of pro-inflammatory mediators, such as TNFα, IL1-α/β, IFN-γ and PGE2 via p38 MAPK and NF-κB pathway. In contrast to this observation, inventors of this invention surprisingly found that the administration of antibodies directed against ENO1 can effect a clinical improvement of rheumatoid arthritis. That is, it was found that by administering antibodies directed against ENO1 activity instead of activation with the antibody epitope which is different from that chosen by Bae et al., a clinical improvement in an inflammatory disease or immune disorder (such as rheumatoid arthritis) can be achieved. Likewise, it was found that a clinical improvement in multiple sclerosis can be effected. These observations suggest that not every ENO1 antibody has therapeutic effect on immune diseases and this effect is epitope dependent.

Furthermore, it was surprisingly found that a treatment is not only possible during the initiation of the disease in an animal model, but also when explicit clinical symptoms of the disease are already present. This allows for a relatively late therapeutic intervention, among others, as it is required in human clinical practice. Therefore, the invention may relate to a method for administering the antibody, or the antigen-binding fragment thereof, as described herein to a subject (e.g., a human or a non-human animal) for the treatment of an inflammatory disease or immune disorder, such as multiple sclerosis, rheumatoid arthritis, Crohn's disease, ulcerative colitis, or systemic Lupus erythematosus or an immune disorder.

In some embodiments of the invention, by inhibiting binding of plasminogen to ENO1, the antibody, or the antigen-binding fragment thereof, of the invention can inhibit plasminogen activation, leading to reduced degradation of extracellular matrix, which in turn prevents or reduces dissociation of cancer cells from the extracellular matrix. This results in the inhibition of the urokinase plasminogen activation system (uPAS) in the extracellular matrix of cancer cells. Therefore, the antibody, or antigen-binding fragement thereof the invention can be used to inhibit tumor growth and metastasis. Mechanisms by which this can be achieved may include, but are not limited to, inhibition of binding of a ligand (such as plasminogen) to its receptor ENO1, or abrogation of inter-reactions between the receptor ENO1 and its ligands, thereby reducing the effective concentration of ENO1.

Disease-related aberrant activation or expression of "ENO1" may be any abnormal, undesirable or pathological cell adhesion, for example tumor-related cell adhesion. Cell adhesion-related diseases include, but are not limited to, non-solid tumors such as leukemia, or lymphoma, and also solid tumors such as melanoma, non-small cell lung cancer, hepatocellular (liver) carcinoma, gastric, head and neck, hepatic system, stomach, breast, ovary, lung, lung, uterus, vulva, colorectum, and pancreas. Therefore, the invention may relate to a method for administering the antibody, or the antigen-binding fragment thereof, as described herein to a subject (e.g., a human or a non-human animal) for the treatment of a neoplastic disease, such as lung cancer, breast cancer, pancreas cancer, liver cancer, colorectal cancer, or prostate cancer, in a subject (e.g., a human or a non-human animal).

Further embodiments of the invention relate to the uses of the antibody, or the antigen-binding fragment thereof, as described herein in the preparation of a medicament for the treatment of an ENO1-related disease or disorder in a subject (e.g., a human or a non-human animal).

In accordance with some embodiments of the invention, the antibody, or the antigen-binding fragment thereof, as described herein may be used to inhibit the invasion activity of a cancer cell. For example, the antibodies of the invention can inhibit greater than 40%, 50%, 60%, or 70% of the invasion activity of 1U937 human lymphoma cells at antibody concentrations as low as 50 microgram/ml or less.

In accordance with some embodiments of the invention, the antibody, or the antigen-binding fragment thereof, as described herein inhibit extracellular matrix degradation, thereby inhibiting cancer cell dissociation from the extracellular matrix. For example, an antibody of the invention can inhibit greater than 40%, 50%, or 60% of plasminogen mediated dissociation of CL1-5 cells from collagen or fibronectin at antibody concentrations as low as 50 microgram/ml or less.

Some embodiments of the invention relate to a method for monitoring cancer development. The method may comprise determining the abundance of alpha-enolase proteins (ENO1) in a sample (e.g., cancer cells), wherein an increased level of ENO1 correlates with cancer severity. In accordance with embodiments of the invention, the abundance may be determined by measuring binding of the antibody, or the antigen-binding fragment thereof, as described herein to the ENO1 proteins.

Some embodiments of the invention relate to a method for detecting cancer. Such a method may comprise determining the abundance of ENO1-specific antibodies in serum samples, wherein a low level of ENO1-specific antibodies indicates the presence of a malignant tumor.

Methods for determining the abundance of ENO1 include, but are not limited to, measuring the binding of ENO1 proteins and ENO1-specific antibodies, Western blotting, flow cytometry, immunohistochemistry (IHC), RT-PCR, and/or microarray analysis.

The following examples are presented to illustrate certain embodiments of the present invention, but should not be construed as limiting the scope of this invention.

EXAMPLE 1

The ENO1 Binding ELISA of EN10mAb Antibody

To evaluate the ENO binding affinity of anti-human ENO1 antibody EN10 mAb, the hybridomas were grown in RPMI containing 10% fetal calf serum (FCS). After one week culture, $1 \times 10^6$ cells were collected, washed with PBS, resuspended in 200 µl RPMI medium, and injected into severe combined immunodeficiency (SCID) mice by IP injection. Three weeks later, ascites of mice were collected and diluted to 15 ml. Antibody was further purified by 40% ammonium sulfate and Protein A column (Montage antibody purification kit Millipore). The purified antibody was concentrated with an Amicon Ultra-15 centrifugal filter device, following the protocols provided by the manufacturer (Millpore). The purity of antibody was analyzed by 12% SDS PAGE.

400 ng of human ENO1 protein was coated on a 96-well ELISA plate, and the plate was further washed with PBS. Serial dilutions from $1 \times 10^{-12}$ to $1 \times 10^{-8}$ M of EN10 mAb antibody were added to the plate, and the plate was incubated at 37° C. for 1 hour. A goat anti-mouse IgG conjugated with hypoxanthine phosphoribosyltransferase (HPRT) was added. After 1 hour, 3,3',5,5'-Tetramethylbenzidine (TMB) was added and OD405 was read. Every study was repeated three times. Data were presented as mean±SD. OD readings and concentrations of antibodies were used to make a multiple scatter plot using Sigmaplot. The KD values were predicted by four parameter logistic fit.

Figure 1:
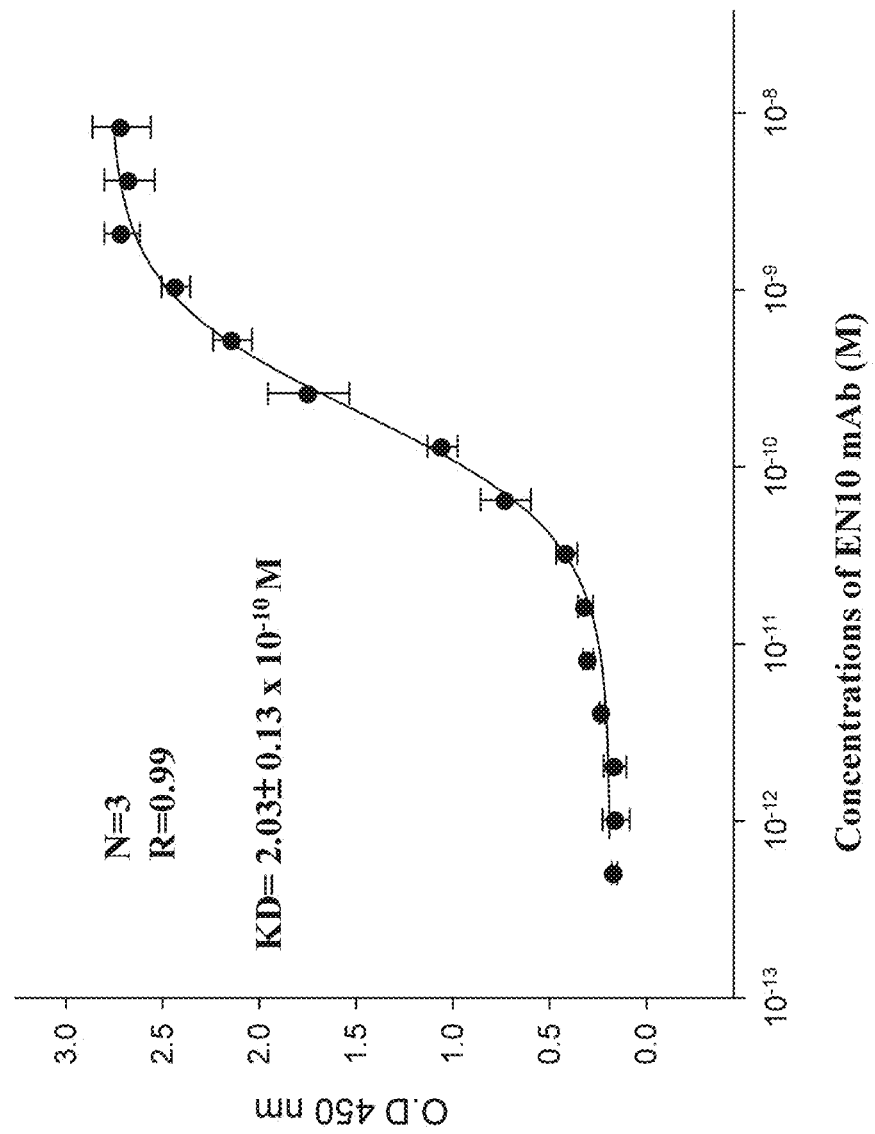
FIG. 1 shows ELISA results from ENO1 binding by EN10 mAb isolated from acites of hybridoma. Ammonium sulfate purification, protein A column purification, and SDS-PAGE purification were performed as described in Example 1. These data show the KD of anti-human ENO1 antibody EN10 mAb.

The results of this experiment are shown in FIG. 1. Antibody EN10 mAb had productivities from 20.4 mg to 4.6 mg per mice. The KD value of EN10 mAb antibody was $2.03 \pm 0.12 \times 10^{-10}$ M (N=3). This result suggests that EN10 mAb antibody can recognize the human ENO1 protein and has a favor affinity with a KD value of about $2.03\pm0.12\times 10^{-10}$ M (N=3).

EXAMPLE 2

To assess the capability of EN10 mAb to inhibit the ENO1 plasminogen receptor activity of cancer cells, a human lymphoma U937 cell line was grown in RPMI containing 10% FCS. Cells were treated with 10 microgram/ml of LPS for 6 hours to induce ENO1 protein expression on the cell surface, $1.5\times10^6$ cells/ml in PBS were then pre-incubated with 1 microgram/ml human Lys-plasminogen and 10 microgram/ml of EN10 mAb for one hour, respectively. Samples were washed with PBS twice and 3 nM of tissue specific plasminogen activator and 0.5 mM of chromogenic substrate S-2251 were added. After one hour incubation at 37° C. OD 405 was read. Every study was repeated three times, and the antagonist activity was analyzed. Data were presented as mean±SD. T-test was used to compare each group. P values <0.05 were considered statistically significant.

Figure 2:
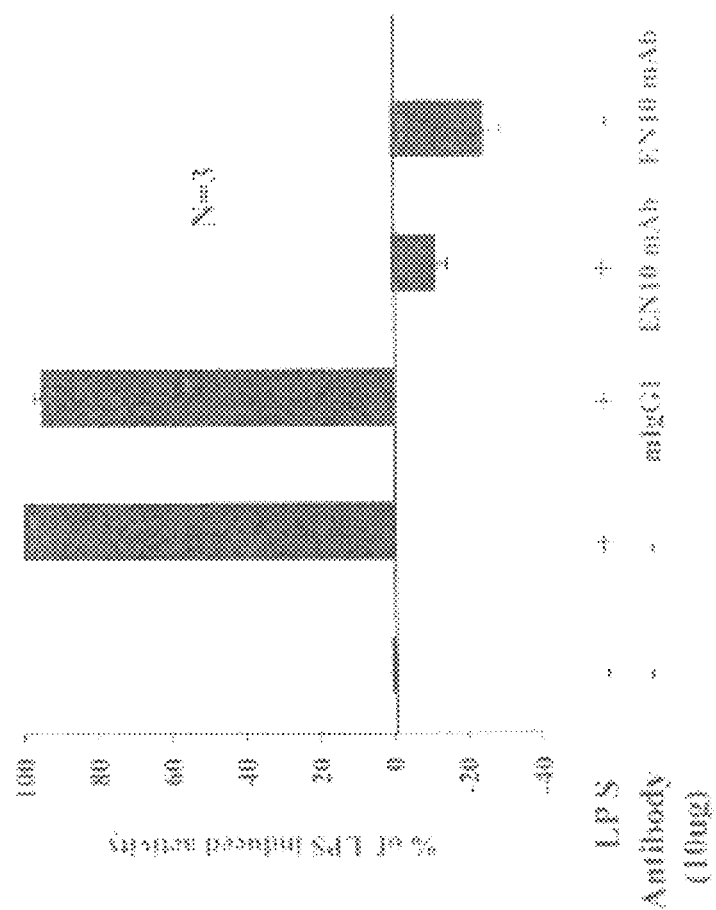
FIG. 2 shows the results of U937 fibrinolytic assay of EN10 mAb. The induction of ENO1 expression by LPS in human U937 lymphoma cell line and the plasmin activity assay were performed as described in Example 2. These result proves that EN10 mAb alleviates the plasminogen receptor activities of inducible ENO1 protein.

Results of this experiment are shown in FIG. 2. EN10 mAb had a high ENO1 plasminogen receptor antagonist activity and can achieve 100% inhibition of LPS-induced specific ENO1 activity. Therefore. EN10 mAb has a good potential in inhibiting the transmigration of cancer cells to the target organs.

EXAMPLE 3

The result of Example 2 suggests that EN10 mAb can inhibit the ENO1 plasminogen receptor activity. The inhibition of ENO1 plasminogen receptor activity may result in the inhibition of plasminogen activation and transmigration activity in the LPS-stimulated human U937 lymphoma cell line.

To assess whether compromising the ENO1 plasminogen receptor activity results in the alleviation of invasion activity of cancer cells, a human lymphoma U937 cell line was grown in RPMI containing 10% FCS. Cells were treated with 10 microgram/ml of LPS for 6 hours to induce ENO1 protein expression on cell surface. After being mixed with 5 to 50 microgram/ml of EN10 mAb, $2\times10^4$ cells were seeded in the top chamber of a two-chamber assay system containing 15 micro molar of Lys-plasminogen and incubated for 24 hours with media containing 10% FBS and 10 nM MCP-1 in the lower chamber. An anti-mouse IgG was used as a negative control group. Two chambers were separated by a micropore filter (8 micrometer pore size) coated with matrigel. After the incubation period, cells in the lower chamber were counted by a hemocytometer under a microscope. Every study was repeated three times. Data are presented as mean±SD. T-test was used to compare each groups. P values <0.05 were considered statistically significant.

Figure 3:
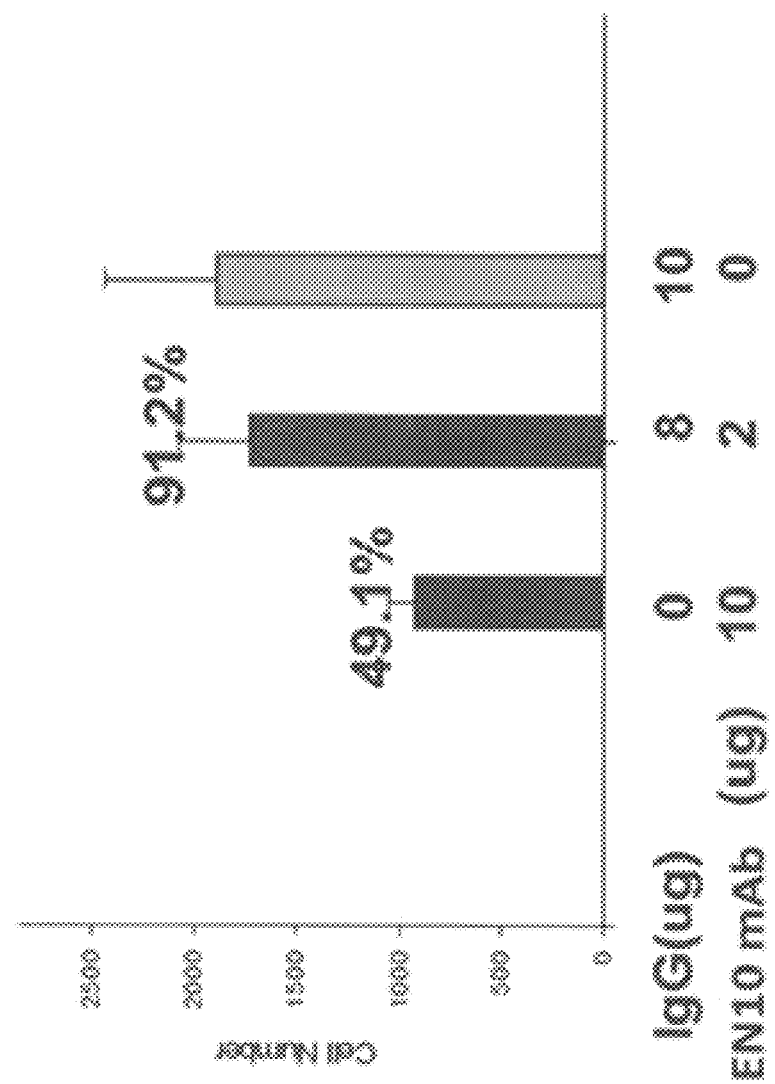
FIG. 3 shows results of invasion activities of U937 cells treated with different concentrations of EN10 mAb isolated from hybridoma, after the surface ENO1 expression of cells was induced by LPS. Detailed procedures were performed as described in Example 3. These data show that the EN10 mAb inhibits the invasion activity of U937 cells in a dose-dependent manner.

The results are shown in FIG. 3. When LPS-treated U937 cells were treated with 5 to 50 microgram/ml of EN10 mAb, the invasion activity of U937 was from 90.2±2% to 49.1±1% (N=3) of the control IgG. These results indicate that EN10 mAb can alleviate the invasion capability of activated U937 by compromising the ENO1 plasminogen receptor activity in a dose-dependent manner. By targeting ENO1 protein on the surface of lymphoma, it is feasible to inhibit cells entering affected sites using EN10 mAb.

EXAMPLE 4

EN10 mAb Recognizes the Surface ENO1 of U937 Lymphoma Cell Line Stimulated by LPS Human U937 lymphoma cells were grown in RPMI containing 10% FCS. Cells were treated with 10 microgram/ml of LPS for 6 hours to induce ENO1 protein expression on the cell surface. For flow cytometric analysis, the intact whole cells were stained with or without EN10 mAb (1:300 dilution), visualized with FITC-conjugated goat antiserum (Jackson Lab), and analyzed with FACScan flow cytometer (Becton Dickinson). ENO1 expression was measured by the resulting fluorescence intensity.

Figure 4:
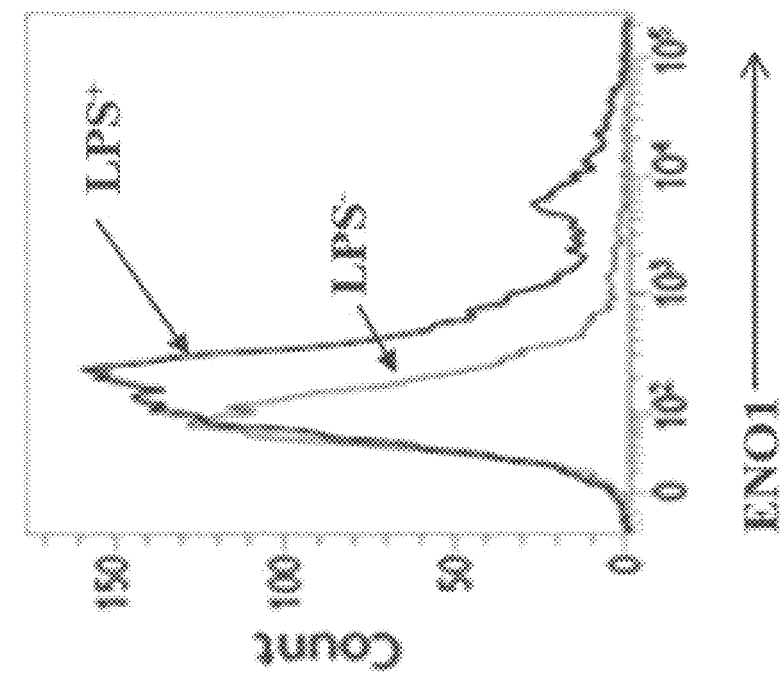
FIG. 4 shows that EN10 mAb recognizes the cell surface ENO1 on U937 cells treated with LPS. Detailed procedures were performed as described in Example 4. The histogram indicates that ENO1 is high expressed in the surface of U937 after cells were administrated with LPS.

Results from these experiments are shown in FIG. 4. Incubating U937 with LPS and EN10 mAb shifts the histogram to the right, as compared to incubating the cells without LPS but with EN10 mAb. This result indicates that U937 cells increase in expressing ENO1 on their cell surfaces when cells are treated with LPS. These data support the notion that EN10 mAb recognizes LSP-induced surface ENO1 on the lymphoma cells.

EXAMPLE 5

Cloning of the Gene Encoding the Antibody EN10 mAb was Performed in Accordance with the Methods Described Below (1) cDNA Cloning of Antibody Genes and Preparation.

The hybridoma was cultured in a RPMI medium (manufactured by Gibco) containing 10% FCS. After the cell number reached about $10\times10^6$/ml, the cells were collected by centrifugation, and then TRIzol® (manufactured by Invitrogen) was added to extract total RNA in accordance the instruction manual. Cloning of the variable region of the antibody cDNAs was performed using a mouse Ig-primer set (manufactured by Novagen) in accordance with the attached instruction manual.

(a) Synthesis of 1st Strand cDNA was Performed in Accordance with the Instruction Manual of SuperScript® III First-Strand Synthesis System (Manufactured by Invitrogen).

The 1st strand cDNA was prepared using 5 microgram of the total RNA as a template. Five micrograms of total hybridoma RNA, 1 microL of 50 ng/microL of random primers, and 1 microL of 10 mM dNTP were mixed, and DEPC-treated water was added to 10 microL in a 200 microL PCR tube. The reaction mixture was incubated at 65° C. for 5 min, and then placed on ice for at least 1 minute. Ten microL of cDNA Synthesis Mixture containing 2 microL of 10×RT buffer, 4 microL of 25 mM $MgCl_2$, 2 microL of DTT, 1 microL of 4 unit RNaseOUT™, and 1 microL of 200 unit SuperScript® III RT were added, mixed gently, and collected by brief centrifugation. The reaction tube was incubated for 10 min at 25° C. and followed by 50 min at 50° C. The reaction was terminated at 85° C. for 5 min and chilled on ice. The tube was briefly centrifuged to collect the reaction product, and 1 microL of RNase H was added and incubated for 20 min at 37° C.

(b) Amplification by PCR of Heavy Chain Genes and Light Chain Genes

A reaction solution having a composition of 5 microL of cDNA, 5 microL of 10× reaction buffer, 1 microL of 10 mM dNTP mix, 1 microL of 2.5 unit Taq polymerase, and 1 microL of forward primer 1, and 1 microL of reverse primer 2 provided by the primer set was prepared in a final volume of 50 microL with double distilled water and subjected to PCR.

For amplification of the light chain and heavy chain of an antibody, a cycle of 94 degree C. for 10 minutes was used, then a cycle of 94 degree C. for one minute, 52 degree C. for one minute, and 72 degree C. for 1 minute was repeated 35 times, and the reaction was incubated at 72 degree C. for 10 more minutes. The reaction solution was subjected to 2% agarose gel electrophoresis to analyze the reaction products. Products with the correct molecular weights, about 463 bps for the heavy chain and 451 bps for the light chain, were ligated to a pCR 2.1-TOPO vector (manufactured by Invitrogen) for subcloning in accordance with the attached instruction manual. M13 forward (5'-GTAAACAAC-GACGGCGAG-3' (SEQ ID NO:12) and M13 reverse (5'-CAGGAAACAGCTATGAC-3' (SEQ ID NO:13)) primers were then used to determine the nucleotide sequence. Based on the sequence information, antibody sequences were translated into proteins sequences by ExPASY-Translation Tool. Resulting sequences of EN10 mAb comprise a heavy chain amino acid sequence and a light chain sequence having complementarity determining regions (CDR), which were determined by the method published by Kabat et al., Sequences of Proteins of Immunological Interest, Fifth Edition, NIH Publication 91-3242. Bethesda Md. (1991). vols. 1-3.

FIG. 5A depicts the variable heavy chain region amino acid sequence of EN10 mAb (SEQ ID NO: 1). The framework regions (FR1, FR2, FR3, and FR4) and CDRs (HCDR1 (SEQ ID NO: 3), HCDR2 (SEQ ID NO: 4), and HCDR3 (SEQ ID NO: 5)) are indicated.

FIG. 5B depicts the variable light chain region amino acid sequences of EN10 mAb (SEQ ID NO: 2). The framework regions (FR1, FR2, FR3, and FR4) and CDRs (LCDR1 (SEQ ID NO: 6), LCDR2 (SEQ ID NO: 7), and LCDR3 (SEQ ID NO: 8)), are indicated.

EXAMPLE 6

Humanization of EN10 mAb
Selection of Human V Region Framework Sequences

Using mouse monoclonal antibody EN10 mAb as the parent antibody, EN10 mAb CDR sequences according to the Kabat definitions were described in the FIGS. 5A and 5B (SEQ ID NO:1 and SEQ ID NO:2).

For hum EN10 mAb 4D5, the human acceptor framework was selected from database or utilizing a framework that has been validated in the clinic. Human heavy and light chain framework sequences in the VH subgroup III, IGHV3-66*04 (SEQ ID NO:10 and VL κ subgroup I, IGKV1-39*01 (SEQ ID NO:9) (FIG. 6A) have been validated in the clinic and used in many humanized antibodies with success.

For hum EN10 mAb IMGT, human germ-line VL and VH sequences with the highest degree of homology with the EN10 mAb framework regions were identified from the IMGT database (the International immunogenetics Information System®). The homology searches may be performed with BLAST or similar methods. The EN10 mAb variable region sequences used as query sequences are available from the literature, such as U.S. patent application Ser. No. 14/142,186.

Human heavy chain framework sequences in the VH subgroup III (VH3) have been used in many humanized antibodies with success, and human light chain framework sequences of the VL κ subgroup II (Vκ2) are also shown to be good candidates. Therefore, the framework sequences of VHIII and Vκ2 subgroups were selected for the search for VH and VL frameworks, respectively. These searches identified IGHV3-72*01 and IGKV2D-29*02, respectively, as the VH and VL sequences most homologous to the corresponding heavy chain and light chain framework sequences in EN10 mAb.

As shown in FIG. 6B, the sequences of IGHV3-72*01 heavy chain framework regions differ from those in EN10 mAb by 19 amino acids (the boxed residues), which corresponds to a 23.45% (19/81 total residues in the framework regions) variation. For the light chain framework as shown in FIG. 6B, the sequences of IGKV2D-29*02 differ from those in EN10 mAb by 10 amino acids (the boxed residues), which corresponds to a 13.16% (10/76 total residues in the framework regions) variation.

Even with these degrees of variations in the framework regions, a scFv (HH12) generated by grafting CDR sequences from EN10 mAb into the IGHV3-72*01 and IGKV2D-29*02 sequences has a relatively good affinity for ENO1 (KD=2.3×10$^{-10}$ M) (see Table I below). These results suggest that the framework regions can tolerate a relatively high degree of variations without impacting the CDR region conformations.

TABLE I

| ENO1 binding ELSA of EN10 chimera and Hum EN10 IMGT | | |
|---|---|---|
|  | Mouse chimera | Hum EN10 IMGT |
| KD (M) | 3.33E−11 | 3.65E−11 |

These two pairs of light chain and heavy chain sequences (hum 4D5 and hum IMGT) will be used as examples for the construction of humanized antibodies against human ENO1.

EXAMPLE 7

Binding Affinity Analysis of Humanized Antibodies

Figure 7A:
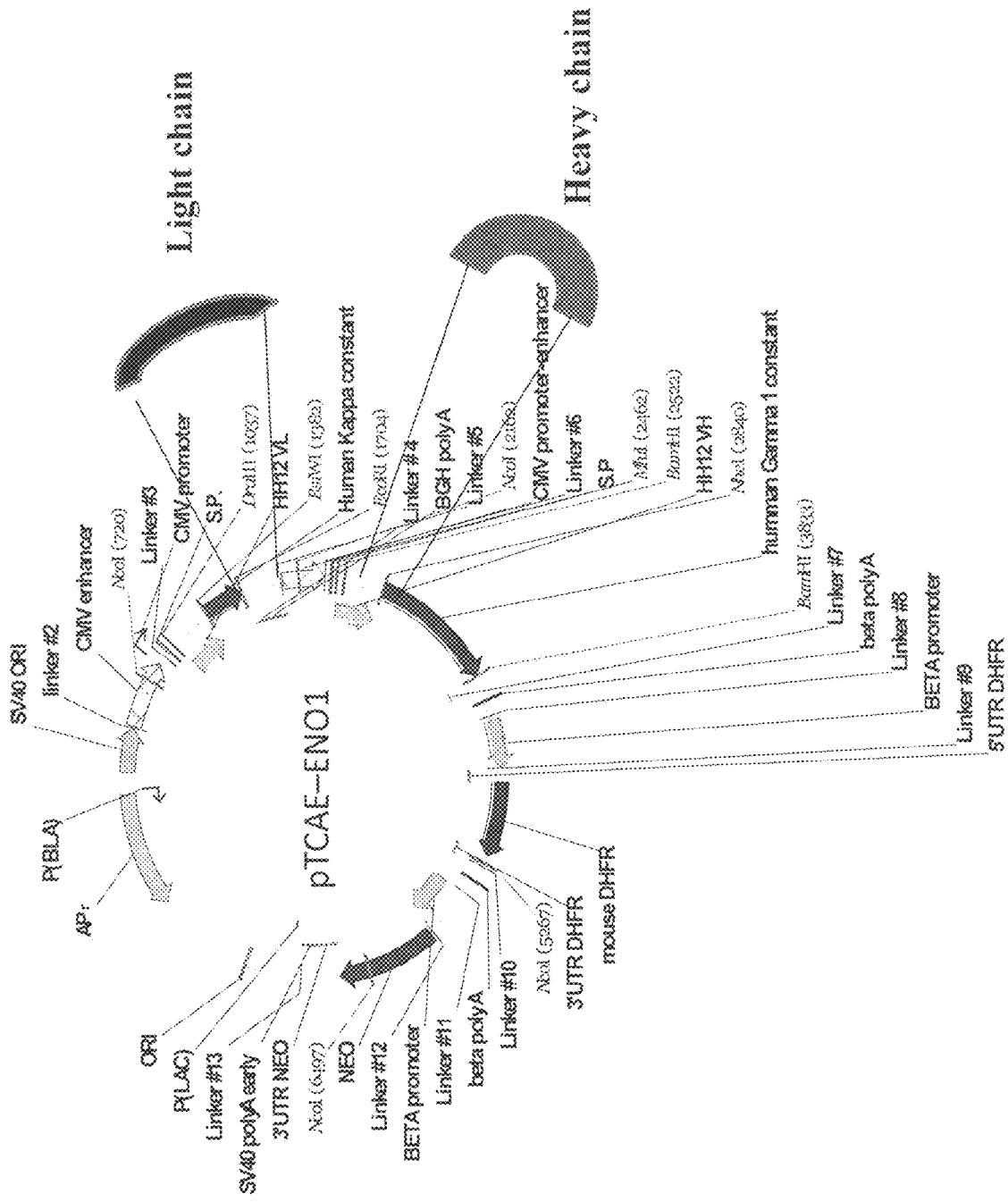
FIG. 7A shows an expression vector for the generation of mouse-human chimera and humanized editions of EN10 mAb. The detailed procedures for the purification of the different EN10 mAb editions of antibodies are described in Example 7.

To confirm the affinity change after the mouse antibodies was humanized, the variable regions of humanized light chain and humanized heavy chains of IMGT and 4D5 edition were directly generated by the nucleotide synthesis method, respectively. The mouse variable region, humanized edition of IMGT and 4D5 variable regions and a human Fc chimera antibody expression vector pTCAE8-ENO1, as shown in FIG. 7A, were introduced into host cells to prepare recombinant antibody-expressing cells. As the host cells for expression, the FreeStyle293 cells (manufactured by Invitrogen) were used. The vector was introduced into the host cells by lipofectamine 2000 in accordance with the included instruction manual (manufactured by Invitrogen.) About 2.5 microgram of the antibody expression vector was linearized by restriction enzymes, the gene was introduced into 4×10$^6$ cells, and cells were inoculated to a 6-well culture plate. The agent corresponding to a selection marker of the expression vector was added, and cells were continuously cultured to form a stable pool.

A culture supernatant containing human IgG antibody was prepared by the method described below. The antibody-producing cells were acclimated in a Free Style™ 293 Expression Medium (GIBCO). The cells were cultured in a tissue culture flask, and the culture supernatant was collected when the viable rate of the cells was 90%. The collected supernatant was filtered through 10 micrometer and 0.2 micrometer filters (manufactured by Millipore) to remove contaminants. The culture supernatant containing the antibody was affinity-purified using Protein A (manufactured by Millipore), PBS as an absorption buffer, and 20 mM sodium citrate buffer (pH 3.0) as an elution buffer. The elution fractions were adjusted to around pH 6.0 by adding 50 mM sodium phosphate buffer (pH 7.0). The prepared antibody solution was replaced with PBS using a dialysis membrane (10,000 MW cut, manufactured by Spectrum Laboratories) and filter-sterilized through a membrane filter (manufactured by Millpore) having a pore size of 0.22 micrometer to yield the purified antibody. The concentration of the purified antibody was determined by measuring the absorbance at 280 nm and converting the measured value based on 1.45 optimal density equaling 1 mg/ml.

To know the binding kinetics difference among individual antibodies, surface plasmon resonance (SPR) measurement with a BIAcore 2000 (BIAcore. Inc., Piscataway, N.J.) was used as previously described (Karlsson & Falt, (1997) J. Immunol Methods 200:121-133). Carboxymethylated dextran biosensor chips (CM5, BIAcore Inc.) were activated with N-ethyl-N'-(3-dimethylaminopropyl)-carbodiimide hydrochloride (EDC) and N-hydroxysu-ccinimide (NHS) according to the supplier's instructions. Chimera EN10 mAb was diluted with 10 mM sodium acetate, pH 4.8, into 5 microgram/ml before injection at a flow rate of 20 micro L/minute to achieve approximately 100 response units (RU) of coupled protein followed by the injection of 1M ethanolamine to block unreacted groups. For kinetics measurements, two-fold serial dilutions of ENO1 (0.3125 nM to 40 nM) were injected in HBS-P Biacore running buffer provided by the manufacturer (BIAcore, Inc., Piscataway, N.J.) at 25 degree C. at a flow rate of 25 microL/min. and binding responses on the EN10 mAb were corrected by subtraction of responses on a blank flow cell. Association rates (kon or ka) and dissociation rates (koff or kd) were calculated using a simple one-to-one Langmuir binding model with separate fittings of kon and koff was used. (BIAcore™ Evaluation Software version 3.2).

The results are shown in the FIG. 7 B and Table II. The kon and koff of chimera EN10 mAb binding with ENO1 are $3.57 \times 10^5$ and $8.271 \times 10^{-5}$, respectively, and KD is $2.311 \pm 0.003 \times 10^{-10}$ mol/L. The kon and koff of hum EN10 mAb IMGT binding with ENO1 are 5.311E+5 and 1.162E-4, respectively, and KD is 2.188E-10 mol/L. For the 4D5 humanized edition, the kon and koff o are 3.511E+5 and 1.755E-4, respectively, and KD is $4.997 \pm 0.003 \times 10^{-10}$ mol/L.

To assess the capability of hum EN10 mAb 4D5 mAb and hum EN10 mAb IMGT to inhibit the ENO1 plasminogen receptor activity of cancer cells, a human lymphoma U937 cell line was grown in RPMI containing 10% FCS. Cells were treated with 10 microgram/ml of LPS for 6 hours to induce ENO1 protein expression on the cell surface. $1.5 \times 10^6$ cells/ml in PBS were then pre-incubated with 1 microgram/ml human Lys-plasminogen and different concentrations of hum EN10 mAb 4D5 and hum EN10 mAb IMGT for one hour, respectively. Samples were washed with PBS twice and 3 nM of tissue specific plasminogen activator and 0.5 mM of chromogenic substrate S-2251 were added. After one hour incubation at 37° C. OD 405 was read. Every study was repeated three times, and the antagonist activity was analyzed. Data were presented as mean±SD. T-test was used to compare each group. P values <0.05 were considered statistically significant.

Figure 8A:
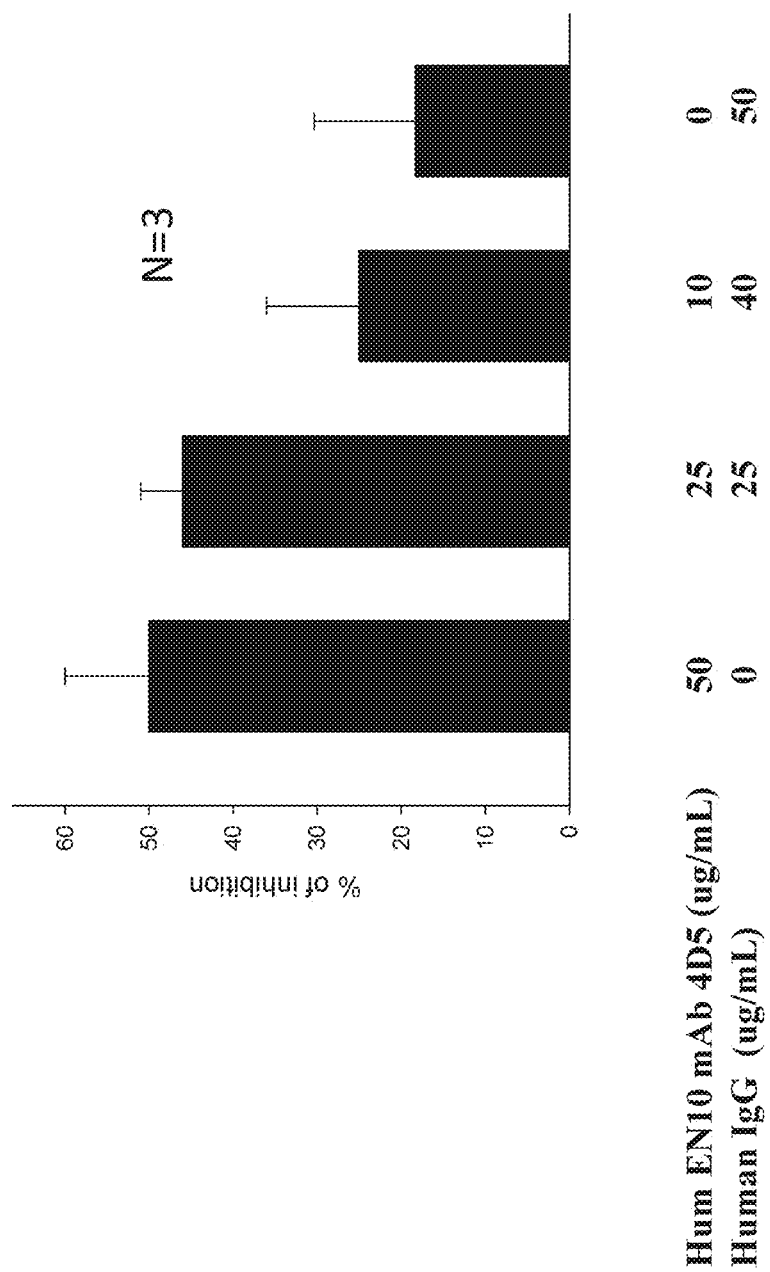
FIGS. 8A and 8B depict results of U937 fibrinolytic assay of humEN10 mAb 4D5 and hum EN10 mAb IMGT antibodies, respectively. The induction of ENO1 expression by LPS in human U937 lymphoma cell line and the plasmin activity assay were performed as described in Example 2. Data show that the same as EN10 mAb both humEN10 mAb 4D5 and hum EN10 mAb IMGT alleviate the plasminogen receptor activity of inducible ENO1 protein.
Figure 8B:
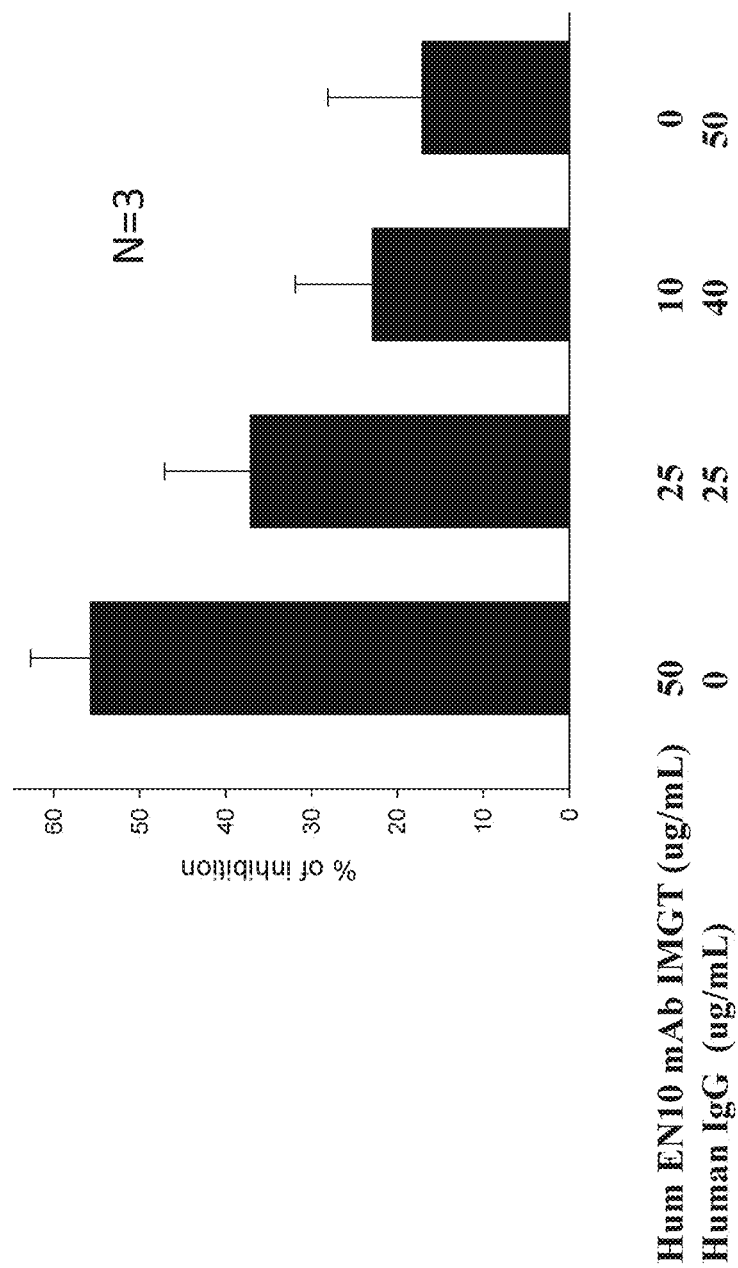

Results of this experiment are shown in FIG. 8A and FIG. 8B. The same as the parent antibody EN10 mAb, 50 microgram of both hum EN10 mAb 4D5 and hum EN10 mAb IMGT had high ENO1 plasminogen receptor antagonist activities and can achieve 50 and 56% inhibition of LPS-induced specific ENO1 activity, respectively, and the inhibition percentage is dose-dependent. Therefore, both humanized antibodies have good potentials in inhibiting the transmigration of cancer cells to the target organs.

EXAMPLE 9

Hum EN10 mAb 4D5 and Hum EN10 mAb IMGT Antibodies Inhibit the Invasion Activity of U937

As results of Example 8, the administrations of humEN10 mAb 45D and EN10 mAb IMGT antibodies reduce the inducible ENO1 plasminogen receptor activity of U937. This may result, as their parent antibody, in the inhibition of invasion activity of cancer cells.

To evaluate the anti-invasion activity of hum EN10 mAb 4D5 and EN10 mAb IMGT, $3 \times 10^6$ of mouse brain endothelial bEnd.3 cells were pre-coated with matrix gel on upper chambers of the Cytoselect™ 24-well Cell Migration and Invasion Assay kit in RPMI-1640 medium containing 10% fetal bovine serum for 24 h. The upper chambers were washed with PBS twice. RPMI medium containing 2% and

TABLE II

| | The binding kinetics of EN10 antibodies by SPR | | | | | |
|---|---|---|---|---|---|---|
| | ENO1 | | | | | Capture |
| Antibody names | Ka | Kd | KD | Rmax(RU) | Chi$^2$ (RU$^2$) | Level |
| Chimera EN10 mAb | 3.577E+5 | 8.271E-5 | 2.313E-10 | 176.8 | 0.668 | 325 |
| Hum EN10 mAb IMGT | 5.311E+5 | 1.162E-4 | 2.188E-10 | 140.0 | 0.656 | 290 |
| Chimera EN10 mAb | 3.575E+5 | 8.250E-5 | 2.308E-10 | 123.1 | 1.10 | 380 |
| Hum EN10 mAb 4D5 | 3.511E+5 | 1.755E-4 | 4.997E-10 | 100.3 | 0.361 | 355 |

Figure 7B:
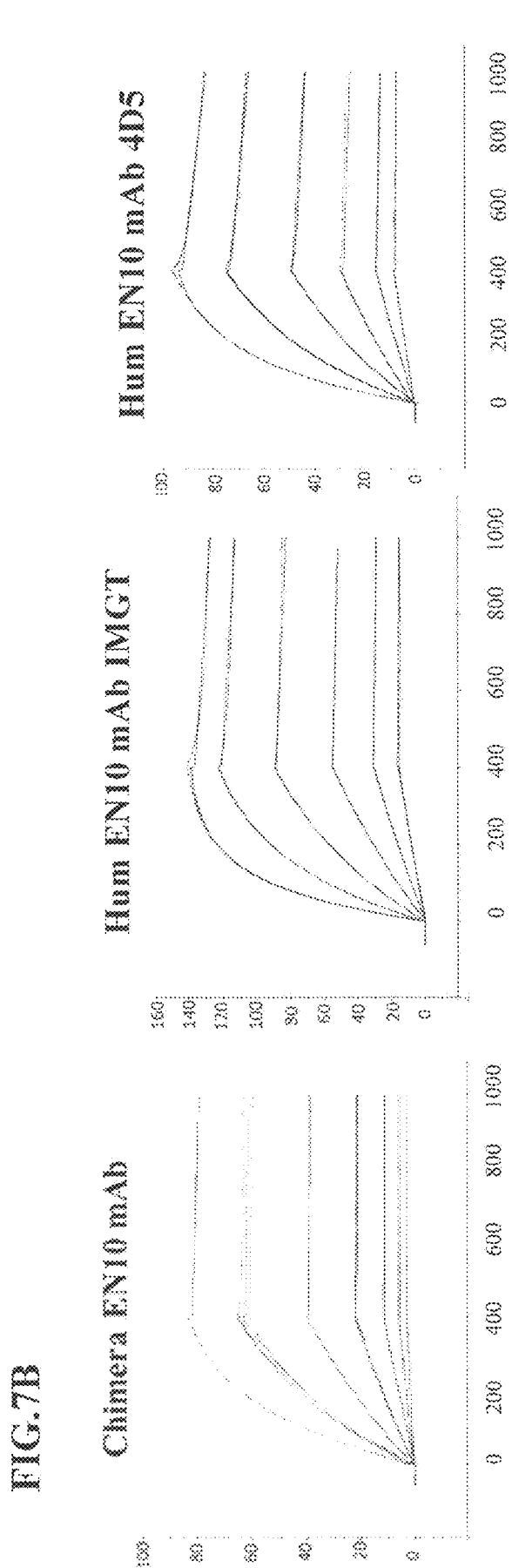
FIG. 7B depicts results from using the chimera EN10, hum EN10 mAb 4D5 and humEN10 mAb IMGT antibodies to determine binding affinity and kinetic constants of EN10 mAb. Detailed procedures of chimera antibody expression, purification and KD analysis were performed as described in Example 7. The result KD of humEN10 mAb IMGT is not significant to that of mouse-human chimera EN10mAb.

From FIG. 7B, the results suggest that all of humanized EN10 antibodies can recognize the human ENO1 protein and after humanization, the affinity of IMGT edition is similar to that of mouse chimera antibody and has a favor affinity with a KD value of about $2.03 \pm 0.12 \times 10^{-10}$ M (N=3).

EXAMPLE 8

Hum EN10 mAb 4D5 and Hum EN10 mAb IMGT Antibodies Inhibit the Plasminogen Receptor Activity Induced by LPS of U937

10% fetal bovine serum were added to upper and lower chambers, respectively. After mixing with 10, 50, and 100 microgram/ml of humEN10 mAb 4D5 and hum EN10 mAb IMGT, respectively, $2 \times 10^4$ cells of U937 were seeded in the top chamber of a two-chamber assay system and incubated for 24 hours. An anti-human IgG was used as a negative control. Two chambers were separated by a micropore filter (8 μm pore size) coated with matrigel. After the incubation period, cell number in the lower chamber were calculated by a hemocytometer under a microscope. Each study was repeated three times. Data were presented as mean±SD.

Figure 9A:
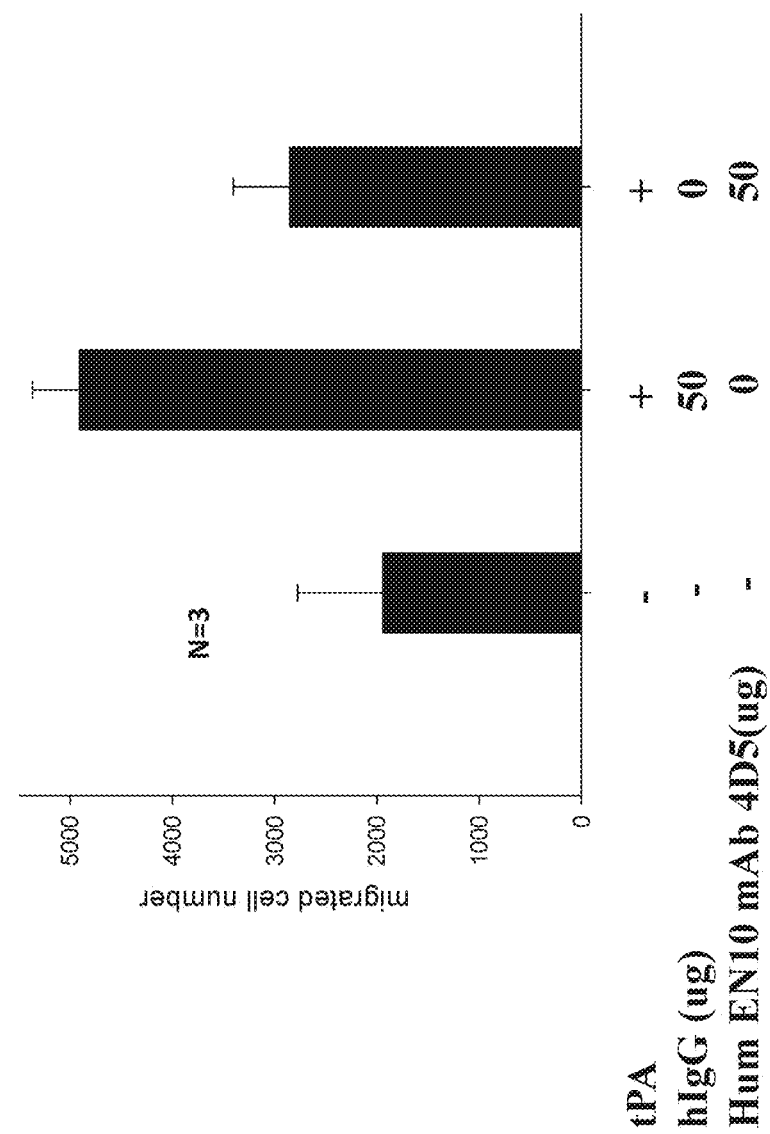
FIGS. 9A and 9B show results of invasion activities of U937 cells treated with different concentrations of humEN10 mAb 4D5 and humEN10 mAb IMGT antibodies, respectively, after the surface ENO1 expression of cells was induced by LPS. Detailed procedures were performed as described in Example 9. These data show that after humanization, the humEN10 mAb 4D5 and humEN10 mAb IMGT antibodies have activity to inhibit the invasion activity of U937 cells in a dose-dependent manner.
Figure 9B:
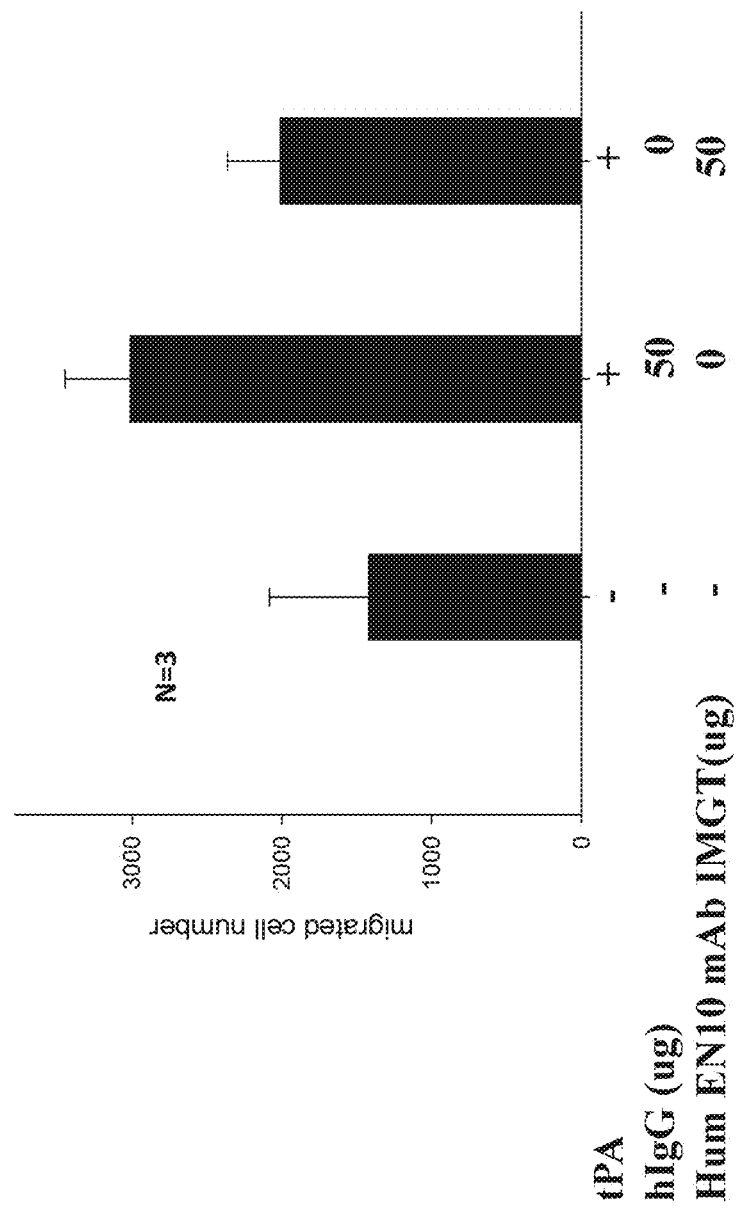

T-test was used to compare activity between each group. P values <0.05 are considered statistically significant. The results are shown in the FIGS. 9A and 9B. As in the study by Wang et al, tPA stimulated the background invasion of U937 (FIGS. 8A and 8B). The invasion activity of U937 was inhibited by about 41.8±11% (N=3) and 33±11% (N=3), when cells were treated with 50 microgram per ml of hum EN10 mAb 45D and EN10 mAb IMGT antibodies, respectively (FIGS. 9A and 9B). These results are similar to those of Example 4. Both humanized antibodies have capability to inhibit the invasion activity of U937 cells.

EXAMPLE 10

Humanized EN10 mAb Inhibits the Dissociation of CL1-5 Cells from Collagen and Fibronectin To assess the signal transduction pathway between ENO1 plasminogen receptor-plasmin and extracellular substrates, 1 mg/ml of gelatin, 100 microgram/ml of fibrinogen, 10 microgram/ml of collagen, and 10 microgram/ml of fibronectin, respectively, were coated on a non-treated ELISA plate overnight. CL1-5 cells ($4 \times 10^4$ cells) were seeded on the plate, and 50 microgram/ml of hum EN10 mAb 4D5 was added to 200 μL of DMEM containing 10% FCS. Cells were incubated at 37° C. for 24 hours and then washed with PBS twice. 10% WST was added and reaction mixtures were incubated at 37° C. for 4 hours. The relative cell numbers in the plate were estimated by the reading of OD450. Each study was repeated three times. Data are presented as mean±SD. T-test was used to compare activity between each group. P values <0.05 are considered statistically significant.

Figure 10A:
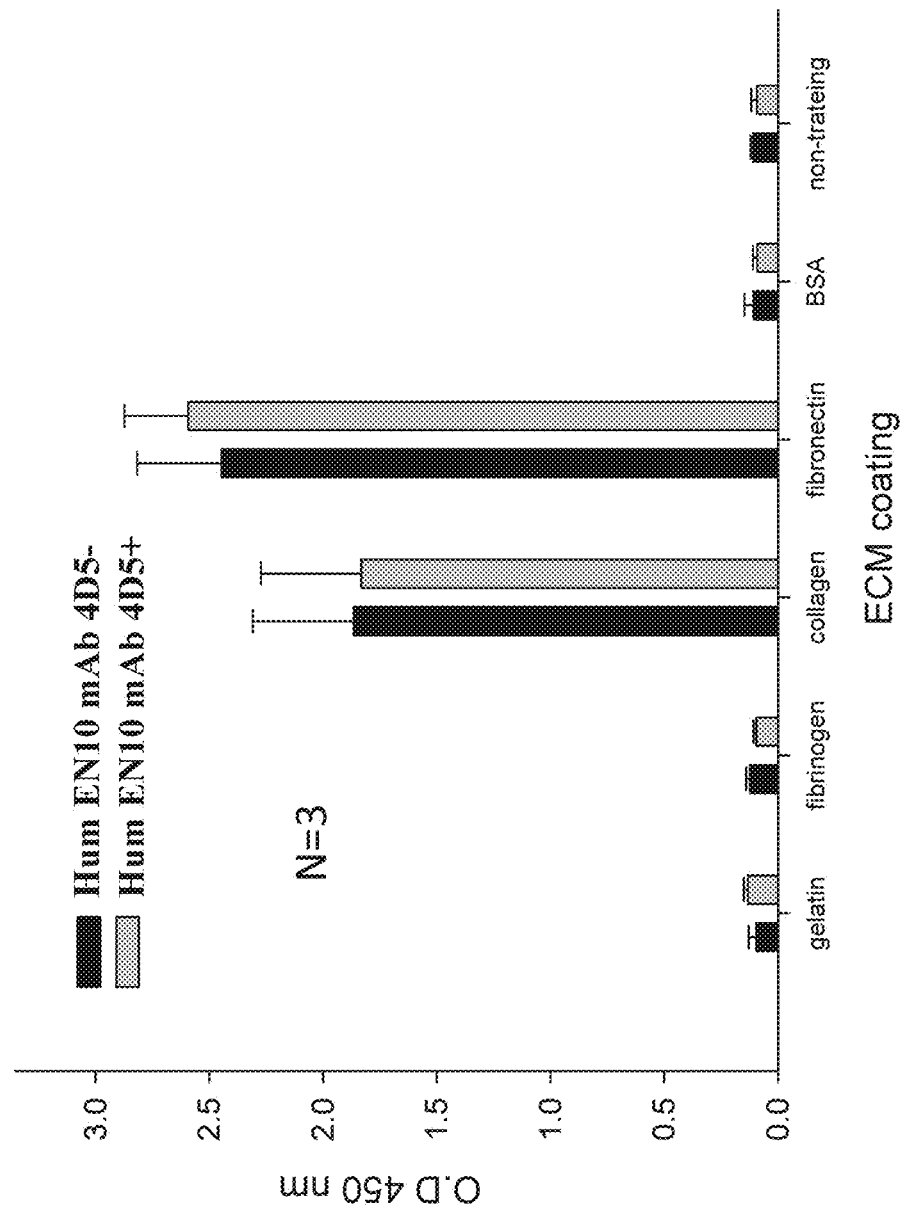
FIG. 10A shows the adhesion activity of CL1-5 lung carcinoma cells to matrix proteins. The adhesion assay was performed as described in Example 10. These data show that CL1-5 cells have higher adhesion activities to collagen and fibronectin.

Results from these experiments are shown in FIG. 10A. These data indicate that OD450 readings on fibronectin and collagen coated plates are 2.45±0.37 (N=3) and 1.83±0.44 (N=3). The readings are much higher than those of gelatin and fibrinogen plates, which are not significantly different from the background reading. There is no significant difference between the hum EN10 mAb 4D5-treated group and the non-treated group. These results suggest that CL1-5 cells favor binding to fibronectin and collagen, and when cells are incubated in the medium without down-stream proteases, for example plasminogen and tPA, the antagonist activity of hum EN10 mAb 4D5 is not involed in the cell association pathway. Data in FIG. 10A also suggests that the ENO1 plasminogen receptor activity is not involved in the cell association with the extracellular matrix.

We further tested whether ENO1 takes part in the cell dissociation from the extracellular matrix. One microgram/ml of fibronectin and 10 microgram/ml of collagen were, respectively, coated on a non-treated ELISA plate overnight. CL1-5 cells ($4 \times 10^4$ cells) were seeded on the plate, and 0, 6.25, 12.5, 25, and 50 microgram/ml of hum EN10 mAb 4D5, respectively, were added to 200 micro L of DMEM containing 10% FCS. Furthermore, 10 microgram/mL Gluplasminogen and 2 nM tPA were added. Cells were incubated at 37° C. for 24 hours and washed with PBS twice. Then, 10% WST was added and reaction mixtures were incubated at 37° C. for 4 hours. The relative cell numbers in the plate were estimated by the readings of OD450. Each study was repeated three times. Data are presented as mean±SD. T-test was used to compare activity between each group. P values <0.05 are considered statistically significant.

Figure 10B:
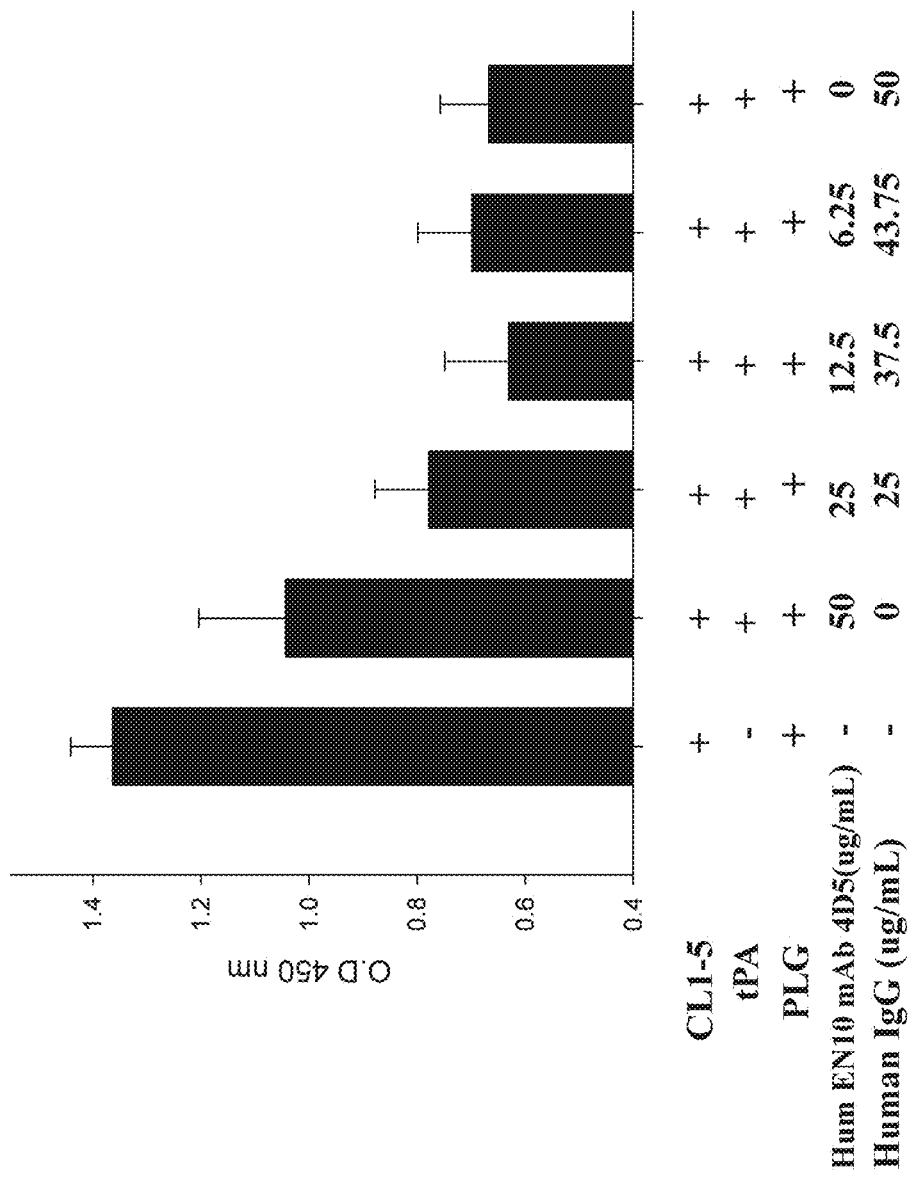
FIG. 10B shows results of inhibition of CL1-5 cell dissociation from fibronectin treated with the humEN10 mAb 4D5. The cell associated adhesion assay was performed as described in Example 10. These data show that the humEN10 mAb 4D5 inhibits the cell dissociation activity of CL1-5 from fibronectin in a dose-dependent manner.
Figure 10C:
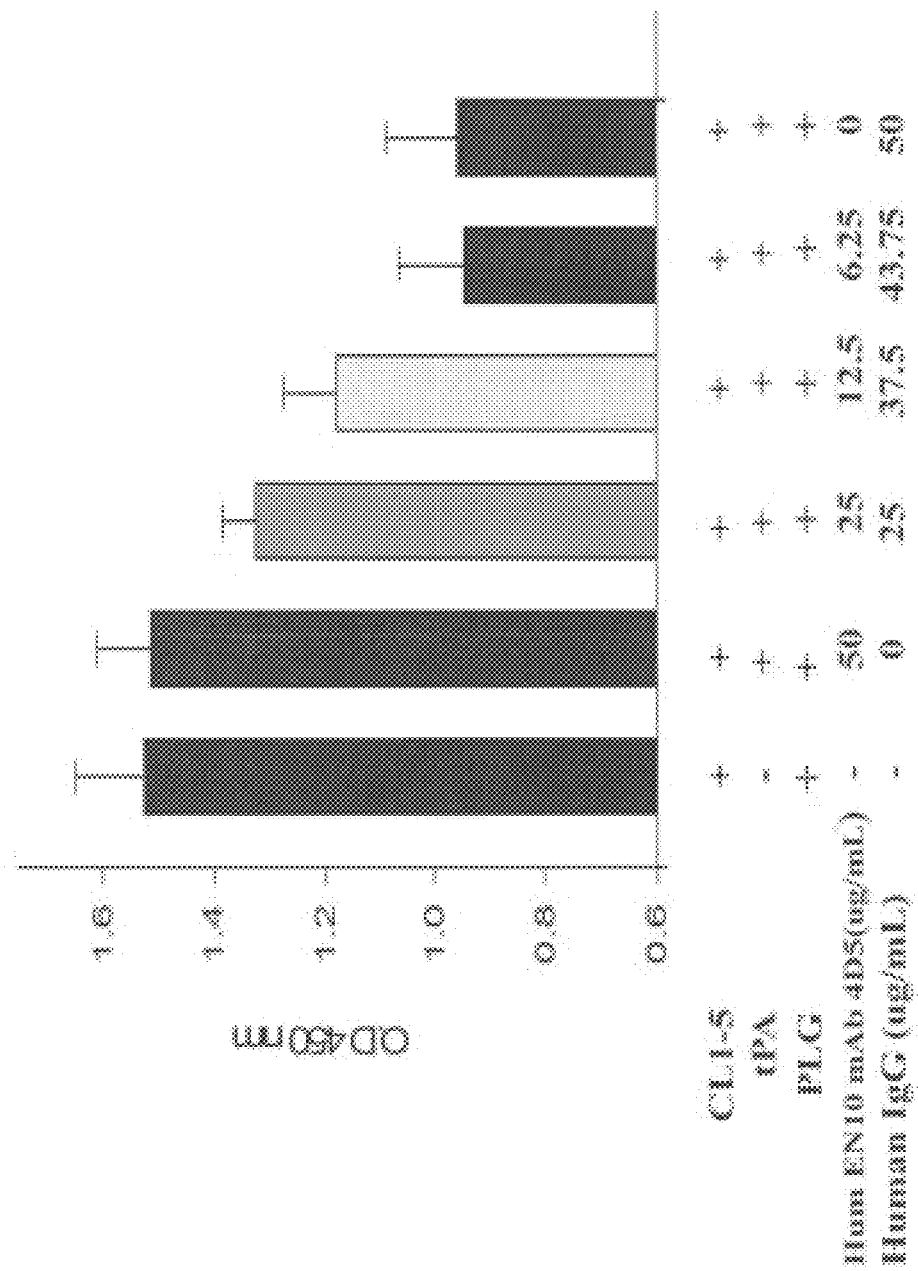
FIG. 10C shows results of inhibition of CL1-5 cell dissociation from collagen treated with the humEN10 mAb 4D5. The cell associated adhesion assay was performed as described in Example 10. These data show that the hum EN10 mAb 4D5 inhibits the cell dissociation activity of CL1-5 from collagen in a dose-dependent manner.

Results from these experiments are shown in FIG. 10B and FIG. 10C. The data indicate that cell numbers are directly proportional to the concentrations of treated hum EN10 mAb 4D5 in both extracellular matrices when the medium contains the ENO1 receptor down-stream proteases plasminogen and tPA. There are significant difference between 50 microgram hum EN10 mAb 4D5-treated group and the control IgG group (P<0.05) in both extracellular matrix studies. These results suggest that ENO1 is involved in the dissociation pathway of CL1-5 cells from extracellular matrixes, presumably by enhancing the plasmin and tPA protease activity. Hum EN10 mAb 4D5, functioning as an antagonist of ENO1, blocks the receptor activity of ENO1, resulting in the inhibition of plasmin and tPA activation and, therefore, inhibits the dissociation activity of CL1-5 cells from extracellular matrixes and invasion.

EXAMPLE 11

Humanized ENO-1 Antibodies Show the ADCC (Antibody Dependent Cell Cytotoxicity) Effect on the Lung Cancer Cell Line It is known that in addition to the anti-growth inhibition, the ADCC of Herceptin is very important for its anti-tumor effect. Because hum EN10 mAb 4D5 and hum EN10 mAb IMGT antibodies have the same Fc fragment of Herceptin, we rationalized that both antibodies have the ADCC activity.

To test the ADCC effect of hum EN10 mAb 4D5 and Hum EN10 mAb IMGT antibodies against cancer cells, $2 \times 10^4$ of human lung CL1-5 cancer cells were grown in 96 ELISA plates. After overnight incubation, different concentrations of hum EN10 mAb 4D5, hum EN10 mAb IMGT and the control IgG1 antibodies were added. Fresh blood samples from 5 volunteers were collected followed the IRB Guide line of DCB. PBMC (peripheral blood mononuclear cell) were prepared by Blood:PBS:FICOLL=1:1:1 solution under 3000 rpm centrifugation for 30 minutes. The resulting PBMCs were collected and washed with PBS twice. PBMCs were suspended in RPMI1640 medium containing 5% FBS and diluted to the concentration with $2.5 \times 10^7$ cells/mL. Then, 50 microliters of PBMC were added to the ELISA plates containing CL1-5. Cells were spun at 3000 rpm for 5 minutes and incubated at 37° C. for 4 hours. Samples were washed with PBS twice and an ADCC detection kit was added followed the protocol provided by manufacturer and incubated at room temperature for 30 minutes. The percentage of cell lysis in the plate was estimated by the reading of OD530/590. Each study was repeated three times. Data are presented as mean±SD.

Figure 11A:
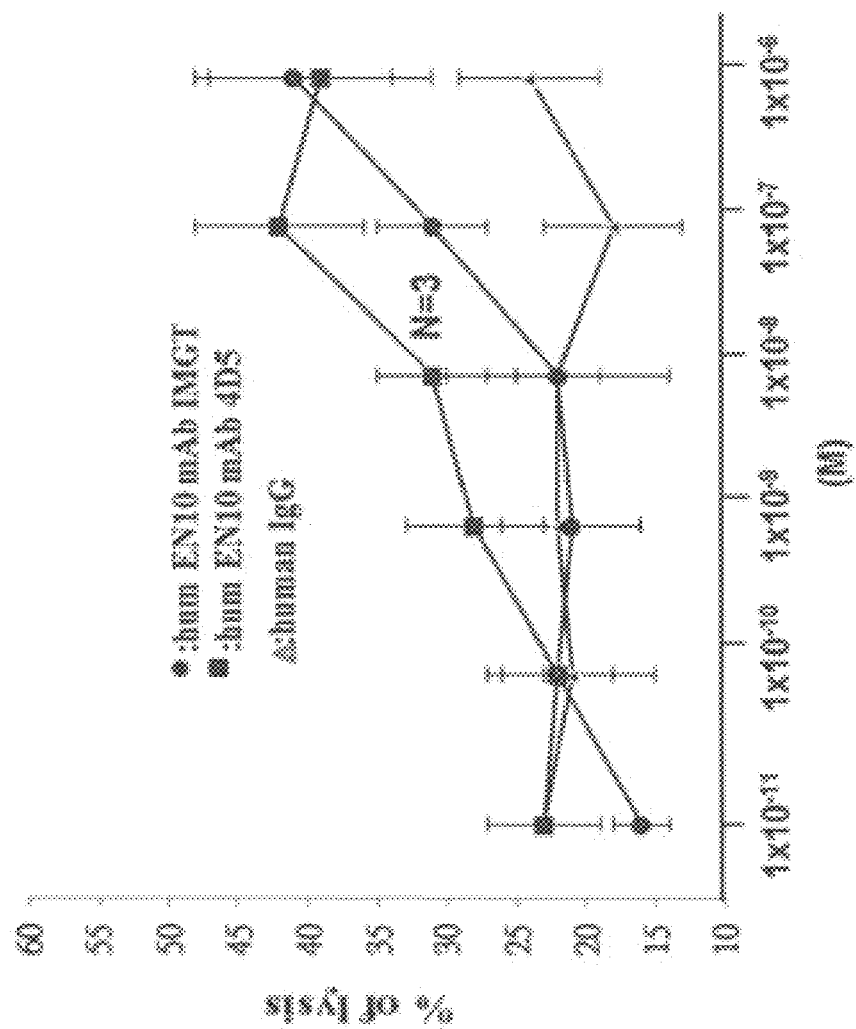
FIGS. 11A and B depict that the antibody-dependent cell-mediated cytotoxicity effects of humEN10 mAb 4D5 and humEN10 mAb IMGT antibodies. The administration of humanized antibodies and cell lysis effects of lung cancer cell line of CL-5 were performed as described in Example 11. The data show that both humanized EN10 antibodies create new ADCC activities.
Figure 11B:
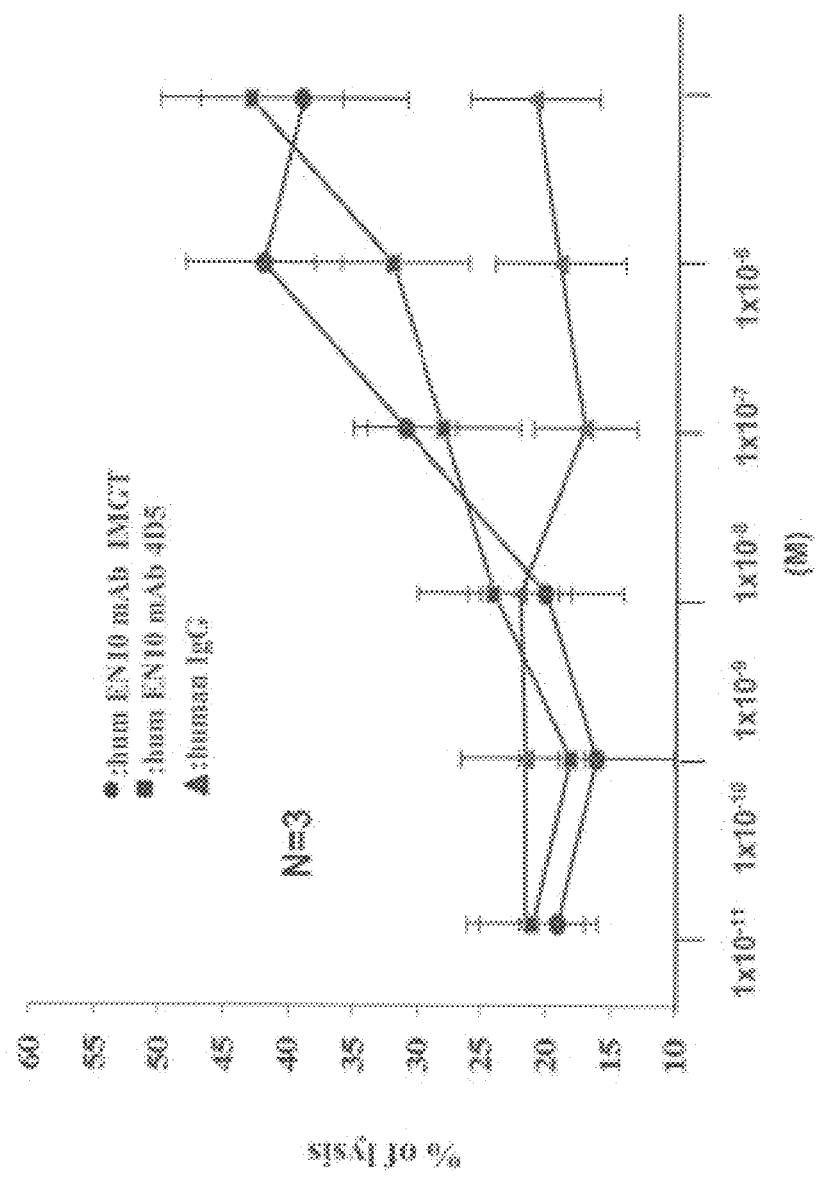

Results from these experiments are shown in FIGS. 11A and 11B. Cell lysis percentage shows no significant increase when cell were treated with different concentrations of control human IgG antibody in the studies with effector/target ratios of 40:1 and 15:1. In the study with an effector/target ratio of 40:1, cells treated with $1 \times 10^{-9}$ M of hum EN10 mAb 4D5 antibody started to see significant lysis difference, as compared with cells treated with the same concentration of human IgG. Both hum EN10 mAb 4D5 and hum EN10 mAb IMGT antibodies showed the maximum lysis activities about 42% when cells were treated with $10^{-6}$M of antibodies. In the study with a low effector/target ratio (15:1), both hum EN10 mAb 4D5 and hum EN10 mAb IMGT antibody groups started to show significant lysis at $1 \times 10^{-8}$ M and reached the maximum lysis at $10^{-6}$M. The ADCC EC50 of hum EN10 mAb 4D5 and hum EN10 mAb IMGT antibodies are estimated to be about $8 \times 10^{-9}$M and $1 \times 10^{-8}$M, respectively. Both humanized EN10 antibodies have the ADCC activities. Our results suggest that in addition to anti-invasion activities, hum EN10 mAb 4D5 and hum EN10 mAb IMGT antibodies can provided the ADCC activity as an anti-cancer agent.

EXAMPLE 12

The Inhibitory Effect of Humanized EN10 Antibodies on Tumor Growth

The humanized EN10 antibody has a good affinity with KD about $2.311 \pm 0.003 \times 10^{-10}$ mol/L and a potential for the further development. To evaluate the therapeutic effects of humanized EN10 antibodies, a CL1-5 mouse xenograft model was performed. CL-5F4 lung adenocarcinoma cells ($1 \times 10^6$ cells/mouse; 5 mice/group) were subcutaneously inoculated at day 0. The therapeutic procedure was performed 2 days after the tumor inoculation by administrating 10 mpk (mg/Kg) of an isotype control (CTL), hum EN10 mAb 4D5 or hum EN10 mAb IMGT antibody twice per week. The tumor volume and bodyweight of each mouse was measured weekly. Data are represented as mean±SD for individual groups.

Figure 12:
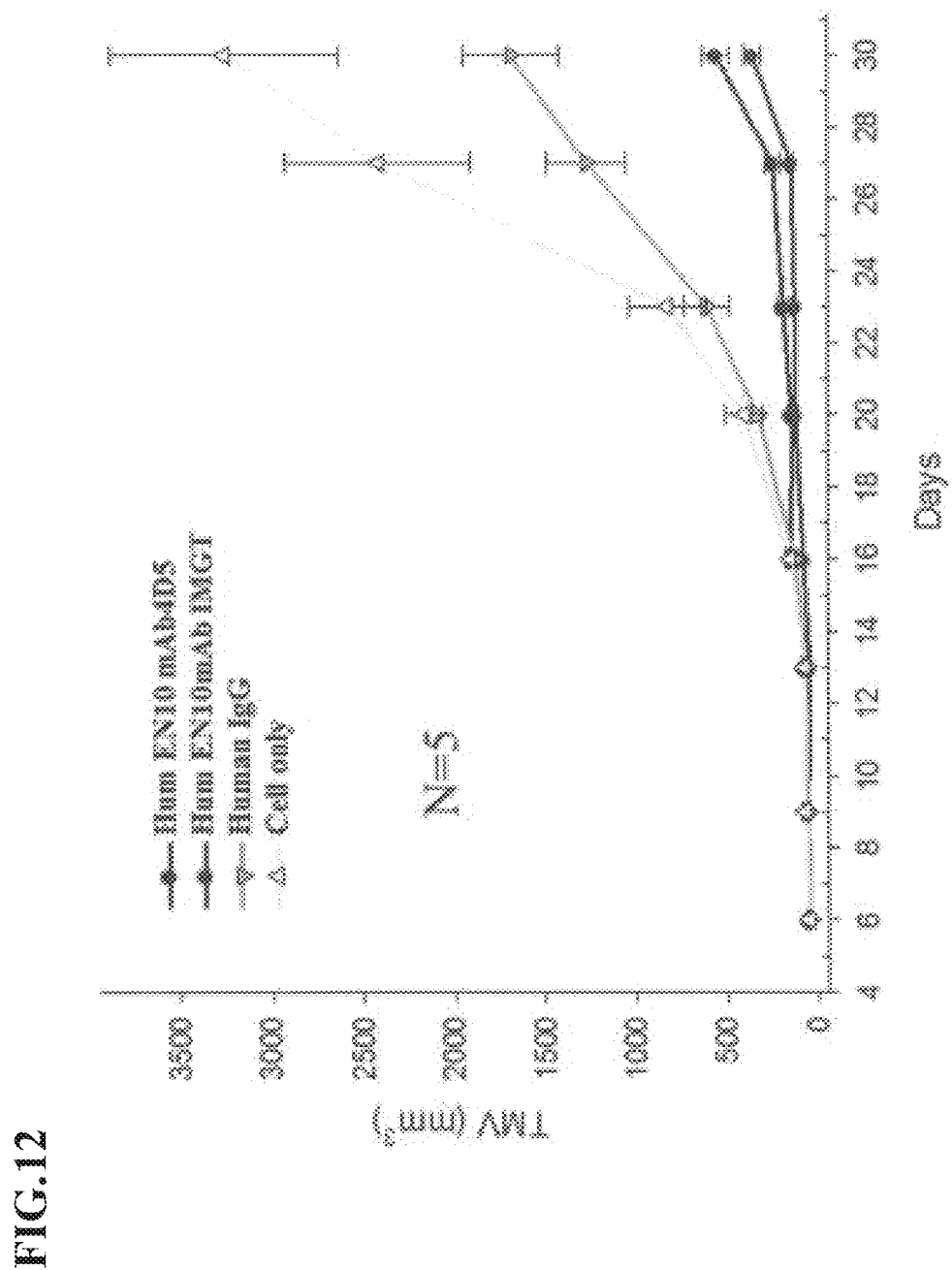
FIG. 12 shows inhibitory effects of humEN10 mAb 4D5 and humEN10 mAb IMGT antibodies. The administration of humEN10 mAb 4D5 and humEN10 mAb IMGT and the retardations of tumor growth by antibody treatments were performed as described in Example 12. The data show that the administration of both humanized EN10 mAbs twice per week has an efficacy in the CL1-5 xenograft mouse model.

The results are shown in FIG. 12. After 2 days, there are no significant tumor size differences among the control, hum EN10 mAb, and hum EN10 mAb IMGT groups. After day 23, the tumor of mice in the control group starts to grow exponentially, and there is no significant tumor growth in the hum EN10 mAb 4D5 and hum EN10 mAb IMGT treatment mice. After day 30, the average tumor size of the control group mice is $1600 \pm 200$ mm$^3$ (N=5), and for mice treated with 10 mpk of hum EN10 mAb 4D5 and hum EN10 mAb IMGT, the average tumor sizes are $505 \pm 24$ mm3 (N=5) and $330 \pm 11$ mm$^3$ (N=5), respectively. The average tumor sizes of both hum EN10 mAb 4D5 and hum EN10 mAb IMGT treatment groups are significantly smaller, as compared to that of the control group with a P value of 0.004 and 0.003, respectively. There are no significant tumor size difference between the hum EN10 mAb 4D5 and hum EN10 mAb IMGT treatment groups. This result indicates that hum EN10 mAb 4D5 and hum EN10 mAb IMGT have the tumor growth inhibition activities on CL1-5 cells in the mouse xenograft model, and EN10 mAbs have good efficacies as reagents for cancer therapy.

EXAMPLE 13

The CHO Cell Codon Optimization

From the examples above, we conclude that ENO1 monoclonal antibodies have potentials for development as a therapeutic antibody.

Figure 13B:
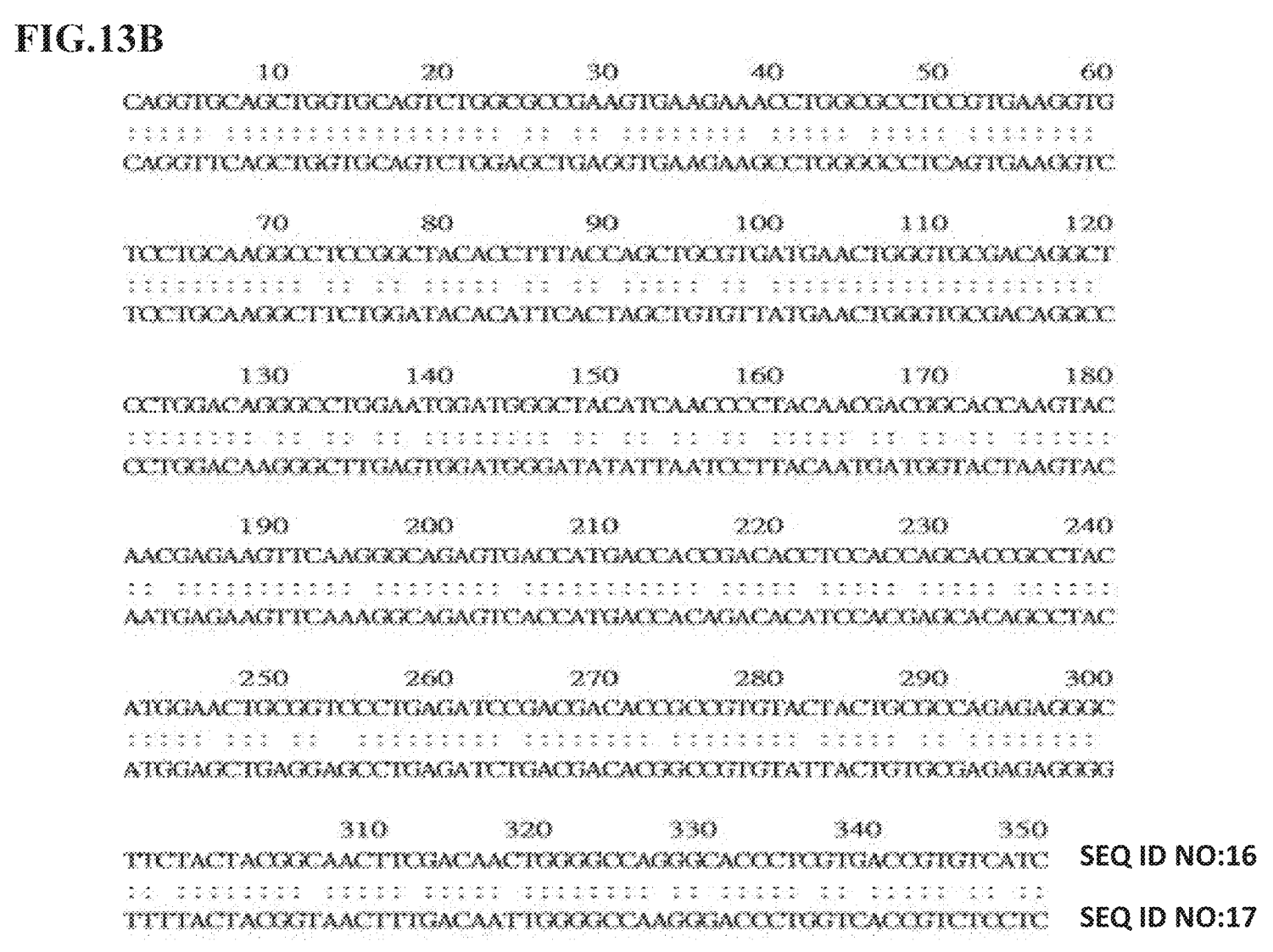

To mass-produce the humanized therapeutic antibody in the CHO cell line, codon optimizations were performed by using the GeneOptimizer® software tool. (http://www.lifetechnologies.com/tw/zt/home/life-science/cloning/gene-synthesis/geneart-gene-synthesis/geneoptimizer.html). The variable region of hum EN10 mAb IMGT was subjected to change and to obtain the optimized codons. The parameters include the codon quality distribution (the quality value of the most frequently used codon for the desired expression system) and GC content (optimizes codon so that GC content is within the desirable range). The codon optimized light chain variable region and heavy chain variable region for the CHO cell line show in FIG. 13A and FIG. 13B, respectively.

Figure 13C:
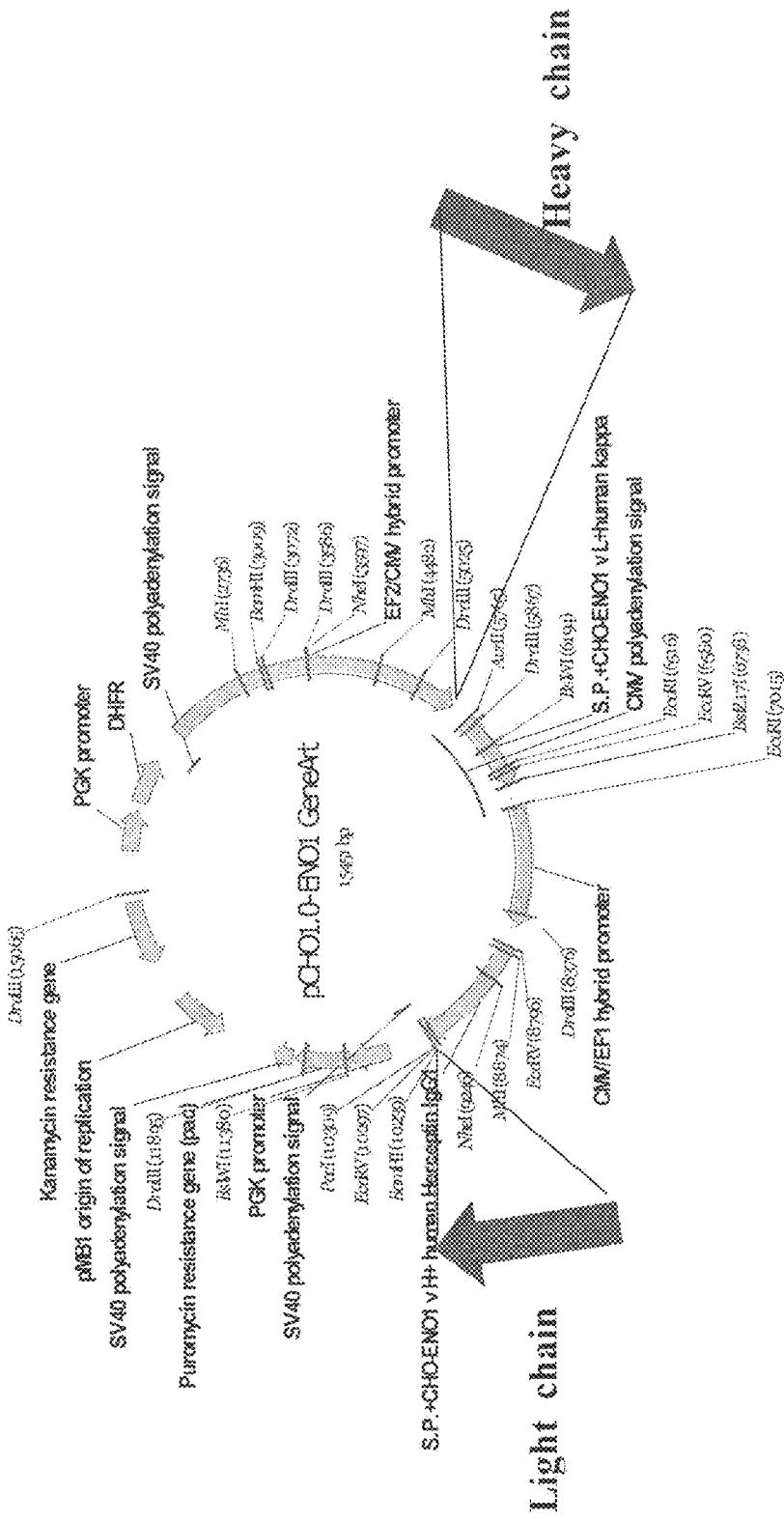
FIG. 13C depicts an expression vector for the generation of humanized antibody of humEN10 IMGT in the CHOS stable cell line. Detailed procedures were performed as described in Example 13.

The CHO cell codon optimized variable regions of light chain and heavy chains of hum EN10 mAb IMGT was directly generated by the nucleotide synthesis method, respectively. Then the variable regions of hum EN10 mAb IMGT and a human Herceptin® Fc antibody expression vector pCHO-ENO1, as shown in FIG. 13C, were introduced into host cells to prepare recombinant antibody-expressing cells. As the host cells for expression, the CHOS cells (from Life-Technology Inc.) were used. The vector was introduced into the host cells by lipofectamine 2000 in accordance with the included instruction manual (manufactured by Invitrogen). About 2.5 microgram of the antibody expression vector was linearized by restriction enzymes, the gene was introduced into $4 \times 10^6$ cells, and cells were inoculated to a 6-well culture plate. For low concentration selection, resulting cell pools were grown in the selection medium containing 10 microgram/ml of puromycin and 100 nano molar of methotrexate or 20 microgram/ml of puromycin and 200 nano molar of methotrexate. To perform further selection, the other stage of high concentration selection was performed. The primary selection pools were further grown in the medium containing 30 microgram/ml of puromycin and 500 nano molar of methotrexate or in the medium containing 50 microgram/ml of puromycin and 1000 nano molar of methotrexate. To generate a final antibody production cell line, 96,000 cells from the second stage pools were inoculated in semisolid medium, and 768 high antibody-expression cells were determined and picked by the fluorescence intensity performed in the ClonePix2 in accordance with the instruction manual protocol (manufactured by Molecular Device Inc.). The top 10 high lead cell lines were selected with parameters including growth rates, 5-day batch production rates, and 14-day simple-fed batch production rates. After 60-generations of stability tests, the candidate production cell line was determined.

The results are shown the FIG. 13A. When the nucleic acid sequence of the hum EN10 mAb IMGT, the codons of which were optimized into the CHO cell expression system by the GeneOptimizer® software tool, was aligned with that of human original, the homologies of variable light chain and variable heavy chain between the two editions are 74.5% and 84%, respectively. This result indicates that the codon preferences between human cells and CHO cells are different, even when the encoded antibodies have the same protein sequence.

Figure 13E:
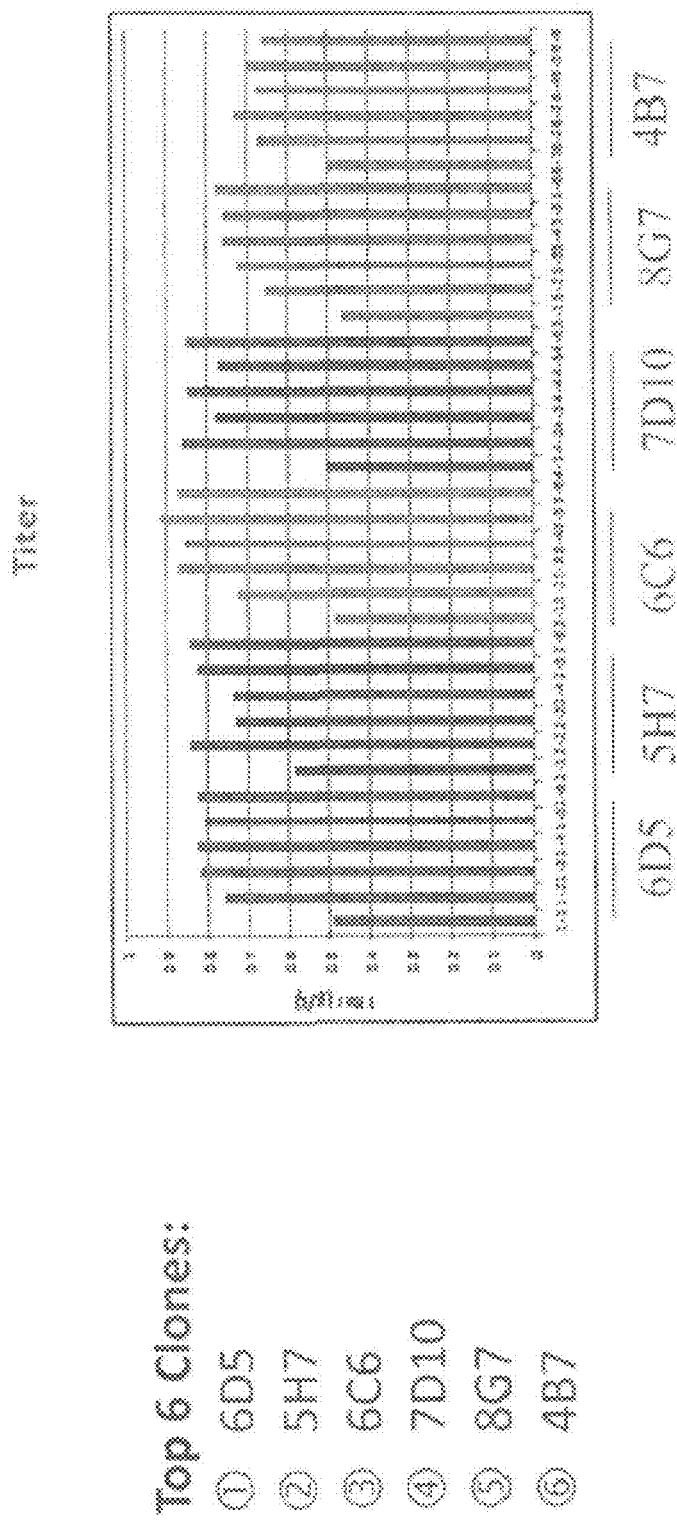
FIG. 13E shows the productivity of top 6 CHOS stable clones which expressed humEN10 IMGT mAb antibody. Detail procedures were performed as described in Example 13. Our data shows that after the codon optimization and single colony selection, the production rates of these 6 top clones are close to 1 g/L/15 days.
Figure 13F:
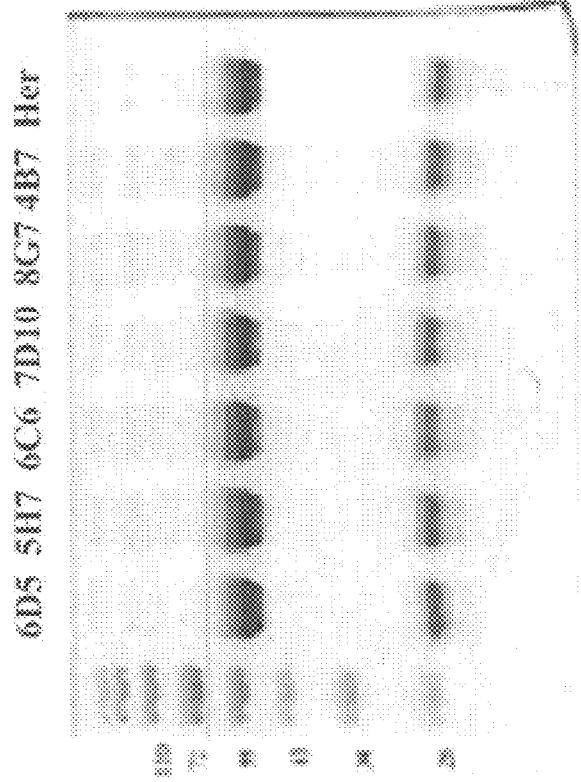
FIG. 13F shows the SDS PAGE of antibodies isolated from top 6 stable clones which expressed humEN10 mAb IMGT antibody. Detailed procedures were performed as described in Example 13. Our data shows that all of these clones express intact hum EN10 mAb IMGT.

When both editions of antibody genes were constructed into pCHO1.0 and transiently expressed in CHO cells, the antibody production rate of the CHO cell codon edition is about 3.1 times of that of human original (data not shown). Our result suggests that the codon optimization is important for the high yield production of antibodies. The cell pools of CHO optimized hum ENO10 mAb IMGT were further selected in the ForiCHO medium (Life Technology Inc) and high antibody production cell lines were picked with a ClonePix2. When the production rates of top 15 clones on days 5 and 14 were analyzed, the results are shown in the FIG. 13D. The production rates ranges from 91.3 minigram/liter to 155 minigram/liter on the day 5 and from 247.5 minigram/liter to 358.7 minigram/liter on the day 14. All of these clones have good viability and growth rate in the simple medium. These results suggest that all of clones may improve their antibody production capability after medium optimization. To further explore the antibody productivity of these clones, different combinations of glucose and feed medium studies were performed and the antibody production rates were analyzed in the top 6 clones on the day 15. The result was shown in FIG. 13E. The maximum production rate of the top 6 clones ranges from 0.7 gram per liter to 0.81 gram per liter after 15 days incubation. All clones have good stability after 60-generation analysis and produce intact antibody when the antibodies were analyzed by SDS PAGE (FIG. 13F). Our study suggests that these clones have good potentials as ENO1 therapeutic antibody production cell lines.

EXAMPLE 14

Characterization of Hum EN10 mAb IMGT Antibody

To understand the structure of CHO cell expressed hum ENO10 mAb, SEC-HPLC and Mass spectrum analyses were performed. For intact mass analysis, 30 μg of protein was dissolved in 30 μl dH$_2$O in 0.1% formic acid. For reduced mass analysis, 30 μg of protein in 15 μl dH$_2$O was treated with 10 mM DTT at 80° C. for 15 mins. The reduced protein was diluted to the final concentration with 1 μg/μl in 0.1% formic acid of 30 μl dH$_2$O. For the deglycosylated mass analysis, 30 μg of protein were treated with 0.6 μl PNGase F (P0705L, NEB) in 50 mM ammonia bicarbonate at 37° C. overnight. Then, the sample was analyzed by the procedures described as intact mass analysis and reduced mass analysis, respectively.

For SEC-HPLC analysis, samples were subjected to the Shimadzu Pump LC-20AD with conventional PDA and monitored at 280 nm Waters UPLC H-class Biosystem with the separation column, Sepax Zenix SEC-300BEH C4 (2.17.8 mm×300 mm, 1.7 μm). The composition of solution A was 0.1 M sodium phosphate and 0.1 M sodium sulfate adjusted to pH 6.8 in water. The mobile phase was isogradient with 100% solution A in 35 minutes. Separation samples from SEC-HPLC were collected and subjected to the Mass spectrum analysis as follows.

For LC/Mass spectrum analysis, samples were subjected to the Waters UPLC H-class Biosystem with the separation column BEH C4 (2.1 mm×150 mm, 1.7 μM). The composition of solution A and B were 0.1% formic acid in water and acetonitrile, respectively. The mobile phase was gradient with 5 to 58% of solution B in 15 minutes. Separation samples from UPLC were connected directly to the ESI-MS instrument Synapt G2-Si (Waters Inc. Milford. Mass. USA). The Mass spectrum was linked to ESI. The data were collected by way of 1 second MS per cycle until the scanning was ended. Data were processed by Unifi™ (V1.8) including the Fasta Format data bank which was focused on sequences of antibodies. After deconvolution, the experimental data were compared to the deduced molecular weight of the antibody. All data were triplicated from three batches.

If the antibody is cysteinated and glutathionated, the molecular weight of both types of products will be increased by about 119 Da and 305 Da, respectively.

The results are shown in FIGS. 14A and 14B. In addition to the mass spectrum peaks of G0F2, G1F/G0F, and G1F/G1F forms of hum EN10 mAb antibody, an extra molecule with additional molecular weight about 119 Da appears in the spectrum of three batches of expressed hum ENO10 mAb. It is hypothesized that cysteinylation on the G$_0$F2 form of hum ENO10 mAb happens (FIG. 14A). To further confirm the cysteinylation of humEN10 mAb antibody, the same batches of hum EN10 mAb antibody digested by PNGase F and LC/Mass spectrum assays were performed. The results are shown in FIG. 14 B. In addition to the mass spectrum of unglycosylated hum EN10 mAb antibody, two extra mass spectrum peaks with additional molecular weights of about 119 Da and 305 Da, which are predicted to be cysteinylation and glutathionylation of the antibody, appear. This result further supports that hum EN10 mAb antibody is not only cysteinylated, but also glutathionylated. The composition of cysteinylation of 3 batches of humEN10 mAb antibody is shown in Table III. The averages of cysteinylation and glutathionylation of humEN10 mAb are about 17.8% and 6.6%, respectively (Table III).

TABLE III the percentage of cysteinylation and glutathionylation of three batches of hum EN10 mAb IMGT antibody

| Antibody forms | batch number | | |
|---|---|---|---|
| | Lot 1 | Lot2 | Lot3 |
| Native (%) | 64 | 80 | 83 |
| Cysteinylation (%) | 29 | 12 | 12 |
| Glutathionylation (%) | 6.6 | 7.8 | 5.4 |

EXAMPLE 15

The Generation of Alanine32 and Serine32 Mutants in HCDR1 of Humen10 mAb Antibody The results of Example 14 suggest that there are cysteinylation and glutathionylaltion in our expressed humEN10 mAb antibody. Mcsherry's study indicates that the cysteinylation of a monoclonal antibody leads to its inactivation. (MAbs. 2016, 8:718-25.) These reactions also induce the heterogeneity of expressed antibodies and result in CMC problems of clinical therapeutic antibodies. To elucidate the cysteinylation and glutathionylation sites of humEN10 mAb antibody, the amino acid sequences of humEN10 mAb antibody were analyzed. The cysteine 32 in HCDR1 was found to be uncoupled in the protein. To learn whether this cysteine is involved in the cysteinylation and glutathionylation of humEN10 mAb, two mutants of humEN10 mAb antibody were generated, by mutating cysteine 32 of HCDR1 to alanine and serine, respectively, using site-directed mutagenesis.

Primers:

```
ENO1-HC(AvrII)-f:
                                 (SEQ ID NO: 18)
TCGCCTAGGGCCACCATGGGTTGGAGCCTCATCTTG

ENO1-HCDR1C-(SA)-R:
                                 (SEQ ID NO: 19)
TCGCACCCAGTTCATCACGGMGCTGGTAAAGGTGTAGCC

ENO1-afHCDR1-C-F:
                                 (SEQ ID NO: 20)
GTGATGAACTGGGTGCGACAG

ENO1-HC(BstZ17I)-r:
                                 (SEQ ID NO: 21)
TTAGTCGTATACTCAGCCAGGAGACAGAGACAGG
```

For amplification of each mutant, two reaction solutions having a composition of 3 μL of template DNA about 30 ng, 5 μL of 10× reaction Buffer, 1 μL of 10 mM dNTP mix, 1 μL of 2.5 unit pfu polymerase, 12.5 μL of 125 ng forward primer, and 12.5 μL of 125 ng reverse primer was prepared in a final volume of 50 μL with double distilled water and subjected to PCR. For the reaction 1, the forward primer and reverse primer are ENO1-HC(AvrII)-F and ENO1-HCDR1C-(SA)-R. For reaction 2, the forward primer and reverse primer are ENO1-afHCDR1-C-F and ENO1-HC (BstZ17 I)-r. A cycle of 95° C. for 10 minutes was used, then a cycle of 95° C. for 30 seconds, 55° C. for 30 seconds, and 68° C. for 6 minute was repeated 35 times. After the PCR reaction, every mutation clone with the right sequences was subjected to 2% agarose gel electrophoresis. The DNA fragment of each mutant was isolated from the agarose gel and purified by Gene Clean Kit in accordance with the included instruction manual provided by the manufacturer (BIO101).

To amplify the full length mutants, 3 μL of template DNA containing the products of reaction 1 (1900 bp) and 2 (1260 bp) described above, 5 μL of 10× reaction buffer, 1 μL of 10 mM dNTP mix, 1 μL of 2.5 unit pfu polymerase, 12.5 μL of 125 ng forward primer (ENO1-HC(AvrII)-F), and 12.5 μL of 125 ng reverse primer (ENO1-HC(BstZ17I)-r.) was prepared in a final volume of 50 μL with double distilled water and subjected to PCR. The PCR conditions were the same as described above. The reaction product was digested by restriction enymes AvrI and Bst17I and inserted into the AvrI and Bst17I sites of pCHO 1.0 ENO1 containing the light chain gene of humEN10 mAb antibody. Primers (herpIgG1-F9501 5'-CACAAGCCTTCCAACACCAAGGTGGA-CAA-3' (SEQ ID NO:22) and herpIgG1-R9700 5'-TC-CTCGTGGGACACGTCCACCACCACGCA-3' (SEQ ID NO:23) were then used to determine the nucleotide sequence. Every mutation clone plasmids with right sequences were transformed into *E. coli* DH5α. To confirm the affinity change after the antibodies was mutated, the alanine (EN10.4) and serine (EN10.5) mutants of humEN10 mAb antibody were introduced into host cells to prepare recombinant antibody-expressing cells. As the host cells for expression, the FreeStyle293 cells (manufactured by Invitrogen) were used. The vector was introduced into the host cells by lipofectamine 2000 in accordance with the included instruction manual (manufactured by Invitrogen.) About 2.5 microgram of the antibody expression vector was linearized by restriction enzymes, the gene was introduced into $4 \times 10^6$ cells, and cells were inoculated to a 6-well culture plate. The agent corresponding to a selection marker of the expression vector was added, and cells were continuously cultured to form a stable pool.

A culture supernatant containing human IgG antibody was prepared by the method described below. The antibody-producing cells were acclimated in a Freestyle™ 293 Expression Medium (GIBCO). The cells were cultured in a tissue culture flask, and the culture supernatant was collected when the viable rate of the cells was 90%. The collected supernatant was filtered through 10 micrometer and 0.2 micrometer filters (manufactured by Millpore) to remove contaminants. The culture supernatant containing the antibody was affinity-purified using Protein A (manufactured by Millipore), using PBS as an absorption buffer and 20 mM sodium citrate buffer (pH 3.0) as an elution buffer. The elution fractions were adjusted to around pH 6.0 by adding 50 mM sodium phosphate buffer (pH 7.0). The prepared antibody solution was replaced with PBS using a dialysis membrane (10,000 MW cutoff, manufactured by Spectrum Laboratories) and filter-sterilized through a membrane filter (manufactured by Millpore) having a pore size of 0.22 micrometer to yield the purified antibody. The concentration of the purified antibody was determined by measuring the absorbance at 280 nm and converting the measured value based on 1.45 optimal density equaling 1 mg/ml.

To determine the binding activity of each mutant antibody, 400 ng/100 μL of human ENO1 protein was coated on a 96-well ELISA overnight at 4° C. and the plate further was washed by PBS. The plate was blocked with 1% BSA (w/v) in PBS at room temperature for 1 hour, then washed again with 1×PBS. EN10.4, EN10.5, and humEN10 mAb antibodies were 2-fold serial diluted to 15 different concentrations and added to the plate at 37° C. for 1 hour. After the reaction was complete, the plate was washed 3 times with 1×PBS. A 1/8000 dilution of goat anti-human-HRP antibody was added and incubated at 37° C. for 1 hour, and then the plate washed 3 times with 1×PBS. The TMB substrate was added and reacted at room temperature for 30 minutes. The reaction was stopped by adding 1N HCl, and OD 450 was read to determine the activity. Every study was repeated three times. Data are presented as mean±SD. OD readings and concentrations of antibody were used to make a multiple scatter figure by Sigmaplot. The $K_D$ values were predicted by four parameter logistic fit.

Figure 15:
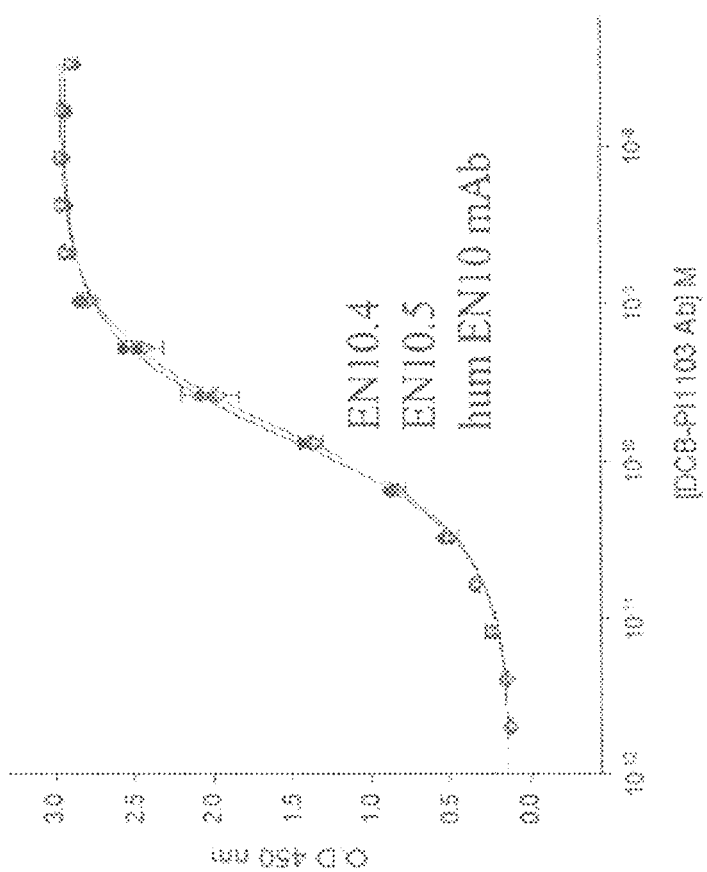
FIG. 15 depicts results from using humEN10 mAb IMGT. EN10.4 and EN10.5 antibodies to determine binding affinities and kinetic constants of alanine 32 and serine 32 of variable region of heavy chain HCDR1, respectively.

The results of this experiment are shown in FIG. 15. The $K_D$ values of EN10.4, EN10.5, and humEN10 mAb antibodies were $1.40 \pm 0.05 \times 10^{-10}$ (N=3), $1.57 \pm 0.06 \times 10^{-10}$ (N=3) and $1.63 \pm 0.06 \times 10^{-10}$ (N=3), respectively. There is no significant affinity difference among three different editions of hum EN10 mAb antibodies. Our data suggest that mutations of cysteine HCDR1 of hum EN10 mAb to serine or alanine do not significantly change the affinity of antibodies. Due to the structure similarity between cysteine and serine, EN10.5 is chosen to generate antibody production cell lines.

EXAMPLE 16

The Generation of Production CHO Cell Line of EN10.5

To know whether the cysteine 32 in HCDR1 of humEN10 mAb antibody is important for cysteinylation and glutathionylation, the EN10.5 antibody gene was constructed into pCHO 1.0, and introduced into host cells to prepare recombinant antibody-expressing cells. As the host cells for expression, the CHOS cells (Life-Technology Inc.) were used. The vector was introduced into the host cells by lipofectamine 2000 in accordance with the included instruction manual (manufactured by Invitrogen.) About 2.5 microgram of the antibody expression vector was linearized by restriction enzymes, the gene was introduced into $4 \times 10^6$ cells, and cells were inoculated into a 6-well culture plate. For low concentration selection, resulting cell pools were grown in the selection medium containing 10 microgram/ml of puromycin and 100 nano molar of methotrexate or 20 microgram/ml of puromycin and 200 nano molar of methotrexate. To do the further selection, the other stage of high concentration selection was performed. The primary selection pools were further grown in the medium containing 30 microgram/ml of puromycin and 500 nano molar of methotrexate or in the medium containing 50 microgram/ml of puromycin and 1000 nano molar of methotrexate. To generate the final antibody production cell line, 96,000 cells from the second stage pools were inoculated on a semisolid medium, and 768 high antibody expression cells were determined and picked by the fluorescence intensity performed in the ClonePix2 in accordance with the instruction manual protocol (manufactured by Molecular Device Inc.). The top 20 high lead cell lines were selected with parameters including growth rates, 5-day batch production rates, and 14-day simple-fed batch production rates. When the production rates of top 20 clones on days 14 were analyzed, the results are shown in the FIG. 16. The production rate ranges from 344.5 mg/liter to 735.2 gram/liter on day 14. Our result suggests that the average productivity of EN10.5 is more than 2 folds of that of humEN10 mAb antibody. All of these clones have good viabilities and growth rates in the simple medium. These results imply that all of clones may improve their antibody production capability after medium optimization. To further explore the antibody productivity of these clones, different combinations of glucose and feed medium studies were performed, and the antibody productions rates were analyzed in the top one clone on the day 15. The result shows that the maximum production rate of the top clone ranges from 2 grams per liter to 2.5 grams per liter after 15 days incubation. All clones have good stability after 60-generation analysis and produce intact antibody when the antibodies were analyzed by SDS PAGE. Our study suggests that EN10.5 without the cysteinylation site has a better productivity as compared with that of hum EN10 mAb antibody.

EXAMPLE 17

Characterization of EN10.5 Antibody

To understand the structure and homogeneity of CHO cell expression EN10.5 mAb, SEC-HPLC and Mass spectrum analyses were performed. For intact mass analysis, 30 µg of protein was dissolved in 30 µl dH$_2$O containing 0.1% formic acid. For reduced mass analysis, 30 µg of protein in 15 µl dH$_2$O was treated with 10 mM DTT at 80° C. for 15 mins. The reduced protein was diluted to the final concentration with 1 µg/µl in 30 µl dH$_2$O in 0.1% formic acid. For the deglycosylated mass analysis, 30 µg of protein were treated with 0.6 µl PNGase F (P0705L, NEB) in 50 mM ammonia bicarbonate at 37° C. overnight. Then, the sample was analyzed by the procedures described as intact mass analysis and reduced mass analysis, respectively.

For SEC-HPLC analysis, samples were subjected to Waters UPLC H-class Biosystem with the separation column BEH C4 (2.1 mm×150 mm, 1.7 um). The composition of solution A and B were 0.1% formic acid in water and acetonitrile, respectively. The mobile phase was gradient with 5 to 58% of solution B in 15 minutes. Separation samples from SEC-HPLC were connected to perform the Mass spectrum analysis.

For SEC-HPLC analysis, samples were subjected to Shimadzu Pump LC-20AD with conventional PDA and monitored at 280 nM with the separation column, Sepax Zenix SEC-300 (7.8 mm×300 mm, 1.7 um). The composition of solution A was 0.1M sodium phosphate and 0.1M sodium sulfate adjusted to pH6.8 in water. The mobile phase was isogradient with 100% solution A in 35 minutes. Separation samples from SEC-HPLC were collected and subjected to the Mass spectrum analysis as follows.

For LC/Mass spectrum analysis, samples were injected to the Waters UPLC H-class Biosystem with the separation column BEH C4 (2.1 mm×150 mm, 1.7 µm). The compositions of solutions A and B were 0.1% formic acid in water and acetonitrile, respectively. The mobile phase was gradient with 5 to 58% of solution B in 15 minutes. Separation samples from UPLC were connected directly into the ESI-MS instrument, Synapt G2-Si (Waters Inc. Milford. Mass. USA). If the antibody is cysteinylated and glutathionylated, the molecular weights of both types of antibodies will be increased by about 119 Da and 305 Da, respectively.

The results are shown in FIGS. 17A and 17B. As typical glycan profiles of antibodies, there are G$_0$F, G$_1$F, and G$_1$×2F of the mass spectrum peaks in CHO cell expressed EN10.5 antibody. Unlike the hum EN10 mAb, we were unable to find any cysteinylation peak in this clone. It is hypothesized that all cysteines are coupled in EN10.5 after HCDR1 cysteine 32 is mutated to serine. To further confirm the cysteinylation of EN10.5 antibody, the same batch of EN10.5 mAb antibody was digested by PNGase F, and LC/Mass spectrum analyses were performed. The results are shown in FIG. 17 B. Unlike in the mass spectrum of unglycosylated humEN10 mAb antibody, two extra mass spectrum peaks with additional molecular weights of about 119 Da and 305 Da were absent in EN10.5 mAb. Our result indicates that there are no cysteinylation and glutathionylation in EN10.5 mAb and further supports that hum EN10 mAb antibody is not only cysteinylated, but also glutathionylated. After HCDR1 cysteine 32 is mutated to serine, the cysteinylation and gluthionylation are compromised in the EN10.5 mAb antibody. The resultant antibody are more homogeneous and higher productivity than that of hum EN10 mAb, and has high potential as a candidate of therapeutic antibody.

EXAMPLE 18

Antibody Epitope Mapping

To determine the epitope of EN10 mAb on the human ENO1 protein, two forward primers with the nucleotide sequences of 5'-GGATCCGCAGCAAACTTCA-GGGAAGCCATG-3' (SEQ ID NO:24), and 5'-GGATC-CTCGAAGATCCCCTTTGACCAGGATG-3' (SEQ ID NO:25), and a reverse primer (5'-TCAGGCT-GAAAATCTCTCATCCGC-3' (SEQ ID NO:26) were designed. An *E. coli* expression plasmid pTRC-HIS ENO1 containing human ENO1 cDNA gene was used as a template to amplify ENO1 deletion mutants. Primers with SEQ NO:24 and SEQ NO:25 were used as forward primers, with the SEQ ID NO:26 as a reverse primer, to amplify deletion mutants 1-182 and 1-293, respectively. The other set of primers, having the sequences of 5'-GGATCCTATCTAT-TCTCAAGATCCATGCC-3' (SEQ ID NO:27) and 5'-CTC-GAGGTCATGGTGTCTCATCGTTCGCTCGAG-3' (SEQ ID NO:28), was used to amplify a deletion 373-434 mutant. For amplification of each mutant, a reaction solution having a composition of 1 microL of 1:1000 dilution of template DNA about 0.1 ng, 5 microL of 10× reaction buffer, 1 microL of 10 mM dNTP mix, 1 microL of 2.5 unit Taq polymerase, 1 microL of the forward primer, and 1 microL of the reverse primer was prepared in a final volume of 50 microL with double distilled water and subjected to PCR. A cycle of 94 degree C. for 10 minutes was used, then a cycle of 94 degree C. for one minute, 52 degree C. for one minute, and 72 degree C. for 1 minute was repeated 35 times, and the reaction was incubated at 72 degree C. for 10 more minutes. This reaction solution was subjected to 2% agarose gel electrophoresis to analyze the reaction products. Reaction products with the correct molecular weights were ligated into a pCR 2.1-TOPO vector (manufactured by Invitrogen) for subcloning in accordance with the attached instruction manual. M13 forward (5'-GTAAACAACGACGGCGAG-3' (SEQ ID NO: 12)) and M13 reverse (5'-CAGGAAACAGC-TATGAC-3' (SEQ ID NO: 13)) primers were then used to determine the nucleotide sequence. Every mutation clone with the correct sequences was digested with restriction enzymes BamHI and XhoI, and the digestion products were subjected to 2% agarose gel electrophoresis. The insertion fragment of each mutant was digested from the agarose gel and purified with a Gene Clean Kit in accordance with the attached instruction manual provided by the manufacturer (BIO101). The BamHI and XhoI DNA fragment of each mutant was ligated to the BamHI and XhoI sites of a *E. coli* expression vector pTRC His A (Invitrogen). The resulting plasmid was transformed into *E. coli* BL21 Rosseta. The ENO1 mutation protein was expressed in *E. coli* by IPTG induction and purified by Ni-agarose in accordance with the attached instruction manual provided by the manufacturer (Qiagen) after the bacteria pellet was sonicated. The purity of each mutant was analyzed by 12% SDS PAGE. To determine the binding activity of each mutant protein, 400 ng of human ENO1 protein was coated on a 96-well ELISA plate and plate was washed by PBS, 10 microgram of EN10 mAb was added to the plate and the plate was incubated at 37° C. for 1 hours. After the binding complex was washed with PBS twice, a goat anti-mouse IgG conjugated with HPRT was added, After 1 hours incubation, TMB was added. The binding affinity was determined by the readings of OD 405. Each study was repeated three times. Data are presented as mean±SD. T-test was used to compare activity between each group. P values <0.05 were considered statistically significant.

The results are shown in FIG. 18A. ENO1 mutants 1-189 and 1-297 have OD405 readings about 1.43±0.18 and 1.56±0.08 (N=3), which are about 42% and 39% of that of the wild type ENO1 (2.87±0.08) (N=3), respectively. However, when amino acid residues from 297 to 434 were deleted, the binding activity of this mutated ENO1 to EN10 mAb was lost, as compared with the BSA background. These results suggest that amino acid residues from 297 to 434 are required for ENO1 protein binding to EN10 mAb and the decrease in the binding activity of mutants 1-189 and 1-297 may be due to the instability or conformation change of the mutant proteins.

To further explore the epitope of EN10 mAb in the ENO1 protein, 5 reverse primers, having sequences of 5'-CTCGA-GAGGGATCTTCGATAGACACCACTGGG-3' (SEQ ID NO:29), 5'-CTCGAGCTACCTGGATTCCTGCACTG-GCTG-3' (SEQ ID NO:30), 5'-CTCGAGACTTCTCGT-TCACGGCCTTGGCGATC-3' (SEQ ID NO:31), 5'-CTC-GAGACTTCTCGTTCACGGCCTTGGCGATCC-3' (SEQ ID NO:32), 5'-CTCGAGCAGTCTCCCCCGAACGAT-GAGACACC-3' (SEQ ID NO:33), and 5'-CTCGAGCAC-CAGTCTTGATCTGCCCAGTGCAC-3' (SEQ ID NO:34) were designed. An *E. coli* expression plasmid pTRC-HIS ENO1 containing human ENO1 cDNA gene was used as a template to amplify the ENO1 deletion mutants. SEQ ID NO:27 were used as the forward primer to amplify deletion mutants 296-434, 316-434, 336-434, 376-434 and 396-434 with the SEQ ID NO:29, SEQ ID NO:30, SEQ ID NO:31, SEQ ID NO:32, SEQ ID NO:33, and SEQ ID NO:34 primers, respectively. For amplification of each mutant, a reaction solution having a composition of 1 microL of 1:1000 dilution of template DNA about 0.1 ng, 5 microL of 10× reaction buffer, 1 microL of 10 mM dNTP mix, 1 microL of 2.5 unit Taq polymerase, 1 microL of forward primer, and 1 microL of reverse primer was prepared in a final volume of 50 microL with double distilled water and subjected to PCR. A cycle of 94 degree C. for 10 minutes was used. Then, a cycle of 94 degree C. for one minute, 52 degree C. for one minute, and 72 degree C. for 1 minute was repeated 35 times, and the reaction was incubated at 72 degree C. for 10 more minutes. This reaction solution was subjected to 2% agarose gel electrophoresis to analyze the reaction products. Reaction products with the correct molecular weights were ligated into a pCR 2.1 I-TOPO vector (manufactured by Invitrogen) for subcloning in accordance with the attached instruction manual. M13 forward (5'-GTAAACAACGACGGCGAG-3' (SEQ ID NO:12) and M13 reverse (5'-CAGGAAACAGCTATGAC-3' (SEQ ID NO:13) primers were then used to determine the nucleotide sequence. Every mutation clone with the correct sequence was digested with restriction enzymes BamHI and XhoI and the digestion product was subjected to 2% agarose gel electrophoresis. The DNA fragment of each mutant was isolated from the agarose gel and purified with a Gene Clean Kit in accordance with the attached instruction manual provided by the manufacturer (BIO101). The BamHI and XhoI DNA fragment of each mutant was ligated into the BamHI and XhoI sites of an *E. coli* expression vector pTRC His A (Invitrogen). The resulting plasmid was transformed into *E. coli* BL21 Rosseta. The ENO1 mutation protein was expressed in *E. coli* by IPTG induction and purified by Ni-agarose in accordance with the attached instruction manual provided by the manufacturer (Qiagen) after the bacteria pellet was sonicated. The purity of each mutant was analyzed by 12% SDS PAGE. To determine the binding activity of each mutant protein, 400 ng of human ENO1 protein or mutant protein was coated on a 96-well ELISA plate and plate was washed by PBS. 10 microgram of EN10 mAb was added and incubated at 37° C. for 1 hours. After the binding complex was washed with PBS twice, a goat anti-mouse IgG conjugated with HPRT was added. After 1 hour incubation, TMB was added. The binding affinity was determined by the readings of OD 405. Each study was repeated three times. Data are presented as mean±SD. T-test was used to compare activity between each group. P values <0.05 are considered statistically significant.

The 12% of SDS PAGE of each mutant and the wild type protein are shown in the FIG. 18B. The molecular weight of each mutant increases from the mutant 296-434 to the wild type. This result suggests that we can yield the whole protein from each mutant even though some degradation of mutants 336-434 and 376-434 can be seen. As showed in the FIG. 18C, there is no significant difference between the EN10 mAb binding affinity of the wild type ENO1 and those of deletion mutants 336-434, 376-434, and 396-434. However, when amino acid residues from 296 to 434 and 316 to 434 are deleted, the EN10 mAb binding activities of these two ENO1 mutants are lost, as compared with that the *E. coli* cell lysate background. These results suggest that amino acid residues from 296 to 336 (FDQDDWGAWQKFTASAG-IQVVGDDLTVTNPKRIAKAVNEKS, SEQ ID NO.39) are important for ENO1 protein binding with EN10 mAb.

EXAMPLE 19

Alanine Scanning

To further explore which residues from 296 to 336 of human ENO1 are important for EN10.5 mAb binding, the crystal structure of ENO1 was downloaded from protein data bank (pdb-entry: 2PSN). After the structure analysis, amino acid residues Q298, D299, S310, G312, and R327 are predicted to be exposed on the protein surface and are candidates for mutations to analyze whether they are indeed important for EN10.5 binding. All of these 5 residues were chosen to be mutated to alanine using the QuickChange II site-directed mutagenesis Kit in accordance with the attached instruction manual provided by the manufacturer (Agilent Technology). The following mutagenic oligonucleotides for alanine scanning (Table IV) were generated by Genomics BioScience and Technology Co., Ltd.

TABLE IV

| Oligo Sequences: |
|---|
| 5'-AGCTCCCCAGTCATCCGCGTCAAAGGGATCTTCG-3'- (SEQ ID NO: 35) |
| 5'-CGAAGATCCCTTTGACGCGGATGACTGGGGAGCT-3' (SEQ ID NO: 36) |
| 5'-ATCCCTTTGACCAGGCTGACTGGGGAGCTTG-3' (SEQ ID NO: 37) |
| 5'-CAAGCTCCCCAGTCAGCCTGGTCAAAGGGAT-3' (SEQ ID NO: 38) |

TABLE IV-continued

Oligo Sequences:

5'-CTACCTGGATTCCTGCAGCGGCTGTGAACTTCTGCC-3'
(SEQ ID NO: 42)

5'-GGCAGAAGTTCACAGCCGCTGCAGGAATCCAGGTAG-3'
(SEQ ID NO: 43)

5'-CCACTACCTGGATTGCTGCACTGGCTGTG-3'
(SEQ ID NO: 44)

5'-CACAGCCAGTGCAGCAATCCAGGTAGTGG-3'
(SEQ ID NO: 45)

5'-ACGGCCTTGGCGATCGCCTTTGGGTTGGTCAC-3'
(SEQ ID NO: 46)

5'-CCTGCACTGGCTGTGAACGCCTGCCAAGCTCCCC-3'
(SEQ ID NO: 47)

5'-GTGACCAACCCAAAGGCGATCGCCAAGGCCGT-3'
(SEQ ID NO: 48)

For amplification of each mutant, a reaction solution having a composition of 3 µL. of template DNA about 30 ng, 5 µL of 10× reaction buffer, 1 µL of 10 mM dNTP mix, 1 µL of 2.5 unit pfu polymerase, 12.5 µL of 125 ng forward primer, and 12.5 µL of 125 ng reverse primer was prepared in a final volume of 50 µL with double distilled water and subjected to PCR. A cycle of 95° C. for 10 minutes was used. Then, a cycle of 95° C. for 30 seconds, 55° C. for 30 seconds, and 68° C. for 6 minute was repeated 16 times. After the PCR reaction, 1 µL of DpnI was added to each PCR tubes, incubated at 37° C. for 1 hour and then DpnI was heated to be inactivated at 80° C. for 20 minutes. The reaction products were transformed to 50 µL XL1-Blue competent cells in accordance with the attached instruction manual (manufactured by Invitrogen). An ENO1 R400-420 primer (5'-GCAAGGGGCACCAGTCTTGATCTG-3' (SEQ ID NO:49)) was used to determine the nucleotide sequence. Every mutation clone plasmids with right sequences were transformed to E. coli BL21 Rosseta. The ENO1 mutation protein was expressed in E. coli by IPTG induction and purified by Ni-agarose in accordance with the attached instruction manual provided by the manufacturer (Qiagen) after the bacteria pellet was sonicated. The purity of each mutant protein was analyzed by 12% SDS PAGE.

To determine the binding activity of each mutant protein, 400 ng/100 µL of human ENO1 protein or mutated ENO1 protein was coated on a 96-well ELISA plate and incubated overnight at 4° C. and the plate was washed with PBS. The plate was blocked with 1% BSA (w/v) in PBS at room temperature for 1 hour, then washed again with 1×PBS. A primary antibody (EN10.5 mAb) was 2-fold serial diluted to 15 different concentrations and added to the plate at 37° C. for 1 hour. After the reaction was done, the plate was washed 3 times with 1×PBS. A 1/8000 dilution of goat anti-mouse-HRP antibody was added and incubated at 37° C. for 1 hour, then the plate was washed 3 times with 1×PBS. Then, TMB substrate was added and the reaction was allowed to proceed at room temperature for 30 minutes. The reaction was stopped by adding 1N HCl and OD450 was read to determine the activity. Each study was repeated three times. Data are presented as mean±SD. OD readings and concentrations of antibody were used to make a multiple scatter plot using Sigmaplot™. The KD values were predicted by four parameter logistic fit.

According to the ENO large portion deletion study results shown in Example 18, a peptide sequence FDQDDW-GAWQKFTASAGIQVVGDDLTVTNPKRIAKAVNEKS (SEQ ID NO.39) from the residue number 296 to 336 is required for the binding of ENO1 protein and EN10 mAb. Thus, the crystal structure of ENO1 was downloaded from protein data bank (pdb-entry: 2PSN) to analyze residue positions from this region. There are 5 amino acid residues including Q298, D299, S310, G312, and R327 exposed on the protein surface (FIG. 19A, putative epitope). Through the site-direct mutagenesis, these 5 amino acids were mutated and the resulting mutant proteins were expressed in E. coli and purified, respectively (FIG. 19B). Every purified ENO1 mutant protein was analyzed for any KD changes by ENO1 binding in ELISA. The results indicate that there are three functional classes of amino acid residues in these mutants. Amino acid residues R327 are required for the binding between ENO1 protein and EN10.5 mAb. If R327 acid residue is mutated to alanine, the binding activity of this ENO1 mutant to EN10.5 mAb is lost. The second class of amino acid residue belongs to D299. If D299 is mutated to alanine, the binding activity of this ENO1 mutant to EN10.5 mAb is compromised. The rest of amino acid residues including Q298, S310, and R312 belong to the group of amino acids residues which have no significant binding effect on ENO1 protein binding to EN10.5 mAb if they are mutated (FIG. 19C). These results suggest that D299 and R327 are important for the protein and protein binding between ENO1 and EN10.5 mAb. In sum, the same as their parent antibodies EN10 mAb, hum EN10 mAb 4D5, hum EN10 mAb IMGT and EN10.5 mAb use their ENO1 plasminogen receptor antagonist activities to inhibit the plasminogen activation, thereby inducing down regulation of protease activity on the cell surface, which in turn results in the inhibition of dissociation of cancer cells from extracellular matrix. As a result, antibodies against ENO1 can inhibit the invasion capability of cancer cells. These data support that ENO1 antibodies (e.g., EN10 mAb) have favorable affinities, efficacies and potentials as therapeutic antibodies for the treatment of cancers.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A antibody, or an antigen-binding fragment thereof, that binds human ENO1, comprising (i) a light chain variable region (VL) comprising LCDR1 (RASENIYSYLT; SEQ ID NO: 6), LCDR2 (NAKTLPE; SEQ ID NO: 7) and LCDR3 (QHHYGTPYT; SEQ ID NO: 8), and (ii) a heavy chain variable region (VH) comprising HCDR1 (GYTFTS-Xaa-VMN, wherein Xaa is serine or alanine; SEQ ID NO: 50), HCDR2 (YINPYNDGTKYNEKFKG; SEQ ID NO: 4) and HCDR3 (EGFYYGNFDN; SEQ ID NO: 5).

2. The antibody, or the antigen-binding fragment thereof, according to claim 1, wherein the VL comprises SEQ ID NO: 2 or 9.

3. The antibody, or the antigen-binding fragment thereof, according to claim 1, wherein the VH comprises SEQ ID NO: 51.

4. A pharmaceutical composition comprising a therapeutically effective amount of the antibody, or the antigen-binding fragment thereof, according to claim 1, and a pharmaceutically acceptable carrier.

5. A method for treating a subject suffering from an ENO1 protein-related disease or disorder, comprising administering a therapeutically effective amount of the antibody, or the antigen-binding fragment thereof, according to claim 1 to the subject.

6. The method of claim 5, wherein the ENO1 protein-related disease or disorder is a neoplastic disease, or an inflammatory disease or immune disorder.

7. The method of claim 6, wherein the neoplastic disease is lung cancer, breast cancer, pancreas cancer, liver cancer, colorectal cancer, or prostate cancer.

8. The method of claim 6, wherein the inflammatory disease or immune disorder is multiple sclerosis, rheumatoid arthritis, Crohn's disease, ulcerative colitis, systemic Lupus erythematosus, chronic obstructive pulmonary disease (COPD), asthma, allergy, psoriasis, type 1 diabetes mellitus, atherosclerosis or osteoporosis.

9. A method for inhibiting cancer invasion in a subject in need thereof, comprising administering a therapeutically effective amount of the antibody, or the antigen-binding fragment thereof, according to claim 1 to the subject.

10. The method according to claim 5, wherein the VH of the antigen, or the antigen-binding fragment thereof, comprises SEQ ID NO: 51.

* * * * *

SEQUENCE LISTING

<160> NUMBER OF SEQ ID NOS: 51

<210> SEQ ID NO 1
<211> LENGTH: 119
<212> TYPE: PRT
<213> ORGANISM: Mus musculus -continued

```
<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Cys
            20                  25                  30

Val Met Asn Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Phe Tyr Tyr Gly Asn Phe Asp Asn Trp Gly Gln Gly
            100                 105                 110

Thr Thr Leu Thr Val Ser Ser
        115

<210> SEQ ID NO 2
<211> LENGTH: 108
<212> TYPE: PRT
<213> ORGANISM: Mus musculus

<400> SEQUENCE: 2

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Thr Trp Tyr Gln Gln Lys Gln Gly Lys Ser Pro Gln Leu Leu Val
        35                  40                  45

Tyr Asn Ala Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Tyr
                85                  90                  95

Thr Phe Gly Gly Gly Thr Lys Leu Glu Ile Thr Arg
            100                 105

<210> SEQ ID NO 3
<211> LENGTH: 10
<212> TYPE: PRT
<213> ORGANISM: Mus musculus

<400> SEQUENCE: 3

Gly Tyr Thr Phe Thr Ser Cys Val Met Asn
1               5                   10

<210> SEQ ID NO 4
<211> LENGTH: 17
<212> TYPE: PRT
<213> ORGANISM: Mus musculus

<400> SEQUENCE: 4

Tyr Ile Asn Pro Tyr Asn Asp Gly Thr Lys Tyr Asn Glu Lys Phe Lys
1               5                   10                  15

Gly
```

<210> SEQ ID NO 5
<211> LENGTH: 10
<212> TYPE: PRT
<213> ORGANISM: Mus musculus

<400> SEQUENCE: 5

Glu Gly Phe Tyr Tyr Gly Asn Phe Asp Asn
1               5                   10

<210> SEQ ID NO 6
<211> LENGTH: 11
<212> TYPE: PRT
<213> ORGANISM: Mus musculus

<400> SEQUENCE: 6

Arg Ala Ser Glu Asn Ile Tyr Ser Tyr Leu Thr
1               5                   10

<210> SEQ ID NO 7
<211> LENGTH: 7
<212> TYPE: PRT
<213> ORGANISM: Mus musculus

<400> SEQUENCE: 7

Asn Ala Lys Thr Leu Pro Glu
1               5

<210> SEQ ID NO 8
<211> LENGTH: 9
<212> TYPE: PRT
<213> ORGANISM: Mus musculus

<400> SEQUENCE: 8

Gln His His Tyr Gly Thr Pro Tyr Thr
1               5

<210> SEQ ID NO 9
<211> LENGTH: 108
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Thr Trp Tyr Gln Gln Lys Pro Gly Lys Ala Pro Lys Leu Leu Ile
        35                  40                  45

Tyr Asn Ala Lys Thr Leu Pro Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Tyr
                85                  90                  95

Thr Phe Gly Gln Gly Thr Lys Leu Glu Ile Lys Arg
            100                 105

<210> SEQ ID NO 10
<211> LENGTH: 119
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Cys
            20                  25                  30

Val Met Asn Trp Val Arg Gln Ala Pro Gly Lys Gly Leu Glu Trp Val
        35                  40                  45

Ala Tyr Ile Asn Pro Tyr Asn Asp Gly Thr Lys Tyr Asn Glu Lys Phe
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Phe Tyr Tyr Gly Asn Phe Asp Asn Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Cys
            20                  25                  30

Val Met Asn Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Phe Tyr Tyr Gly Asn Phe Asp Asn Trp Gly Gln Gly
            100                 105                 110

Thr Leu Val Thr Val Ser Ser
        115

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
gtaaacaacg acggcgag         18

<210> SEQ ID NO 13
<211> LENGTH: 17
<212> TYPE: DNA
<213> ORGANISM: Artificial Sequence
<220> FEATURE:
<223> OTHER INFORMATION: Synthetic

<400> SEQUENCE: 13

```
caggaaacag ctatgac                                                      17

<210> SEQ ID NO 14
<211> LENGTH: 323
<212> TYPE: DNA
<213> ORGANISM: Artificial Sequence
<220> FEATURE:
<223> OTHER INFORMATION: Synthetic

<400> SEQUENCE: 14
gacatccaga tgacccagtc cccctccagc ctgtctgcct ctgtgggcga cagagtgacc        60
atcacctgtc gggcctccga aacatctac tcctacctga cctggtatca gcagaagccc       120
ggcaaggccc ccaagctgct gatctacaac gccaagaccc tgcccgaggg cgtgccctct      180
agattctccg gctctggctc tggcaccgac tttaccctga ccatcagctc cctgcagccc      240
gaggacttcg ccacctacta ctgccagcac cactacggca ccccctacac ctttggccag      300
ggcaccaagg tggaaatcaa gcg                                              323

<210> SEQ ID NO 15
<211> LENGTH: 323
<212> TYPE: DNA
<213> ORGANISM: Artificial Sequence
<220> FEATURE:
<223> OTHER INFORMATION: Synthetic

<400> SEQUENCE: 15
gatatccaga tgacccagtc ccccagctcc ctgtccgcct ctgtgggcga tagggtcacc       60
atcacctgcc gagcaagtga gaatatttac agttatttaa catggtatca acagaaacca      120
ggaaaagctc cgaaactact gatttacaat gcaaaaacct taccagaagg agtcccttct      180
cgcttctctg gttccggctc tgggacggat ttcactctga ccatcagcag tctgcagccg      240
gaagacttcg caacttatta ctgtcaacat cattatggta ctccgtacac gttcggacag      300
ggtaccaagg tggagatcaa acg                                              323

<210> SEQ ID NO 16
<211> LENGTH: 356
<212> TYPE: DNA
<213> ORGANISM: Artificial Sequence
<220> FEATURE:
<223> OTHER INFORMATION: Synthetic

<400> SEQUENCE: 16
caggtgcagc tggtgcagtc tggcgccgaa gtgaagaaac tggcgcctc cgtgaaggtg        60 tcctgcaagg cctccggcta cacctttacc agctgcgtga tgaactgggt gcgacaggct      120
cctggacagg gcctggaatg gatgggctac atcaacccct acaacgacgg caccaagtac      180
aacgagaagt tcaagggcag agtgaccatg accaccgaca cctccaccag caccgcctac      240
atggaactgc ggtccctgag atccgacgac accgccgtgt actactgcgc cagagagggc      300
ttctactacg gcaacttcga caactggggc cagggcaccc tcgtgaccgt gtcatc          356

<210> SEQ ID NO 17
<211> LENGTH: 356
<212> TYPE: DNA
<213> ORGANISM: Artificial Sequence
<220> FEATURE:
<223> OTHER INFORMATION: Synthetic

<400> SEQUENCE: 17
```

```
caggttcagc tggtgcagtc tggagctgag gtgaagaagc ctggggcctc agtgaaggtc      60
tcctgcaagg cttctggata cacattcact agctgtgtta tgaactgggt gcgacaggcc     120
cctggacaag ggcttgagtg gatgggatat attaatcctt acaatgatgg tactaagtac     180
aatgagaagt tcaaaggcag agtcaccatg accacagaca catccacgag cacagcctac     240
atggagctga ggagcctgag atctgacgac acggccgtgt attactgtgc gagagagggg     300
ttttactacg gtaactttga caattggggc caagggaccc tggtcaccgt ctcctc         356
```

<210> SEQ ID NO 18
<211> LENGTH: 36
<212> TYPE: DNA
<213> ORGANISM: Artificial Sequence
<220> FEATURE:
<223> OTHER INFORMATION: Synthetic

<400> SEQUENCE: 18

```
tcgcctaggg ccaccatggg ttggagcctc atcttg                                36
```

<210> SEQ ID NO 19
<211> LENGTH: 39
<212> TYPE: DNA
<213> ORGANISM: Artificial Sequence
<220> FEATURE:
<223> OTHER INFORMATION: Synthetic

<400> SEQUENCE: 19

```
tcgcacccag ttcatcacgg mgctggtaaa ggtgtagcc                             39
```

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20

```
gtgatgaact gggtgcgaca g                                                21
```

<210> SEQ ID NO 21
<211> LENGTH: 34
<212> TYPE: DNA
<213> ORGANISM: Artificial Sequence
<220> FEATURE:
<223> OTHER INFORMATION: Synthetic

<400> SEQUENCE: 21

```
ttagtcgtat actcagccag gagacagaga cagg                                  34
```

<210> SEQ ID NO 22
<211> LENGTH: 29
<212> TYPE: DNA
<213> ORGANISM: Artificial Sequence
<220> FEATURE:
<223> OTHER INFORMATION: Synthetic

<400> SEQUENCE: 22

```
cacaagcctt ccaacaccaa ggtggacaa                                        29
```

<210> SEQ ID NO 23
<211> LENGTH: 29
<212> TYPE: DNA
<213> ORGANISM: Artificial Sequence
<220> FEATURE:
<223> OTHER INFORMATION: Synthetic

```
<400> SEQUENCE: 23
tcctcgtggg acacgtccac caccacgca                                          29

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
ggatccgcag caaacttcag ggaagccatg                                         30

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25
ggatcctcga agatcccttt gaccaggatg                                         30

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
tcaggctgaa aatctctcat ccgc                                               24

<210> SEQ ID NO 27
<211> LENGTH: 29
<212> TYPE: DNA
<213> ORGANISM: Artificial Sequence
<220> FEATURE:
<223> OTHER INFORMATION: Synthetic

<400> SEQUENCE: 27
ggatcctatc tattctcaag atccatgcc                                          29

<210> SEQ ID NO 28
<211> LENGTH: 33
<212> TYPE: DNA
<213> ORGANISM: Artificial Sequence
<220> FEATURE:
<223> OTHER INFORMATION: Synthetic

<400> SEQUENCE: 28
ctcgaggtca tggtgtctca tcgttcgctc gag                                     33

<210> SEQ ID NO 29
<211> LENGTH: 32
<212> TYPE: DNA
<213> ORGANISM: Artificial Sequence
<220> FEATURE:
<223> OTHER INFORMATION: Synthetic

<400> SEQUENCE: 29
ctcgagaggg atcttcgata gacaccactg gg                                      32

<210> SEQ ID NO 30
```

<211> LENGTH: 30
<212> TYPE: DNA
<213> ORGANISM: Artificial Sequence
<220> FEATURE:
<223> OTHER INFORMATION: Synthetic

<400> SEQUENCE: 30
ctcgagctac ctggattcct gcactggctg                                   30

<210> SEQ ID NO 31
<211> LENGTH: 32
<212> TYPE: DNA
<213> ORGANISM: Artificial Sequence
<220> FEATURE:
<223> OTHER INFORMATION: Synthetic

<400> SEQUENCE: 31
ctcgagactt ctcgttcacg gccttggcga tc                                32

<210> SEQ ID NO 32
<211> LENGTH: 33
<212> TYPE: DNA
<213> ORGANISM: Artificial Sequence
<220> FEATURE:
<223> OTHER INFORMATION: Synthetic

<400> SEQUENCE: 32
ctcgagactt ctcgttcacg gccttggcga tcc                               33

<210> SEQ ID NO 33
<211> LENGTH: 32
<212> TYPE: DNA
<213> ORGANISM: Artificial Sequence
<220> FEATURE:
<223> OTHER INFORMATION: Synthetic

<400> SEQUENCE: 33
ctcgagcagt ctcccccgaa cgatgagaca cc                                32

<210> SEQ ID NO 34
<211> LENGTH: 32
<212> TYPE: DNA
<213> ORGANISM: Artificial Sequence
<220> FEATURE:
<223> OTHER INFORMATION: Synthetic

<400> SEQUENCE: 34
ctcgagcacc agtcttgatc tgcccagtgc ac                                32

<210> SEQ ID NO 35
<211> LENGTH: 34
<212> TYPE: DNA
<213> ORGANISM: Artificial Sequence
<220> FEATURE:
<223> OTHER INFORMATION: Synthetic

<400> SEQUENCE: 35
agctccccag tcatccgcgt caaagggatc ttcg                              34

<210> SEQ ID NO 36
<211> LENGTH: 34
<212> TYPE: DNA
<213> ORGANISM: Artificial Sequence
<220> FEATURE:
<223> OTHER INFORMATION: Synthetic

<400> SEQUENCE: 36

```
cgaagatccc tttgacgcgg atgactgggg agct                                    34
```

<210> SEQ ID NO 37
<211> LENGTH: 31
<212> TYPE: DNA
<213> ORGANISM: Artificial Sequence
<220> FEATURE:
<223> OTHER INFORMATION: Synthetic

<400> SEQUENCE: 37

```
atccctttga ccaggctgac tggggagctt g                                       31
```

<210> SEQ ID NO 38
<211> LENGTH: 31
<212> TYPE: DNA
<213> ORGANISM: Artificial Sequence
<220> FEATURE:
<223> OTHER INFORMATION: Synthetic

<400> SEQUENCE: 38

```
caagctcccc agtcagcctg gtcaaaggga t                                       31
```

<210> SEQ ID NO 39
<211> LENGTH: 41
<212> TYPE: PRT
<213> ORGANISM: Homo sapiens

<400> SEQUENCE: 39

```
Phe Asp Gln Asp Asp Trp Gly Ala Trp Gln Lys Phe Thr Ala Ser Ala
1               5                   10                  15

Gly Ile Gln Val Val Gly Asp Asp Leu Thr Val Thr Asn Pro Lys Arg
            20                  25                  30

Ile Ala Lys Ala Val Asn Glu Lys Ser
        35                  40
```

<210> SEQ ID NO 40
<211> LENGTH: 14
<212> TYPE: PRT
<213> ORGANISM: Homo sapiens

<400> SEQUENCE: 40

```
Phe Asp Gln Asp Asp Trp Gly Ala Trp Gln Lys Phe Thr Ala
1               5                   10
```

<210> SEQ ID NO 41
<211> LENGTH: 11
<212> TYPE: PRT
<213> ORGANISM: Homo sapiens

<400> SEQUENCE: 41

```
Lys Arg Ile Ala Lys Ala Val Asn Glu Lys Ser
1               5                   10
```

<210> SEQ ID NO 42
<211> LENGTH: 36
<212> TYPE: DNA
<213> ORGANISM: Artificial Sequence
<220> FEATURE:
<223> OTHER INFORMATION: Synthetic

<400> SEQUENCE: 42

```
ctacctggat tcctgcagcg gctgtgaact tctgcc                                  36
```

-continued

<210> SEQ ID NO 43
<211> LENGTH: 36
<212> TYPE: DNA
<213> ORGANISM: Artificial Sequence
<220> FEATURE:
<223> OTHER INFORMATION: Synthetic

<400> SEQUENCE: 43
ggcagaagtt cacagccgct gcaggaatcc aggtag         36

<210> SEQ ID NO 44
<211> LENGTH: 29
<212> TYPE: DNA
<213> ORGANISM: Artificial Sequence
<220> FEATURE:
<223> OTHER INFORMATION: Synthetic

<400> SEQUENCE: 44
ccactacctg gattgctgca ctggctgtg              29

<210> SEQ ID NO 45
<211> LENGTH: 29
<212> TYPE: DNA
<213> ORGANISM: Artificial Sequence
<220> FEATURE:
<223> OTHER INFORMATION: Synthetic

<400> SEQUENCE: 45
cacagccagt gcagcaatcc aggtagtgg              29

<210> SEQ ID NO 46
<211> LENGTH: 32
<212> TYPE: DNA
<213> ORGANISM: Artificial Sequence
<220> FEATURE:
<223> OTHER INFORMATION: Synthetic

<400> SEQUENCE: 46
acggccttgg cgatcgcctt tgggttggtc ac           32

<210> SEQ ID NO 47
<211> LENGTH: 34
<212> TYPE: DNA
<213> ORGANISM: Artificial Sequence
<220> FEATURE:
<223> OTHER INFORMATION: Synthetic

<400> SEQUENCE: 47
cctgcactgg ctgtgaacgc ctgccaagct cccc         34

<210> SEQ ID NO 48
<211> LENGTH: 32
<212> TYPE: DNA
<213> ORGANISM: Artificial Sequence
<220> FEATURE:
<223> OTHER INFORMATION: Synthetic

<400> SEQUENCE: 48
gtgaccaacc caaaggcgat cgccaaggcc gt           32

<210> SEQ ID NO 49
<211> LENGTH: 24
<212> TYPE: DNA
<213> ORGANISM: Artificial Sequence
<220> FEATURE:
<223> OTHER INFORMATION: Synthetic

```
<400> SEQUENCE: 49
gcaaggggca ccagtcttga tctg                                              24

<210> SEQ ID NO 50
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa is any amino acid but cysteine

<400> SEQUENCE: 50

Gly Tyr Thr Phe Thr Ser Xaa Val Met Asn
1               5                   10

<210> SEQ ID NO 51
<211> LENGTH: 119
<212> TYPE: PRT
<213> ORGANISM: Artificial Sequence
<220> FEATURE:
<223> OTHER INFORMATION: Synthetic
<220> FEATURE:
<221> NAME/KEY: x
<222> LOCATION: (7)..(32)
<223> OTHER INFORMATION: Xaa is any amino acid but cysteine

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Xaa
            20                  25                  30

Val Met Asn Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Phe Tyr Tyr Gly Asn Phe Asp Asn Trp Gly Gln Gly
            100                 105                 110

Thr Leu Val Thr Val Ser Ser
            115
```